United States Patent
Tsurui et al.

(10) Patent No.: US 9,376,701 B2
(45) Date of Patent: Jun. 28, 2016

(54) METHOD FOR SECRETORY PRODUCTION OF PROTEIN

(71) Applicant: AJINOMOTO CO., INC., Tokyo (JP)

(72) Inventors: Noriko Tsurui, Kanagawa (JP); Hiroshi Itaya, Kanagawa (JP); Yoshimi Kikuchi, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 6 days.

(21) Appl. No.: 14/250,548

(22) Filed: Apr. 11, 2014

(65) Prior Publication Data

US 2014/0220637 A1    Aug. 7, 2014

Related U.S. Application Data

(63) Continuation of application No. PCT/JP2012/077545, filed on Oct. 25, 2012.

(30) Foreign Application Priority Data

Oct. 25, 2011   (JP) ................. 2011-233864

(51) Int. Cl.
*C12P 21/02*   (2006.01)
*C07K 14/34*   (2006.01)
*C12N 15/77*   (2006.01)

(52) U.S. Cl.
CPC ................. *C12P 21/02* (2013.01); *C07K 14/34* (2013.01); *C12N 15/77* (2013.01); *C07K 2319/02* (2013.01); *C07K 2319/50* (2013.01)

(58) Field of Classification Search
None
See application file for complete search history.

(56) References Cited

U.S. PATENT DOCUMENTS

| | | |
|---|---|---|
| 4,965,197 A | 10/1990 | Liebl et al. |
| 6,027,920 A | 2/2000 | Joliff et al. |
| 6,841,361 B1 | 1/2005 | Oka et al. |
| 7,252,972 B2 | 8/2007 | Kikuchi et al. |
| 7,723,067 B2 | 5/2010 | Kikuchi et al. |
| 7,723,097 B2 | 5/2010 | D'Elia et al. |
| 7,972,829 B2 | 7/2011 | Kikuchi et al. |
| 8,062,869 B2 | 11/2011 | Nakanishi et al. |
| 8,093,346 B2 | 1/2012 | Suzuki et al. |
| 8,105,802 B2 | 1/2012 | Umezawa et al. |
| 8,597,907 B2 | 12/2013 | Date et al. |
| 2003/0082746 A1 | 5/2003 | Kikuchi et al. |
| 2004/0126847 A1 | 7/2004 | Kikuchi et al. |
| 2007/0065912 A1* | 3/2007 | Carson ............ C07K 16/00 435/69.1 |
| 2007/0184525 A1 | 8/2007 | Date et al. |
| 2010/0297729 A1 | 11/2010 | Kikuchi et al. |

FOREIGN PATENT DOCUMENTS

| | | |
|---|---|---|
| JP | 06-502548 | 3/1994 |
| JP | 11-169182 | 6/1999 |
| JP | 11-341991 | 12/1999 |
| JP | 2002-291476 | 10/2002 |
| WO | WO01/23591 | 4/2001 |
| WO | WO02/081694 | 10/2002 |
| WO | WO2013/062029 | 5/2013 |

OTHER PUBLICATIONS

Billman-Jacobe, H., et al., "Expression and Secretion of Heterologous Proteases by Corynebacterium glutamicum," Appl. Environmen. Microbiol. 1995;61(4):1610-1613.
Christensen, T., et al., "High Level Expression of Recombinant Genes in Aspergillus Oryzae," Bio/Technology 1988;6:1419-1422.
Cregg, J. M., et al., "Recent Advances in the Expression of Foreign Genes in Pichia pastoris," BiolTechnology 1993;11:905-910.
Dunn-Coleman, N. S., et al., "Commercial Levels of Chymosin Production by Aspergillus," Bio/Technology 1991;9:976-981.
Hansmeier, N., et al., "Classification of hyper-variable Corynebacterium glutamicum surface-layer proteins by sequence analyses and atomic force microscopy," J. Biotechnol. 2004;112:177-193.
Liebl, W., et al., "Expression, Secretion, and Processing of *Staphylococcal* Nuclease by Corynebacterium glutamicum," J. Bacteriol. 1992;174(6):1854-1861.
Peyret, J. L., et al., "Characterization of the cspB gene encoding PS2, an ordered surface-layer protein in Corynebacterium glutamicum," Mol. Microbiol. 1993;9(1):97-109.
Simonen, M., et al., "Protein Secretion in *Bacillus* Species," Microbiol. Rev. 1993;57(1):109-137.
International Preliminary Report on Patentability for PCT Patent App. No. PCT/JP2012/077545 (Apr. 29, 2014).
Salim, K., et al., "Heterologous Expression of the Mycobacterium tuberculosis Gene Encoding Antigen 85A in Coryne bacterium glutamicum," Appl. Environmen. Microbiol. 1997;63(11):4392-4400.
International Search Report for PCT Patent App. No. PCT/JP2012/077545 (Nov. 27, 2012).
Database Geneseq [Online], "Brevibacterium flavum terminal amino acid sequence," Database accession no. AAW37480, Mar. 27, 1998 retrieved Aug. 5, 2015 from http://ibis.internal.epo.org/exam/dbfetch.jsp?id=GSP: AAW37480.
Database Geneseq [Online], "Brevibacterium flavum terminal amino acid sequence," Database accession No. AAW37480, Mar. 27, 1998, retrieved Aug. 5, 2015 from http://ibis.internal.epo.org/exam/dbfetch.jsp?id=GSP:AAW37480.
Supplementary European Search Report for European Patent App. No. 12843347.1 (Aug. 26, 2015).

* cited by examiner

*Primary Examiner* — Suzanne M Noakes
*Assistant Examiner* — Jae W Lee
(74) *Attorney, Agent, or Firm* — Shelly Guest Cermak; Cermak Nakajima & McGowan LLP

(57) ABSTRACT

A novel technique for improving secretory production of a heterologous protein by coryneform bacteria is described, and thereby a method for secretory production of a heterologous protein is provided. A coryneform bacterium is cultured so that it secretes a heterologous protein, the bacterium having a genetic construct which includes a promoter sequence that functions in the coryneform bacterium, a nucleic acid sequence coding for a signal peptide that functions in the coryneform bacterium, which is ligated downstream from the promoter sequence, and a nucleic acid sequence coding for a fusion protein having an amino acid sequence that includes Gln-Glu-Thr and the heterologous protein, which is ligated downstream from the nucleic acid sequence coding for the signal peptide.

10 Claims, 5 Drawing Sheets

METHOD FOR SECRETORY PRODUCTION OF PROTEIN

This application is a Continuation of, and claims priority under 35 U.S.C. §120 to, International Application No. PCT/JP2012/077545, filed Oct. 25, 2012, and claims priority therethrough under 35 U.S.C. §119 to Japanese Patent Application No. 2011-233864, filed Oct. 25, 2011, the entireties of which are incorporated by reference herein. Also, the Sequence Listing filed electronically herewith is hereby incorporated by reference (File name: 2014-04-11T_US-511_Seq_List; File size: 35 KB; Date recorded: Apr. 11, 2014).

BACKGROUND OF THE INVENTION

1. Field of the Invention

The present invention relates to a method for secretory production of a heterologous protein.

2. Brief Description of the Related Art

Secretory production of heterologous proteins by microorganisms has been previously reported, and includes secretory production by a *Bacillus* bacterium (Microbiol. Rev., 57, 109-137 (1993)), methanol-assimilating yeast, *Pichia pastoris* (Biotechnol., 11, 905-910 (1993)), filamentous fungi of the genus *Aspergillus* (Biotechnol., 6, 1419-1422 (1988) and Biotechnol., 9, 976-981 (1991)), and so forth.

Coryneform bacteria has also been used for the secretory productions of heterologous proteins, and examples include the secretion of a nuclease and a lipase by *Corynebacterium glutamicum* (henceforth also abbreviated as *C. glutamicum*) (U.S. Pat. No. 4,965,197, J. Bacteriol., 174, 1854-1861 (1992)), secretion of a protease such as subtilisin (Appl. Environ. Microbiol., 61, 1610-1613 (1995)), secretion of a protein using signal peptides of cell surface layer proteins PS1 and PS2 (also referred to as CspB) of coryneform bacteria (Japanese Patent Laid-open (Kohyo) No. 6-502548), secretion of a fibronectin-binding protein using the signal peptide of PS2 (CspB) (Appl. Environ. Microbiol., 63, 4392-4400 (1997)), secretion of protransglutaminase using signal peptides of PS2 (CspB) and SlpA (also referred to as CspA) (Japanese Patent No. 4320769), secretion of a protein using a variant type secretion system (Japanese Patent Laid-open (Kokai) No. 11-169182), secretion of a protransglutaminase by a variant strain (Japanese Patent No. 4362651), secretion of a protein using a Tat-dependent signal peptide (Japanese Patent No. 4730302), and so forth.

It has also been reported that when producing a heterologous protein connected to a signal peptide, a sequence of one or more amino acid residues from the N-terminal sequence of a cell wall protein of a *Bacillus* bacterium should be inserted between the signal peptide and the heterologous protein (Japanese Patent Laid-open (Kokai) No. 11-341991 and Japanese Patent Laid-open (Kokai) No. 2000-316579).

CspB (PS2) is a cell surface layer protein found in *C. glutamicum* (Mol. Microbiol., 9, 97-109 (1993)). There are *Corynebacterium* bacterium strains having a homologue of the cell surface layer protein CspB, and those that do not have such a CspB homologue. Amino acid sequences of CspB homologues have been reported for 28 strains of *C. glutamicum* (J. Biotechnol., 112, 177-193 (2004)). When comparing the N-terminal amino acid sequences of the CspB homologues from these 28 strains, it was found that both the signal sequences of 30 amino acid residues, as well as the N-terminal 3 amino acid residues (Gln-Glu-Thr) of the mature proteins, were completely conserved (J. Biotechnol., 112, 177-193 (2004)).

As described above, methods for secretory production of a heterologous protein connected to the signal peptide of CspB (PS2) are known (for example, Japanese Patent Laid-open (Kohyo) No. 6-502548 and Japanese Patent No. 4320769, Appl. Environ. Microbiol., 63, 4392-4400 (1997)). Moreover, it has also been reported that, by inserting 1, 14, or 38 amino acid residues of the N-terminus of the mature CspB protein of *C. glutamicum* ATCC 13869 (SEQ ID NO: 96) between the signal peptide and the heterologous protein (protransglutaminase), the heterologous protein can be produced by secretory production, with the 38 amino acid residues insertion providing an increased secretory production amount of the protransglutaminase (Japanese Patent No. 4320769). However, inserting an amino acid sequence that includes Gln-Glu-Thr between the signal peptide and the heterologous protein for expression of the heterologous protein has not been previously reported.

It has been reported that the N-terminal amino acid residue of the mature cell surface layer protein CspB of *C. glutamicum* is blocked by the Edman degradation, and thus it has been suggested that the original N-terminal amino acid residue of glutamine is converted into a pyroglutamic acid residue (Mol. Microbiol., 9, 97-109 (1993)). However, it has not been previously reported that when expressing a heterologous protein in which an amino acid sequence including Gln-Glu-Thr is inserted between a signal peptide and the heterologous protein, the N-terminal glutamine residue of the heterologous protein can be converted into a pyroglutamic acid residue.

SUMMARY OF THE INVENTION

Aspects to be Achieved by the Invention

An aspect of the present invention is to develop a novel technique for improving secretory production of a heterologous protein by a coryneform bacterium, and thereby to provide a method for secretory production of a heterologous protein using a coryneform bacterium.

In a method for secretory production of a heterologous protein using a signal peptide, the secreted amount of the heterologous protein can be increased by inserting an amino acid sequence that includes Gln-Glu-Thr between the signal peptide and the heterologous protein.

That is, the present invention includes the following aspects:

It is an aspect of the present invention to provide a method for producing a heterologous protein comprising: A) culturing a coryneform bacterium having a genetic construct for secretory expression of a heterologous protein, B) allowing the bacterium to produce and secrete the heterologous protein, and C) collecting the heterologous protein, wherein the genetic construct comprises: i) a promoter sequence that functions in the coryneform bacterium, ii) a first nucleic acid sequence coding for a signal peptide that functions in the coryneform bacterium, wherein said first nucleic acid sequence is ligated downstream from the promoter sequence, and iii) a second nucleic acid sequence coding for a fusion protein having: a) an amino acid sequence comprising Gln-Glu-Thr, and b) the heterologous protein, wherein said second nucleic acid sequence is ligated downstream from the first nucleic acid sequence coding for the signal peptide, and wherein the amino acid sequence comprising Gln-Glu-Thr does not consist of the amino acid residues at positions 1 to 14 or positions 1 to 38 of SEQ ID NO: 96.

It is a further aspect of the present invention to provide the method as described above, wherein the amino acid sequence comprising Gln-Glu-Thr is selected from the group consisting of:

(A)  Gln-Glu-Thr (B)  Gln-Glu-Thr-Xaa1                    (SEQ ID NO: 102)

(C)  Gln-Glu-Thr-Xaa1-Xaa2               (SEQ ID NO: 103)

(D)  Gln-Glu-Thr-Xaa1-Xaa2-Xaa3          (SEQ ID NO: 104)

(E) an amino acid sequence consisting of Gln-Glu-Thr fused with the amino acid residues at positions 4 to 7 of a mature CspB protein,
(F) an amino acid sequence consisting of Gln-Glu-Thr fused with the amino acid residues at positions 4 to 8 of a mature CspB protein,
(G) an amino acid sequence consisting of Gln-Glu-Thr fused with the amino acid residues at positions 4 to 17 of a mature CspB protein,
(H) an amino acid sequence consisting of Gln-Glu-Thr fused with the amino acid residues at positions 4 to 50 of a mature CspB protein,
wherein Xaa1 is Asn, Gly, Thr, Pro, or Ala; Xaa2 is Pro, Thr, or Val; and Xaa3 is Thr or Tyr.

It is a further aspect of the present invention to provide the method as described above, wherein the amino acid sequence comprising Gln-Glu-Thr is selected from the group consisting of Gln-Glu-Thr-Asn-Pro-Thr (SEQ ID NO: 97), Gln-Glu-Thr-Gly-Thr-Tyr (SEQ ID NO: 98), Gln-Glu-Thr-Thr-Val-Thr (SEQ ID NO: 99), Gln-Glu-Thr-Pro-Val-Thr (SEQ ID NO: 100), and Gln-Glu-Thr-Ala-Val-Thr (SEQ ID NO: 101).

It is a further aspect of the present invention to provide the method as described above, wherein the genetic construct further comprises a third nucleic acid sequence coding for an amino acid sequence capable of enzymatic digestion between the amino acid sequence comprising Gln-Glu-Thr and the heterologous protein.

It is a further aspect of the present invention to provide the method as described above, wherein the amino acid sequence capable of enzymatic digestion is a recognition sequence of factor Xa protease, or a recognition sequence of ProTEV protease.

It is a further aspect of the present invention to provide the method as described above, wherein the recognition sequence is the amino acid sequence shown in SEQ ID NO: 105 or 106.

It is a further aspect of the present invention to provide the method as described above, wherein the signal peptide that functions in the coryneform bacterium is the signal peptide of CspB derived from a coryneform bacterium.

It is a further aspect of the present invention to provide the method as described above, wherein the signal peptide of CspB has the amino acid sequence shown in SEQ ID NO: 92.

It is a further aspect of the present invention to provide the method as described above, wherein the coryneform bacterium belongs to the genus *Corynebacterium* or *Brevibacterium*.

It is a further aspect of the present invention to provide the method as described above, wherein the coryneform bacterium is *Corynebacterium glutamicum* or *Corynebacterium stationis*.

DESCRIPTION OF THE PREFERRED EMBODIMENTS

Figure 1:
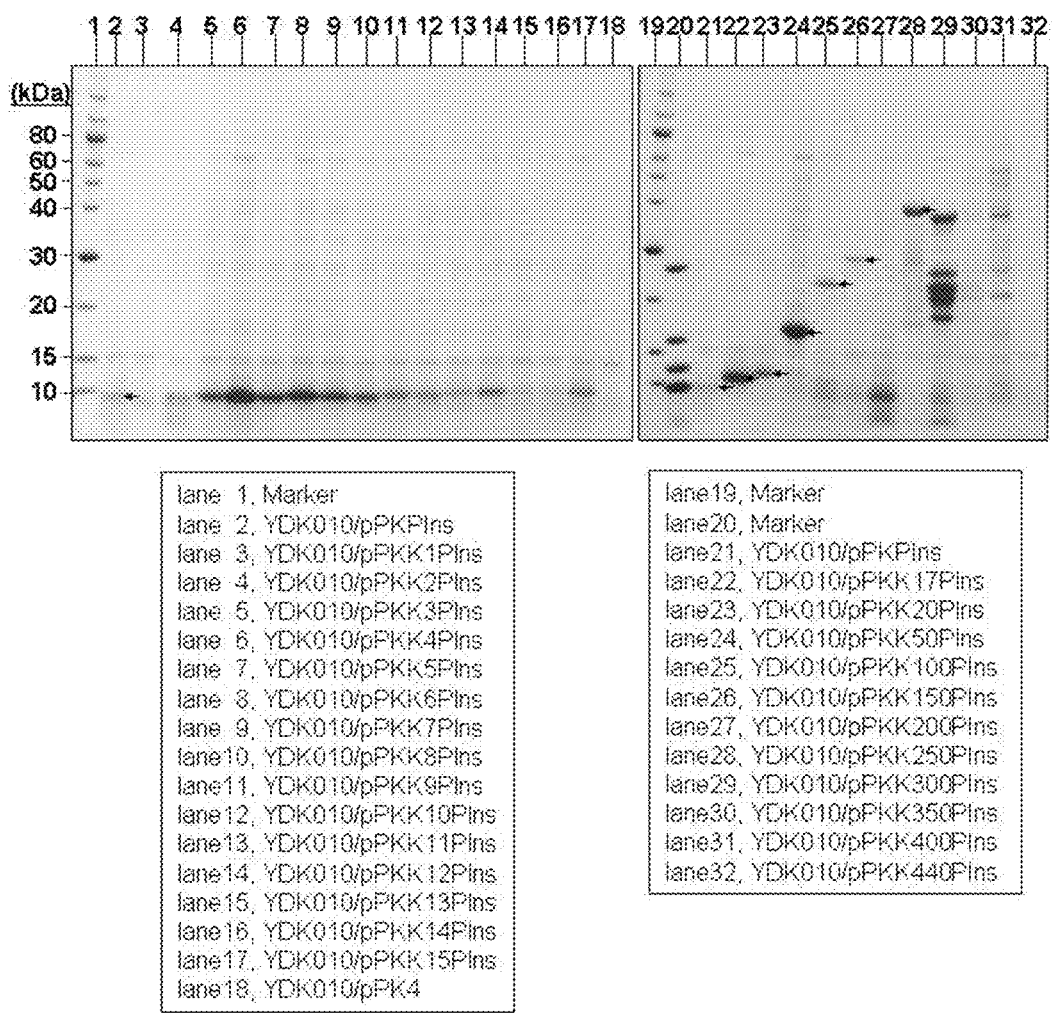
FIG. 1 is a photograph showing the results of SDS-PAGE of proinsulin fused with the signal sequence of CspB of *C. glutamicum* ATCC 13869 and an N-terminal sequence of the mature CspB of *C. glutamicum* ATCC 13869, which was expressed in the *C. glutamicum* YDK010 strain.

The present invention provides a method for producing a heterologous protein by culturing a coryneform bacterium having a genetic construct for secretory expression of a heterologous protein, and collecting the heterologous protein produced by the secretory production, wherein the genetic construct includes a promoter sequence that functions in the coryneform bacterium, ligated upstream to a nucleic acid sequence coding for a signal peptide that functions in the coryneform bacterium, which is ligated upstream to a nucleic acid sequence coding for a fusion protein that includes an amino acid sequence that includes the tripeptide Gln-Glu-Thr and the heterologous protein (henceforth also referred to as the "method of the present invention" or "method for producing a heterologous protein of the present invention").

The chosen coryneform bacterium used for the method described herein contains the genetic construct for secretory expression of a heterologous protein, and therefore it is able to secrete the produced heterologous protein.

The coryneform bacterium can also referred to as the "bacterium of the present invention" or "coryneform bacterium of the present invention". Further, the genetic construct for secretory expression of a heterologous protein harbored by the bacterium of the present invention can also be referred to as the "genetic construct used for the present invention". Further, the fusion protein that includes an amino acid sequence of Gln-Glu-Thr and a heterologous protein can also be referred to as the "fusion protein of the present invention".

The expression that a protein is "secreted" means that the protein is transported out of the bacterial cell, that is, extracellularly transported. The expression that a protein is "secreted" of course can include when some or all the protein molecules eventually are present in the medium in completely free forms, and also when some or all of the protein molecules are present in the cell surface layer, and when some are present in the medium and some are present the cell surface layer.

That is, the "ability to produce a heterologous protein by secretory production" can refer to the ability of the bacterium to secrete the heterologous protein into a medium or the cell surface layer, wherein the heterologous protein accumulates to such an extent that the it can be collected from the medium or the cell surface layer, when the bacterium is cultured in the medium. The accumulation amount may be, for example, in terms of the accumulation amount in the medium, such as 10 µg/L or more, 1 mg/L or more, 100 mg/L or more, or 1 g/L or more. Also, the accumulation amount may be, for example, in terms of the accumulation amount in the cell surface layer, such an amount that if the heterologous protein in the cell surface layer is collected and suspended in a liquid of the same volume as the medium, the concentration of the heterologous protein in the suspension can be 10 µg/L or more, 1 mg/L or more, or 100 mg/L or more. In addition, the term "protein" can also include molecules referred to as peptide or polypeptide.

The "heterologous protein" can refer to an exogenous protein relative to the coryneform bacterium that expresses and secretes that protein. The heterologous protein may be, for example, a protein derived from a microorganism, a protein derived from a plant, a protein derived from an animal, a protein derived from a virus, or even an artificially designed protein. The heterologous protein may be a monomer or a multimer. The multimeric protein can refer to a protein that is a multimer of two or more subunits. In the multimer, the subunits may be linked by covalent bonds such as disulfide bonds, linked by non-covalent bonds such as hydrogen bonds and hydrophobic interaction, or linked by a combination thereof. The multimer can include one or more intermolecular disulfide bonds. The multimer may be a homo-multimer consisting of a single kind of subunit, or may be a hetero-multimer consisting of two or more kinds of subunits. In the case where the multimeric protein is a hetero-multimer, at least one subunit of the hetero-multimer can be a heterologous protein. That is, all the subunits may be heterologous, or only a part of subunits may be heterologous. Although the heterologous protein may be a secretory protein in nature, or may be a non-secretory protein in nature, it is preferably a secretory protein in nature. Specific examples of the "heterologous protein" will be described herein.

The heterologous protein can be a single kind of protein, or two or more kinds of proteins. Moreover, when the heterologous protein is a hetero-multimer, only one kind of subunit may be produced, or two or more kinds of subunits may be produced. That is, the "secretory production of a heterologous protein" can include secretory production of all the subunits constituting an objective heterologous protein, as well as secretory production of only a part of the subunits constituting an objective heterologous protein.

The coryneform bacteria can be aerobic gram-positive bacilli, and include *Corynebacterium* bacteria, *Brevibacterium* bacteria, *Microbacterium* bacteria, and so forth. The coryneform bacteria can include bacteria which have previously been classified into the genus *Brevibacterium* but have since been united into the genus *Corynebacterium* (Int. J. Syst. Bacteriol., 41, 255 (1991)). Advantages of the coryneform bacteria include that they inherently secrete an extremely small amount of proteins out of cells as compared with fungi, yeasts, *Bacillus* bacteria, etc, which are conventionally used for secretory production of proteins, and therefore the purification process of the heterologous protein can be simplified or eliminated. Also, coryneform bacteria can grow well in a simple medium containing a saccharide, ammonia, mineral salts, etc., and therefore are excellent in view of cost of medium, culture method, and culture productivity, and so forth.

Specific examples of coryneform bacteria include the following species:
*Corynebacterium acetoacidophilum*
*Corynebacterium acetoglutamicum*
*Corynebacterium alkanolyticum*
*Corynebacterium callunae*
*Corynebacterium glutamicum*
*Corynebacterium lilium*
*Corynebacterium melassecola*
*Corynebacterium thermoaminogenes* (*Corynebacterium efficiens*)
*Corynebacterium herculis*
*Brevibacterium divaricatum*
*Brevibacterium flavum*
*Brevibacterium immariophilum*
*Brevibacterium lactofermentum* (*Corynebacterium glutamicum*)
*Brevibacterium roseum*
*Brevibacterium saccharolyticum*
*Brevibacterium thiogenitalis*
*Corynebacterium ammoniagenes* (*Corynebacterium stationis*)
*Brevibacterium album*
*Brevibacterium cerinum*
*Microbacterium ammoniaphilum*

Specific examples of coryneform bacteria include the following strains:
*Corynebacterium acetoacidophilum* ATCC 13870
*Corynebacterium acetoglutamicum* ATCC 15806
*Corynebacterium alkanolyticum* ATCC 21511
*Corynebacterium callunae* ATCC 15991
*Corynebacterium glutamicum* ATCC 13020, ATCC 13032, ATCC 13060, ATCC 13869, FERM BP-734
*Corynebacterium lilium* ATCC 15990
*Corynebacterium melassecola* ATCC 17965
*Corynebacterium thermoaminogenes* AJ12340 (FERM BP-1539)
*Corynebacterium herculis* ATCC 13868
*Brevibacterium divaricatum* ATCC 14020
*Brevibacterium flavum* ATCC 13826, ATCC 14067, AJ12418 (FERM BP-2205)
*Brevibacterium immariophilum* ATCC 14068
*Brevibacterium lactofermentum* ATCC 13869
*Brevibacterium roseum* ATCC 13825
*Brevibacterium saccharolyticum* ATCC 14066
*Brevibacterium thiogenitalis* ATCC 19240
*Corynebacterium ammoniagenes* (*Corynebacterium stationis*) ATCC 6871, ATCC 6872
*Brevibacterium album* ATCC 15111
*Brevibacterium cerinum* ATCC 15112
*Microbacterium ammoniaphilum* ATCC 15354

These strains are available from, for example, the American Type Culture Collection (Address: 12301 Parklawn Drive, Rockville, Md. 20852, P.O. Box 1549, Manassas, Va. 20108, United States of America). That is, registration numbers are assigned to the strains, and the strains can be ordered by using these registration numbers (refer to www.atcc.org/). The registration numbers of the strains are listed in the catalogue of the American Type Culture Collection.

In particular, the *Corynebacterium glutamicum* (*C. glutamicum*) AJ12036 strain (FERM BP-734), which was isolated as a streptomycin (Sm) resistant mutant strain from the wild-type strain, *C. glutamicum* ATCC 13869, is predicted to have a mutation in the functional gene responsible for secretion of proteins, and as a result is able to secrete extremely high amounts of heterologous proteins. Specifically, this strain can secrete as much as about 2 to 3 times under optimum culture conditions, as compared with the parent strain, and therefore it is preferred as a host bacterium. The AJ12036 strain was originally deposited at the National Institute of Bioscience and Human-Technology, Agency of Industrial Science and Technology (currently, the independent administrative agency, National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Mar. 26, 1984 as an international deposit, and assigned an accession number of FERM BP-734.

Moreover, a strain with an enhanced ability to produce a protein by secretory production can be selected from coryneform bacterial strains, such as those described above which have been treated with a mutagenesis method or a genetic recombination method, and used as a host. For example, after a chosen, or parent, strain is treated with ultraviolet irradiation or a chemical mutation agent such as N-methyl-N'-nitrosoguanidine, a strain having an enhanced ability to produce a protein by secretory production can be selected.

Furthermore, if a strain that has been modified as described above so that it does not produce a cell surface layer protein is used as the host, the heterologous protein that is secreted in the medium or on the cell surface layer can be easily purified. Such a modification can be carried out by introducing a mutation into the coding region of the cell surface layer protein, or an expression control region thereof, on the chromosome by mutagenesis or genetic recombination. An example of a coryneform bacterium that has been modified so that it does not produce a cell surface layer protein is the *C. glutamicum* YDK010 strain (WO2004/029254), which is a cell surface layer protein PS2 deficient strain of the *C. glutamicum* AJ12036 strain (FERM BP-734).

That is, the bacterium may have reduced activity(s) of cell surface layer protein(s). The cell surface layer protein constitutes the surface layer (S layer) of bacteria or archaea. Examples of cell surface layer proteins of coryneform bacteria include PS1 and PS2 (also referred to as CspB) of *C. glutamicum*, and SlpA (also referred to as CspA) of *C. stationis*. It is exemplary to reduce the activity of the PS2 protein. The nucleotide sequence of the cspB gene of *C. glutamicum* ATCC 13869 and the amino acid sequence of the PS2 protein encoded by the gene are shown in SEQ ID NOS: 94 and 95, respectively. Examples of the cspB gene homologue in other *C. glutamicum* strains will be mentioned later.

Since the nucleotide sequence of a gene coding for a cell surface layer protein may differ depending on species or strain to which the coryneform bacterium belongs, the gene coding for a cell surface layer protein may be a variant of the aforementioned nucleotide sequence, so long as the gene codes for a protein that retains its original function. The expression "retains its original function" can mean that if the activity of the protein is reduced in a coryneform bacterium, the secretory production amount of a heterologous protein is increased compared with that observed for a non-modified strain. Further, the expression "retains its original function" can also mean that, in the case of CspB, for example, increase of the secretory production amount of the heterologous protein can be attained with the insertion sequence of the present invention, as described herein. The descriptions concerning variants of CspB and the gene coding for it described herein can also be applied *mutatis mutandis* to the other cell surface layer proteins and genes coding for them.

The expression "that if the activity of the protein is reduced in a coryneform bacterium, the secretory production amount of a heterologous protein is increased compared with that observed for a non-modified strain" can refer to imparting an ability to produce a heterologous protein by secretory production in an amount larger than that observed for a non-modified strain such as wild-type strain or parent strain to a coryneform bacterium when the activity thereof is reduced in the coryneform bacterium. The expression "to produce a heterologous protein by secretory production in an amount larger than that observed for a non-modified strain" can mean, for example, that the heterologous protein is produced by secretory production in an amount larger than that observed for a non-modified strain by 10% or more, 20% or more, 30% or more, or even 100% or more, relative to the accumulation amount in the medium and/or the cell surface layer. However, it is not particularly limited to this definition so long as the secretory production amount of the heterologous protein increases compared with that observed for a non-modified strain. In addition, the expression "to produce a heterologous protein by secretory production in an amount larger than that observed for a non-modified strain" may also mean that whereas the heterologous protein cannot be detected when a non-concentrated culture supernatant of a non-modified strain is applied to SDS-PAGE and stained with CBB, the heterologous protein can be detected when a non-concentrated culture supernatant of a modified strain is applied to SDS-PAGE and stained with CBB.

Whether a protein has a property that if the activity of the protein is reduced in a coryneform bacterium, the secretory production amount of a heterologous protein is increased compared with that observed for a non-modified strain can be confirmed by modifying a strain belonging to the coryneform bacteria such that the activity of the protein is reduced, quantifying the secretory production amount of the heterologous protein observed when the modified strain is cultured in a medium, and comparing the quantified amount with the secretory production amount of the heterologous protein observed when the non-modified strain (un-modified strain) is cultured in the medium.

The expression "activity of a cell surface layer protein is reduced" can include when a coryneform bacterium has been modified so that the activity of a cell surface layer protein is reduced, or also when the activity of a cell surface layer protein is inherently reduced in a coryneform bacterium. The expression "activity of a cell surface layer protein is inherently reduced in a coryneform bacterium" can include when a coryneform bacterium is inherently deficient in a cell surface layer protein. That is, examples of a coryneform bacterium in which the activity of a cell surface layer protein is reduced can include a coryneform bacterium that is inherently deficient in a cell surface layer protein. Examples of the "a coryneform bacterium which is inherently deficient in a cell surface layer protein" can include a coryneform bacterium that is inherently deficient in the gene encoding a cell surface layer protein. The expression "a coryneform bacterium is inherently deficient in a cell surface layer protein" can mean that a coryneform bacterium is inherently deficient in one or more proteins selected from cell surface layer protein(s) found in other strain(s) of the species to which the coryneform bacterium belongs. For example, "*C. glutamicum* is inherently deficient in a cell surface layer protein" may mean that a *C. glutamicum* strain is inherently deficient in one or more proteins selected from cell surface layer protein(s) found in other *C. glutamicum* strain(s), i.e. for example, deficient in PS1 and/or PS2 (CspB). Examples of the coryneform bacterium that is inherently deficient in a cell surface layer protein include *C. glutamicum* ATCC 13032, which is inherently deficient in the cspB gene.

The expression "activity of a protein is reduced" can mean that the activity of the target protein is decreased compared with that of a non-modified strain such as a wild-type strain or a parent strain, which includes when the activity completely disappears. Specifically, the expression "activity of a protein is reduced" means that the number of molecules of the protein per cell is reduced, and/or the function of each molecule of the protein is reduced compared with those of a non-modified strain. That is, the term "activity" can mean the transcription amount (the amount of mRNA) of a gene encoding the protein or the amount of the protein, as well as the catalytic activity of the protein. In addition, when the "number of molecules of the protein per cell is reduced" can include when the protein does not exist at all. Further, the expression "function of each molecule of the protein is reduced" can include when the function of each molecule of the protein completely disappears.

Modifications which result in the reduction of the activity of a protein can include, for example, reducing the expression of a gene coding for the protein. "Reduction of gene expression" can also be referred to as "attenuation of gene expression". The reduction of gene expression may be induced by, for example, reduction of transcription efficiency, reduction of translation efficiency, or a combination of these. Expression of a gene can be reduced by modifying an expression control sequence of the gene, such as a promoter and/or the Shine-Dalgarno (SD) sequence. When an expression control sequence is modified, one nucleotide or more, two nucleotides or more, three nucleotides or more, of the expression control sequence can be modified. Moreover, a part or all of the expression control sequence may be deleted. Gene expression can also be reduced by, for example, manipulating a factor responsible for expression control. Examples of factors responsible for expression control include molecules responsible for transcription or translation control, such as inducers, inhibitors, etc.; proteins responsible for transcription or translation control, such as transcription factors etc.; nucleic acids responsible for transcription or translation control, such as siRNA etc.; and so forth.

The activity of a protein can also be reduced by, for example, disrupting the gene coding for the protein. Disruption of a gene can be attained by, for example, deleting a part or all of the coding region of the gene on the chromosome. Furthermore, the total gene including sequences upstream and downstream from the gene on a chromosome may be deleted. The region to be deleted may be any region such as an N-terminal region, an internal region, or a C-terminal region, so long as the activity of the protein is reduced. Deleting a longer region can usually more surely inactivate the gene. Further, it is preferred that the reading frames of the sequences upstream and downstream from the region to be deleted are not the same.

Disruption of a gene can also be attained by, for example, introduction of a mutation for an amino acid substitution (missense mutation), a stop codon (nonsense mutation), a frame shift mutation which adds or deletes one or two nucleotides into the coding region of the gene on a chromosome, or the like (Journal of Biological Chemistry, 272:8611-8617 (1997); Proceedings of the National Academy of Sciences, USA, 95 5511-5515 (1998); Journal of Biological Chemistry, 26 116, 20833-20839 (1991)).

Disruption of a gene can also be attained by, for example, inserting another sequence into the coding region of the gene on a chromosome. The insertion site may be in any region of the gene, and insertion of a longer region can usually more surely inactivate the gene. It is preferred that the reading frames of the sequences upstream and downstream from the insertion site are not the same. The sequence to be inserted is not particularly limited so long as a sequence that reduces or eliminates the activity of the encoded protein is chosen, and examples include, for example, a marker gene such as an antibiotic resistance gene, a gene useful for production of a heterologous protein, and so forth.

Such modification of a gene on a chromosome as described above can be attained by, for example, preparing a deficient-type gene in which a partial sequence of the gene is deleted so that it cannot produce a protein that can normally function, and transforming a bacterium with a recombinant DNA containing the deficient-type gene to cause homologous recombination between the deficient-type gene and the gene on a chromosome and thereby substitute the deficient-type gene for the gene on the chromosome. In such a case, the operation is simplified if a marker gene selected according to the characteristics of the host, such as auxotrophy, is included in the recombinant DNA. The protein encoded by the deficient-type gene has a conformation different from that of a wild-type protein, even if it is produced, and thus the function thereof is reduced or eliminated. Gene disruption methods based on gene substitution utilizing homologous recombination have been already reported, and include "Red driven integration" (Datsenko, K. A, and Wanner, B. L., Proc. Natl. Acad. Sci. USA, 97:6640-6645 (2000)), a method of using a linear DNA such as by utilizing Red driven integration in combination with an excision system derived from λ phage (Cho, E. H., Gumport, R. I., Gardner, J. F., J. Bacteriol., 184:5200-5203 (2002)), a method of using a plasmid containing a temperature sensitive replication origin, a method of using a plasmid capable of conjugative transfer, a method of using a suicide vector not having replication origin which functions in a host (U.S. Pat. No. 6,303,383, Japanese Patent Laid-open (Kokai) No. 05-007491), and so forth.

The modification for reducing the activity of a protein can also be attained by, for example, a mutagenesis treatment. Examples of the mutagenesis treatment include usual mutagenesis treatments such as irradiation of X-ray or ultraviolet radiation and mutagenesis treatment with a mutation agent such as N-methyl-N'-nitro-N-nitrosoguanidine (MNNG), ethyl methanesulfonate (EMS), and methyl methanesulfonate (MMS).

Reduction of the activity of a target protein can be confirmed by measuring the activity of the protein. Specifically, the activity of a protein can be decreased to, for example, 50% or less, 20% or less, 10% or less, 5% or less, or even 0%, of that observed in a non-modified strain.

Reduction of expression of a target gene can be confirmed by confirming reduction of transcription amount of the gene or reduction of amount of the target protein expressed from the gene.

Reduction of the transcription amount of a target gene can be confirmed by comparing the amount of mRNA transcribed from the gene with that observed in a non-modified strain. Examples of the method for measuring the amount of mRNA include Northern hybridization, RT-PCR, and so forth (Molecular Cloning, Cold spring Harbor Laboratory Press, Cold Spring Harbor (USA), 2001). The amount of mRNA can be decreased to, for example, 50% or less, 20% or less, 10% or less, 5% or less, or 0%, of that observed in a non-modified strain.

The decrease in the amount of a target protein can be confirmed by Western blotting using antibodies (Molecular Cloning, Cold Spring Harbor Laboratory Press, Cold Spring Harbor (USA) 2001). The amount of the protein can be decreased to, for example, 50% or less, 20% or less, 10% or less, 5% or less, or 0%, of that observed in a non-modified strain.

Disruption of a target gene can be confirmed by determining the nucleotide sequence of a part or all of the gene, restriction enzyme map, full length of the gene, or the like depending on the means used for the disruption.

The coryneform bacterium having an ability to produce a heterologous protein by secretory production can be obtained by introducing the genetic construct used for the present invention into such a coryneform bacterium as mentioned above so that the construct is harbored by the bacterium.

It is known that a secretory protein is generally translated as a preprotein (also referred to as prepeptide) or a preproprotein (also referred to as prepropeptide), and then becomes a mature protein through processing. Specifically, a secretory protein is generally translated as a preprotein or preproprotein, then a signal peptide as the pre-moiety is cleaved with a protease (generally called signal peptidase), and the secretory protein is thereby converted into a mature protein or proprotein. As for the proprotein, the pro-moiety thereof is further cleaved by a protease, and the proprotein thereby becomes a mature protein. Therefore, a signal peptide is used for the secretory production of a heterologous protein. A preprotein and a preproprotein of a secretory protein may be collectively referred to as "secretory protein precursor". The "signal peptide" (also referred to as "signal sequence") can refer to an amino acid sequence present at the N-terminus of a secretory protein precursor, and which does not usually exist in the natural mature protein.

The genetic construct can include a promoter sequence that functions in a coryneform bacterium, a nucleic acid sequence coding for a signal peptide that functions in the coryneform bacterium, which is ligated downstream from the promoter sequence, and a nucleic acid sequence coding for a fusion protein of an amino acid sequence including Gln-Glu-Thr and a heterologous protein, which is ligated downstream from the nucleic acid sequence coding for the signal peptide. The nucleic acid sequence coding for a signal peptide may be ligated downstream from the promoter sequence so that the signal peptide is expressed under the control of the promoter. The nucleic acid sequence coding for the fusion protein may be ligated downstream from the nucleic acid sequence coding for the signal peptide so that the fusion protein is expressed as a further fusion protein with the signal peptide. The genetic construct can also include a control sequence, such as an operator, terminator, etc., which is effective for expression of the heterologous protein gene in a coryneform bacterium at such an appropriate position that it can function.

The promoter is not particularly limited so long as a promoter that functions in a coryneform bacterium is chosen, and it may be a promoter derived from a coryneform bacterium, or a heterologous promoter. The "promoter that functions in a coryneform bacterium" can refer to a promoter that possesses promoter activity in a coryneform bacterium. Specific examples of the heterologous promoter include, for example, promoters derived from *E. coli* such as tac promoter, lac promoter, trp promoter, and araBAD promoter. Among these, potent promoters such as tac promoter are preferred, and inducible promoters such as araBAD promoter are also preferred.

Examples of the promoter derived from a coryneform bacterium can include, for example, promoters of the genes of the cell surface layer proteins PS1, PS2 (also referred to as CspB), and SlpA (also referred to as CspA), and promoters of various amino acid biosynthesis system genes. Specific examples of the promoters of various amino acid biosynthesis system genes can include, for example, promoters of the glutamate dehydrogenase gene of the glutamic acid biosynthesis system, the glutamine synthetase gene of the glutamine synthesis system, the aspartokinase gene of the lysine biosynthesis system, the homoserine dehydrogenase gene of the threonine biosynthesis system, the acetohydroxy acid synthetase gene of the isoleucine and valine biosynthesis system, 2-isopropylmalate synthetase gene of the leucine biosynthesis system, the glutamate kinase gene of the proline and arginine biosynthesis system, the phosphoribosyl-ATP pyrophosphorylase gene of the histidine biosynthesis system, the deoxyarabinoheptulonate phosphate (DAHP) synthetase gene of the aromatic amino acid biosynthesis systems such as those for tryptophan, tyrosine, and phenylalanine, the phosphoribosyl pyrophosphate (PRPP) amidotransferase gene of the nucleic acid biosynthesis systems such as those for inosinic acid and guanylic acid, the inosinic acid dehydrogenase gene, and the guanylic acid synthetase gene.

A high activity version of a known promoter may be obtained by using various reporter genes. For example, by making the −35 and −10 regions in a promoter region closer to a consensus sequence, activity of the promoter can be enhanced (International Patent Publication WO00/18935). Examples of the method for evaluating strength of a promoter and strong promoters are described in the paper of Goldstein et al. (Prokaryotic promoters in biotechnology, Biotechnol. Annu. Rev., 1, 105-128 (1995)) and so forth. Further, it is known that substitution, insertion, or deletion of several nucleotides in a spacer region between the ribosome-binding site (RBS) and the start codon, especially in a sequence immediately upstream of the start codon (5'-UTR), significantly affects stability and translation efficiency of mRNA, and these sequences can also be modified.

The signal peptide is not particularly limited so long as a signal peptide that functions in a coryneform bacterium is chosen, and it may be a signal peptide derived from a coryneform bacterium, or it may be a heterologous signal peptide. The "signal peptide that functions in a coryneform bacterium" can refer to a peptide that when it is ligated to the N-terminus of an objective protein, allows the coryneform bacterium to secrete the protein. The signal peptide can be a signal peptide of a secretory protein of the coryneform bacterium as the host, or a signal peptide of a cell surface layer protein of the coryneform bacterium. Examples of the cell surface layer protein of coryneform bacteria include PS1 and PS2 (CspB) derived from *C. glutamicum* (Japanese Patent Laid-open (Kohyo) No. 6-502548), and SlpA (CspA) derived from *C. ammoniagenes* (*C. stationis*) (Japanese Patent Laid-open (Kokai) No. 10-108675). The amino acid sequence of the signal peptide of PS1 is shown in SEQ ID NO: 91, the amino acid sequence of the signal peptide of PS2 (CspB) is shown in SEQ ID NO: 92, and the amino acid sequence of the signal peptide of SlpA (CspA) is shown in SEQ ID NO: 93. Moreover, U.S. Pat. No. 4,965,197 describes signal peptides for DNases derived from coryneform bacteria, and such signal peptides can also be used.

Although signal peptides from different biological species often have homologous sequences, a signal peptide that exhibits a secretory function in a certain biological species does not necessarily exhibit a secretory function in another biological species. Therefore, when a heterologous signal peptide is used, a signal peptide that functions in a coryneform bacterium can be appropriately chosen. Whether a certain signal peptide functions in a coryneform bacterium can be confirmed by, for example, expressing the objective protein as a fusion protein with that signal peptide, and confirming whether the protein is secreted or not.

The signal sequence is generally cleaved by a signal peptidase, when the translation product is secreted out of the cell. As a gene coding for a signal peptide, although a naturally occurring gene may be used as it is, it may be modified so that it has the optimal codons according to codon frequencies in the chosen host.

In the genetic construct, a nucleic acid sequence coding for an amino acid sequence including Gln-Glu-Thr is inserted between the nucleic acid sequence coding for a signal peptide and the nucleic acid sequence coding for the heterologous protein. In the present invention, the amino acid sequence including Gln-Glu-Thr is also referred to as an "insertion sequence".

The insertion sequence is not particularly limited so long as it includes at least the tripeptide Gln-Glu-Thr. Further, the position of Gln-Glu-Thr in the insertion sequence is not particularly limited; however, it is preferred that the first three amino acid residues at the N-terminus of the insertion sequence are Gln-Glu-Thr. That is, it is preferred that, in the expressed heterologous protein, Gln-Glu-Thr is immediately downstream of the signal peptide.

The insertion sequence can be a sequence consisting of 3 or more amino acid residues from the N-terminus of the mature protein of the cell surface layer protein CspB of a coryneform bacterium (henceforth also referred to as "mature CspB" or "CspB mature protein"). The "sequence consisting of 3 or more amino acid residues from the N-terminus" can mean an amino acid sequence from the amino acid residue at position 1 of the N-terminus to an amino acid residue at position 3 or a more remote position.

Specific examples of CspB include, for example, CspB of *C. glutamicum* ATCC 13869. CspB is synonymous with PS2. The nucleotide sequence of the cspB gene of *C. glutamicum* ATCC 13869 is shown in SEQ ID NO: 94, and the amino acid sequence of the CspB protein is shown in SEQ ID NO: 95. In the amino acid sequence shown in SEQ ID NO: 95, the amino acid residues at positions 1 to 30 correspond to the signal peptide, and the amino acid residues at positions 31 to 469 correspond to the CspB mature protein. The amino acid sequence of the CspB mature protein of *C. glutamicum* ATCC 13869, without the 30 amino acid residues that make up the signal peptide, is shown in SEQ ID NO: 96. The N-terminus of the CspB mature protein refers to the part of the CspB mature protein other than the 29 amino acid residues on the C-terminal side, that function as a hydrophobic region. In the mature CspB of *C. glutamicum* ATCC 13869, the amino acid residues of positions 1 to 3 of the N-terminus correspond to Gln-Glu-Thr. The part of the nucleotide sequences of the cspB gene coding for the part of the amino acid sequence of the mature CspB that include the insertion sequence can be used.

Since the nucleotide sequence of the cspB gene may differ depending on the species or strain from which the coryneform bacterium is derived, the cspB gene can be a variant of the aforementioned nucleotide sequence, so long as the secretory production amount of the heterologous protein can be increased with the insertion sequence of the present invention. The variant of the cspB gene can include a homologue of the gene. Homologues of the cspB gene can be easily obtained from public databases by BLAST search or FASTA search using, for example, the aforementioned cspB gene of *C. glutamicum* ATCC 13869 (SEQ ID NO: 94) as a query sequence, and can also be obtained by PCR using a chromosome of a coryneform bacterium as a template and oligonucleotides prepared on the basis of a known gene sequence such as those mentioned above as primers.

For example, amino acid sequences of CspB homologues have been reported for 28 strains of *C. glutamicum* (J. Biotechnol., 112, 177-193 (2004)). In comparison of the N-terminal amino acid sequences of the CspB homologues derived from these 28 strains, it can be seen that the signal sequence of 30 amino acid residues and the N-terminal 3 amino acid residues (Gln-Glu-Thr) of the mature protein were completely conserved. Further, in comparing up to 6 amino acids at the N-termini of the mature proteins of the CspB homologues, the amino acid sequences were classified into 5 patterns, i.e., Gln-Glu-Thr-Asn-Pro-Thr (henceforth also represented as QETNPT (SEQ ID NO: 97)), Gln-Glu-Thr-Gly-Thr-Tyr (henceforth also represented as QETGTY (SEQ ID NO: 98)), Gln-Glu-Thr-Thr-Val-Thr (henceforth also represented as QETTVT (SEQ ID NO: 99)), Gln-Glu-Thr-Pro-Val-Thr (henceforth also represented as QETPVT (SEQ ID NO: 100)), and Gln-Glu-Thr-Ala-Val-Thr (henceforth also represented as QETAVT (SEQ ID NO: 101)). These 28 strains of *C. glutamicum* and the GenBank accession numbers of the cspB gene homologues in NCBI database are exemplified below (the GenBank accession numbers are shown in the parentheses).

*C. glutamicum* ATCC13058 (AY524990)
*C. glutamicum* ATCC13744 (AY524991)
*C. glutamicum* ATCC13745 (AY524992)
*C. glutamicum* ATCC14017 (AY524993)
*C. glutamicum* ATCC14020 (AY525009)
*C. glutamicum* ATCC14067 (AY524994)
*C. glutamicum* ATCC14068 (AY525010)
*C. glutamicum* ATCC14747 (AY525011)
*C. glutamicum* ATCC14751 (AY524995)
*C. glutamicum* ATCC14752 (AY524996)
*C. glutamicum* ATCC14915 (AY524997)
*C. glutamicum* ATCC15243 (AY524998)
*C. glutamicum* ATCC15354 (AY524999)
*C. glutamicum* ATCC17965 (AY525000)
*C. glutamicum* ATCC17966 (AY525001)
*C. glutamicum* ATCC19223 (AY525002)
*C. glutamicum* ATCC19240 (AY525012)
*C. glutamicum* ATCC21341 (AY525003)
*C. glutamicum* ATCC21645 (AY525004)
*C. glutamicum* ATCC31808 (AY525013)
*C. glutamicum* ATCC31830 (AY525007)
*C. glutamicum* ATCC31832 (AY525008)
*C. glutamicum* LP-6 (AY525014)
*C. glutamicum* DSM20137 (AY525015)
*C. glutamicum* DSM20598 (AY525016)
*C. glutamicum* DSM46307 (AY525017)
*C. glutamicum* 22220 (AY525005)
*C. glutamicum* 22243 (AY525006)

The cspB gene can be a gene coding for a protein having one of the aforementioned amino acid sequences, and which may include substitution, deletion, insertion, or addition of one or several amino acid residues at one or several positions, so long as the secretory production amount of the heterologous protein can be increased with the insertion sequence of the present invention. Although the number of "one or several" may differ depending on the position in the three-dimensional structure of the protein or types of amino acid residues, specifically, it can be 1 to 20, 1 to 10, or 1 to 5, for example.

The aforementioned substitution, deletion, insertion, or addition of one or several amino acid residues can be a conservative mutation that maintains the normal function of the protein. Typical examples of conservative mutations are conservative substitutions. The conservative substitution is a mutation wherein substitution takes place mutually among Phe, Trp, and Tyr, if the substitution site is an aromatic amino acid; among Leu, Ile, and Val, if it is a hydrophobic amino acid; between Gln and Asn, if it is a polar amino acid; among Lys, Arg, and His, if it is a basic amino acid; between Asp and Glu, if it is an acidic amino acid; and between Ser and Thr, if it is an amino acid having a hydroxyl group. Examples of substitutions considered as conservative substitutions include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Be, Met, Val, or Phe for Leu, substitution of Asn, Glu, Gln, His, or Arg for Lys, substitution of Be, Leu, Val, or Phe for Met, substitution of Trp, Tyr, Met, Be, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Further, such substitution, deletion, insertion, addition, inversion or the like of amino acid residues as mentioned above can include a naturally occurring mutation due to an individual difference, or a difference of species of a bacterium from which the gene is derived (mutant or variant).

Furthermore, the gene having such a conservative mutation as mentioned above may be a gene coding for a protein showing a homology of 80% or more, 90% or more, 95% or more, 97% or more, or 99% or more, to the total encoded amino acid sequence, so long as the secretory production amount of the heterologous protein can be increased with the insertion sequence of the present invention. In addition, "homology" can mean "identity".

Moreover, the cspB gene can be a DNA that is able to hybridize with a probe that can be prepared from a known gene sequence, such as a sequence complementary to a part of, or the entire aforementioned nucleotide sequence, under stringent conditions, so long as the secretory production amount of the heterologous protein can be increased with the insertion sequence of the present invention. The "stringent conditions" can refer to conditions under which a so-called specific hybrid is formed, and a non-specific hybrid is not formed. Examples of the stringent conditions can include those under which highly homologous DNAs hybridize to each other, for example, DNAs not less than 80% homologous, not less than 90% homologous, not less than 95% homologous, not less than 97% homologous, or not less than 99% homologous, hybridize to each other, and DNAs less homologous than the above do not hybridize to each other, or conditions of washing of typical Southern hybridization, i.e., conditions of washing once, or 2 or 3 times, at a salt concentration and temperature corresponding to 1×SSC, 0.1% SDS at 60° C., 0.1×SSC, 0.1% SDS at 60° C., or 0.1×SSC, 0.1% SDS at 68° C.

The probe used for the aforementioned hybridization can be a part of a sequence that is complementary to the gene as described above. Such a probe can be prepared by PCR using oligonucleotides prepared on the basis of a known gene sequence as primers and a DNA fragment containing the nucleotide sequence as a template. For example, when a DNA fragment having a length of about 300 bp is used as the probe, the washing conditions of the hybridization may be, for example, 50° C., 2×SSC and 0.1% SDS.

Further, although a naturally occurring cspB gene can be used as it is, a cspB gene in which an arbitrary codon is replaced with an equivalent codon may also be used. For example, the cspB gene may be modified so that it has optimal codons according to codon frequencies in the chosen host.

The above descriptions concerning variants of the genes and proteins can also be applied *mutatis mutandis* to arbitrary proteins, such as other cell surface layer proteins and heterologous proteins to be produced by secretory production in the present invention and genes coding for them.

The expression "secretory production amount of a heterologous protein can be increased with the insertion sequence of the present invention" can mean, but is not particularly limited to, so long as the secretory production amount of the heterologous protein increases compared with that observed without the insertion sequence, for example, that the heterologous protein is produced by secretory production in an amount larger than that observed for a non-modified strain by 10% or more, 20% or more, 30% or more, or 100% or more, or even 100% or more, 300% or more, 500% or more, or 1000% or more, in terms of the accumulation amount in the medium and/or the cell surface layer. In addition, the expression "secretory production amount of a heterologous protein can be increased with the insertion sequence of the present invention" can also mean that whereas the heterologous protein cannot be detected when a non-concentrated culture supernatant of a strain containing the genetic construct without the insertion sequence of the present invention is applied to SDS-PAGE and stained with CBB, the heterologous protein can be detected when a non-concentrated culture supernatant of a strain containing the genetic construct with the insertion sequence of the present invention is applied to SDS-PAGE and stained with CBB. Whether the secretory production amount of a heterologous protein can be increased with the insertion sequence of the present invention or not can be confirmed by introducing a genetic construct containing the insertion sequence of the present invention into a strain belonging to coryneform bacteria, quantifying the secretory production amount of the heterologous protein observed when the strain is cultured in a medium, and comparing the quantified amount with the secretory production amount of the heterologous protein observed when a control strain containing the genetic construct without the insertion sequence of the present invention is cultured in the medium.

The "amino acid residue at position X of the mature CspB" can mean the amino acid residue that corresponds to position X in SEQ ID NO: 96. The term "position X" in an amino acid sequence can mean the X-th position from the N-terminus of the amino acid sequence, and the amino acid residue at the N-terminus is the amino acid residue at position 1. That is, the aforementioned positions of amino acid residues represent relative positions, and the positions may shift due to deletion, insertion, addition, or the like of amino acid residue(s). For example, "the amino acid residue at position 50 of the mature CspB" can mean the amino acid residue that corresponds to position 50 in SEQ ID NO: 96, and when one amino acid residue is deleted on the N-terminal side of position 50, the 49th amino acid residue from the N-terminus is "the amino acid residue at position 50 of the mature CspB". Further, when one amino acid residue is inserted on the N-terminal side of position 50, the 51st amino acid residue from the N-terminus is "the amino acid residue of position 50 of the mature CspB". That is, for example, "an amino acid sequence consisting of Gln-Glu-Thr fused with the amino acid residues at position 4 to 50 of the mature CspB" can mean an amino acid sequence consisting of Gln-Glu-Thr fused with the amino acid residues that correspond to position 4 to 50 of SEQ ID NO: 96.

The insertion sequence used for the present invention can be an amino acid sequence starting from the amino acid residue at position 1 to an amino acid residue at any of the positions from 3 to 50 of the mature CspB. The insertion sequence used for the present invention can be an amino acid sequence starting from the amino acid residue at position 1 to an amino acid residue at any of the positions from 3 to 8, 17, and 50 of the mature CspB. The insertion sequence can be an amino acid sequence starting from the amino acid residue at position 1 to an amino acid residue at any of the positions from 4, 6, 17 and 50.

The length of the insertion sequence can be 3 to 50 amino acid residues, 3 to 8, 17, or 50 amino acid residues, or 4, 6, 17, or 50 amino acid residues.

When the first to third amino acid residues from the N-terminus of the insertion sequence are Gln-Glu-Thr, and the insertion sequence has a length of at least 4, 5, or 6 amino acid residues, the fourth amino acid residue from the N-terminus of the insertion sequence can be Asn, Gly, Thr, Pro, or Ala, the fifth amino acid residue can be Pro, Thr, or Val, and the sixth amino acid residue can be Thr or Tyr. When one or more amino acid residues are present on the N-terminal side of Gln-Glu-Thr in the insertion sequence, the aforementioned fourth amino acid residue shall be the amino acid residue next to the amino acid residue Thr of Gln-Glu-Thr, and the aforementioned fifth and sixth amino acid residues are also similarly defined.

The insertion sequence can be an amino acid sequence such as one of the following, for example:

```
(A) Gln-Glu-Thr (SEQ ID NO: 102)
(B) Gln-Glu-Thr-Xaa1

(SEQ ID NO: 103)
(C) Gln-Glu-Thr-Xaa1-Xaa2

(SEQ ID NO: 104)
(D) Gln-Glu-Thr-Xaa1-Xaa2-Xaa3
```

(E) the amino acid sequence of Gln-Glu-Thr fused with the amino acid residues at positions 4 to 7 of mature CspB,
(F) the amino acid sequence of Gln-Glu-Thr fused with the amino acid residues at positions 4 to 8 of mature CspB,
(G) the amino acid sequence of Gln-Glu-Thr fused with the amino acid residues at positions 4 to 17 of mature CspB,
(H) the amino acid sequence of Gln-Glu-Thr fused with the amino acid residues at positions 4 to 50 of mature CspB.

In the above amino acid sequences (A) to (H), Xaa1 is Asn, Gly, Thr, Pro, or Ala; Xaa2 is Pro, Thr, or Val; and Xaa3 is Thr or Tyr. As for the amino acid sequences (A) to (H), "Gln-Glu-Thr fused with the amino acid residues at positions 4 to X of mature CspB" can mean that the amino acid residues at positions 4 to X at the N-terminus of mature CspB is fused to Thr of Gln-Glu-Thr. The first to third amino acid residues of the N-terminus of mature CspB are usually Gln-Glu-Thr, and in such a case, "an amino acid sequence of Gln-Glu-Thr fused with the amino acid residues at positions 4 to X of mature CspB" is synonymous with an amino acid sequence of the amino acid residues at position 1 to X of the mature CspB.

Further, specifically, the insertion sequence used for the present invention can be an amino acid sequence such as the following, for example, Gln-Glu-Thr-Asn-Pro-Thr (SEQ ID NO: 97), Gln-Glu-Thr-Gly-Thr-Tyr (SEQ ID NO: 98), Gln-Glu-Thr-Thr-Val-Thr (SEQ ID NO: 99), Gln-Glu-Thr-Pro-Val-Thr (SEQ ID NO: 100), or Gln-Glu-Thr-Ala-Val-Thr (SEQ ID NO: 101).

As described above, the heterologous protein to be produced by secretory production according to the method of the present invention includes, but is not particularly limited to, any protein, and includes, for example, proteins derived from microorganisms, plants, animals, and viruses, as well as artificially designed proteins.

Examples of the heterologous protein to be produced by secretory production according to the method of the present invention can include, for example, physiologically active proteins, receptor proteins, antigenic proteins for use as vaccines, and enzymes. Examples of enzymes can include, for example, transglutaminase, protease, endopeptidase, exopeptidase, aminopeptidase, carboxypeptidase, collagenase, chitinase, and so forth.

Examples of the physiologically active proteins can include, for example, growth factors, hormones, cytokines, and antibody-related molecules.

Specific examples of the growth factors can include, for example, epidermal growth factor (EGF), insulin-like growth factor-1 (IGF-1), transforming growth factor (TGF), nerve growth factor (NGF), brain-derived neurotrophic factor (BDNF), vesicular endothelial growth factor (VEGF), granulocyte-colony stimulating factor (G-CSF), granulocyte-macrophage-colony stimulating factor (GM-CSF), platelet-derived growth factor (PDGF), erythropoietin (EPO), thrombopoietin (TPO), acidic fibroblast growth factor (aFGF or FGF1), basic fibroblast growth factor (bFGF or FGF2), keratinocyte growth factor (KGF-1 or FGF7, and, KGF-2 or FGF10), and hepatocyte growth factor (HGF).

Specific examples of the hormones can include, for example, insulin, glucagon, somatostatin, human growth hormone (hGH), parathyroid hormone (PTH), and calcitonin.

Specific examples of the cytokines can include, for example, interleukins, interferons, and tumor necrosis factors (TNFs).

The growth factors, hormones, and cytokines may not be strictly distinguished from one another. For example, a physiologically active protein may be a protein such as a growth factor, hormone, or cytokine, or can be a protein that is considered one or more of these types of proteins, such as, for example, a growth factor and a hormone.

Further, a physiologically active protein may be an intact protein, or may be a part of a protein. Examples of a part of a protein can include, for example, a part having physiological activity. Specific examples of a part having physiological activity can include, for example, Teriparatide, a physiologically active peptide consisting of the N-terminal 34 amino acid residues of parathyroid hormone (PTH).

Specific examples of the antibody-related molecules can include, for example, complete antibodies, Fab, F(ab'), $F(ab')_2$, Fc, a dimer of the heavy chain (H chain) and the light chain (L chain), Fc-fusion proteins, the heavy chain (H chain), and the light chain (L chain).

The receptor proteins are not particularly limited. A receptor protein may be, for example, a receptor protein for any of physiologically active proteins and other physiologically active substances. Examples of the other physiologically active substances include, for example, neurotransmitters such as dopamine. Further, a receptor protein may be an orphan receptor of which the corresponding ligand is not known.

The antigen proteins for use as vaccines are not particularly limited, so long as they are proteins that can induce an immune response. An antigen protein can be appropriately selected depending on the intended object of the immune response.

Genes coding for these proteins can be modified according to the chosen host and for obtaining a desired activity. For example, the genes coding for these proteins may be modified so that the proteins include addition, deletion, substitution, or the like of one or several amino acid residues. The above descriptions concerning variants of the CspB protein and the cspB gene can also be applied *mutatis mutandis* to the heterologous protein to be produced by secretory production by the method of the present invention and the gene coding for it. Further, in the genes coding for these proteins, an arbitrary codon may be replaced with an equivalent codon thereof. For example, in the genes coding for these proteins, codons may be optimized as required according to codon frequencies observed in the chosen host.

The genetic construct can further include a nucleic acid sequence coding for an amino acid sequence used for enzymatic digestion between the nucleic acid sequence coding for the amino acid sequence including Gln-Glu-Thr and the nucleic acid sequence coding for the heterologous protein. If the amino acid sequence used for enzymatic digestion is inserted in the fusion protein, the expressed fusion protein can be enzymatically digested to obtain the objective heterologous protein.

The amino acid sequence used for enzymatic digestion is not particularly limited so long as it is a sequence that can be recognized and digested by an enzyme that hydrolyzes a peptide bond, and an appropriate sequence can be chosen according to the amino acid sequence of the objective heterologous protein. The nucleic acid sequence coding for the amino acid sequence used for enzymatic digestion may be designed on the basis of that amino acid sequence, and for example, optimal codons can be used according to codon frequencies observed in the chosen host.

The amino acid sequence used for enzymatic digestion can be a recognition sequence of a protease showing high substrate specificity. Specific examples of such an amino acid sequence include, for example, a recognition sequence of factor Xa protease and a recognition sequence of proTEV protease. The factor Xa protease and the proTEV protease recognize the amino acid sequence of Ile-Glu-Gly-Arg (=IEGR, SEQ ID NO: 105) and the amino acid sequence of Glu-Asn-Leu-Tyr-Phe-Gln (=ENLYFQ, SEQ ID NO: 106) in a protein, respectively, to specifically digest the protein at the C-terminal side of each recognition sequence.

The N-terminal region of the heterologous protein eventually obtained by the method of the present invention may be the same as that of the natural protein, or may not be the same as that of the natural protein. For example, the N-terminal region of the eventually obtained heterologous protein may have an amino acid sequence including Gln-Glu-Thr, or an amino acid sequence including Gln-Glu-Thr and the aforementioned amino acid sequence used for enzymatic digestion, or may not have any of these sequences. Further, for example, the N-terminal region of the eventually obtained heterologous protein may be that of the natural protein including addition or deletion of one or several amino acid residues. Although the number of the "one or several" amino acid residues may differ depending on the full length or structure of the objective heterologous protein, specifically, it can be 1 to 20, 1 to 10, or 1 to 5, for example.

Further, the heterologous protein that is produced by secretory production may include a pro-structure moiety (proprotein), and the heterologous protein which is eventually obtained may or may not be the proprotein. That is, the proprotein may be further processed into the mature protein by cleavage of the pro-structure moiety. The cleavage can be attained with, for example, a protease. When a protease is used, generally, the proprotein can be cleaved at a position substantially the same as that of the natural protein, or even at exactly the same position as that of the natural protein so that the same mature protein as the natural mature protein is obtained, in view of the activity of the eventually obtained protein. Therefore, generally, a specific protease that cleaves the proprotein at a position so that the same protein as the naturally occurring mature protein is generated is most preferred. However, the N-terminal region of the obtained heterologous protein does not have to be the same as that of the natural protein as described above. For example, depending on type, purpose of use etc. of the produced heterologous protein, a protein having an N-terminus longer or shorter by one to several amino acid residues compared with the natural protein may have more appropriate activity. Proteases usable in the present invention include, for example, commercially available proteases such as Dispase (produced by Boehringer Mannheim) as well as those obtainable from culture broth of a microorganism such as culture broth of actinomycetes. Such proteases may be used in an un-purified state, or may be purified to an appropriate purity as required. When the pro-structure moiety is cleaved to obtain a mature protein, the inserted amino acid sequence that includes Gln-Glu-Thr is removed together with the pro-structure moiety, and therefore the objective protein can be obtained without providing an amino acid sequence used for enzymatic digestion downstream from the amino acid sequence that includes Gln-Glu-Thr.

The method for introducing the genetic construct used for the present invention into the coryneform bacterium is not particularly limited. In the bacterium of the present invention, the genetic construct may be present on a vector that autonomously replicates out of the chromosome such as a plasmid, or may be incorporated into the chromosome. In addition, for constructing the bacterium of the present invention, introduction of the genetic structure, impartation or enhancement of the ability to produce a protein by secretory production, and other modifications can be performed in an arbitrary order.

The genetic construct used for the present invention can be introduced into a host by using, for example, a vector that contains the genetic construct. The vector is not particularly limited so long as it is able to be autonomously replicated in a coryneform bacterium, and may be, for example, a vector derived from a bacterial plasmid, a vector derived from a yeast plasmid, a vector derived from a bacteriophage, cosmid, phagemid, or the like. As the vector, a plasmid derived from a coryneform bacterium is an example. Specific examples of vector autonomously replicable in coryneform bacteria include pHM1519 (Agric. Biol. Chem., 48, 2901-2903 (1984)); pAM330 (Agric. Biol. Chem., 48, 2901-2903 (1984)); plasmids obtained by improving these and having a drug resistance gene; plasmid pCRY30 described in Japanese Patent Laid-open (Kokai) No. 3-210184; plasmids pCRY21, pCRY2KE, pCRY2KX, pCRY31, pCRY3KE, and pCRY3KX described in Japanese Patent Laid-open (Kokai) No. 2-72876 and U.S. Pat. No. 5,185,262; plasmids pCRY2 and pCRY3 described in Japanese Patent Laid-open (Kokai) No. 1-191686; pAJ655, pAJ611, and pAJ1844 described in Japanese Patent Laid-open (Kokai) No. 58-192900; pCG1 described in Japanese Patent Laid-open (Kokai) No. 57-134500; pCG2 described in Japanese Patent Laid-open (Kokai) No. 58-35197; pCG4 and pCG11 described in Japanese Patent Laid-open (Kokai) No. 57-183799; and so forth.

Further, an artificial transposon and so forth can also be used. When a transposon is used, a heterologous protein gene is introduced into a chromosome by homologous recombination or translocation ability of the transposon itself. Other examples of the introduction method utilizing homologous recombination include, for example, methods utilizing a linear DNA, a plasmid having a temperature sensitive replication origin, a plasmid capable of conjugative transfer, a suicide vector not having a replication origin that functions in a host, and so forth. In addition, when a gene encoding the heterologous protein is introduced into a chromosome, so long as the genetic construct used for the present invention is present on the chromosome, the promoter sequence, the nucleic acid sequence coding for a signal peptide, and/or the nucleic acid sequence coding for an amino acid sequence that includes Gln-Glu-Thr can be native to the host chromosome. Specifically, for example, by using a promoter sequence ligated to a nucleic acid sequence encoding the signal peptide, both of which are native to the host chromosome, and replacing only the gene ligated downstream from the signal peptide nucleic acid sequence with a nucleic acid sequence coding for a fusion protein of an amino acid sequence including Gln-Glu-Thr and a heterologous protein, the genetic construct used for the present invention is present on the chromosome.

Further, when two or more kinds of proteins are expressed, it is sufficient that the genetic constructs for secretory expression of the proteins are harbored by the bacterium of the present invention so that secretory expression of the objective heterologous proteins can be attained. Specifically, for example, all the genetic constructs for secretory expression of the proteins may be harbored on a single expression vector, or harbored on the chromosome. Alternatively, the genetic constructs for secretory expression of the proteins may be separately harbored on a plurality of expression vectors, or may be separately harbored on one or more expression vectors and the chromosome. The phrase "two or more kinds of proteins are expressed" can refer to, for example, when two or more kinds of heterologous proteins are produced by secretory production, or when a hetero-multimeric protein is produced by secretory production.

The method for introducing the genetic construct used for the present invention into the coryneform bacterium is not particularly limited, and a generally used method, for example, the protoplast method (Gene, 39, 281-286 (1985)), the electroporation method (Bio/Technology, 7, 1067-1070 (1989)), and so forth can be used.

By culturing the bacterium of the present invention obtained as described above to express a heterologous protein, a large amount of the heterologous protein secreted out of the cells is obtained.

The bacterium of the present invention can be cultured according to a usually used method and conditions. For example, the bacterium of the present invention can be cultured in a usual medium containing a carbon source, a nitrogen source, and inorganic ions. In order to obtain still higher proliferation, organic micronutrients such as vitamins and amino acids can also be added as required.

As the carbon source, carbohydrates such as glucose and sucrose, organic acids such as acetic acid, alcohols, and others can be used. As the nitrogen source, ammonia gas, aqueous ammonia, ammonium salts, and others can be used. As the inorganic ions, calcium ions, magnesium ions, phosphate ions, potassium ions, iron ions, and so forth are appropriately used as required. The culture can be performed within appropriate ranges of pH 5.0 to 8.5 and 15 to 37° C. under aerobic conditions for 1 to 7 days. Further, the culture conditions for L-amino acid production by coryneform bacteria and other conditions described for the methods for producing a protein using a signal peptide of the Sec type or the Tat type can be used (refer to WO01/23591 and WO2005/103278). Further, when an inducible promoter is used for expression of the heterologous protein, a promoter-inducing agent can be also added to the culture medium. By culturing the bacterium of the present invention under such conditions, a large amount of the objective protein is produced in cells and efficiently secreted out of the cells. In addition, according to the method of the present invention, the produced heterologous protein is secreted out of the cells, and therefore a protein that is generally lethal if it is accumulated in a large amount in cells of microorganisms, such as transglutaminases, can also be continuously produced without lethal effect.

The protein secreted in the medium according to the method of the present invention can be separated and purified from the medium after the culture by a method well known to those skilled in the art. For example, after the cells are removed by centrifugation or the like, the protein can be separated and purified by a known appropriate method such as salting out, ethanol precipitation, ultrafiltration, gel filtration chromatography, ion exchange column chromatography, affinity chromatography, medium or high pressure liquid chromatography, reverse phase chromatography, and hydrophobic chromatography, or a combination of these. Further, in a certain case, culture or culture supernatant may be used as it is. The protein secreted in the cell surface layer according to the method of the present invention can also be separated and purified in the same manner as that for the case when the protein is secreted in the medium, after solubilizing it by a method well known to those skilled in the art such as elevation of salt concentration and use of a surfactant. Further, in a certain case, the protein secreted in the cell surface layer may be used as, for example, an immobilized enzyme, without solubilizing it.

Secretory production of the objective heterologous protein can be confirmed by performing SDS-PAGE for the culture supernatant and/or a fraction containing the cell surface layer as a sample, and confirming the molecular weight of the separated protein band. Secretory production of the objective heterologous protein can also be confirmed by performing Western blotting using antibodies for the culture supernatant and/or a fraction containing the cell surface layer as a sample (Molecular Cloning, Cold spring Harbor Laboratory Press, Cold Spring Harbor (USA), 2001). Secretory production of the objective heterologous protein can also be confirmed by determining the N-terminal amino acid sequence of the objective protein using a protein sequencer. Further, secretory production of the objective heterologous protein can also be confirmed by determining the mass of the objective protein using a mass spectrometer. Furthermore, when the objective heterologous protein is an enzyme or a protein having a certain measurable physiological activity, secretory production of the objective heterologous protein can be confirmed by measuring enzymatic activity or the physiological activity of the objective protein in the culture supernatant and/or a fraction containing the cell surface layer as a sample.

When the residue immediately after the signal peptide is glutamine in the protein expressed from the genetic construct, the N-terminal amino acid residue of the protein obtained by cleavage of the signal peptide is a pyroglutamic acid formed by dehydration condensation of the original glutamine residue. That is, for example, the N-terminal amino acid residue of the secreted heterologous protein can be a pyroglutamic acid residue. It can be confirmed that the N-terminal amino acid residue of the objective heterologous protein is a pyroglutamic acid residue by determining the mass of the objective heterologous protein with a mass spectrometer, and confirming that the determined mass corresponds to the mass calculated by subtracting the mass of water molecule (=18) from the theoretical original mass. Further, when the N-terminal amino acid residue of the protein is a pyroglutamic acid residue, the Edman degradation reaction is blocked, and therefore the N-terminal amino acid sequence cannot be determined by using a protein sequencer. Therefore, it can also be confirmed that the N-terminal amino acid residue of the objective heterologous protein is a pyroglutamic acid residue on the basis of the fact that the N-terminal amino acid sequence of the objective heterologous protein cannot be directly determined even when using a protein sequencer, while the second and subsequent amino acid residues of the original N-terminal amino acid sequence can be determined by using a protein sequencer after pyroglutamate aminopeptidase is allowed to act on the objective heterologous protein. Furthermore, as a simplified method, it can also be confirmed that the N-terminal amino acid residue of the objective heterologous protein is a pyroglutamic acid residue on the basis of the fact that the N-terminal amino acid sequence of the objective heterologous protein cannot be directly determined even by using a protein sequencer.

EXAMPLES

The present invention will be further specifically explained with reference to the following non-limiting examples.

Example 1

Secretory Expression of Proinsulin Fused with 1, 2, 3, 4, 5, 6, 7, 8, 9, 10, 11, 12, 13, 14, 15, 17, 20, 50, 100, 150, 200, 250, 300, 350, 400, or 440 Amino Acid Residues from the N-terminus of Mature Cell Surface Layer Protein CspB of *Corynebacterium glutamicum* ATCC 13869

(1) Total Synthesis of Proinsulin Gene and Construction of Proinsulin Secretory Expression Plasmids Using Signal Sequence of Cell Surface Layer Protein CspB of *Corynebacterium glutamicum* ATCC 13869

The amino acid sequence of proinsulin (henceforth abbreviated as PIns) has already been reported (Genbank Accession No. NP_000198.1). In consideration of this sequence and the codon frequencies in *C. glutamicum*, DNAs shown in SEQ ID NOS: 1 to 8 were synthesized. The gene coding for PIns was amplified by PCR using these DNAs as the templates and DNAs shown in SEQ ID NOS: 9 and 10 as the primers to obtain a DNA fragment of about 0.3 kbp shown in SEQ ID NO: 11. This DNA fragment was inserted into a cloning vector pHSG398 (Takara Bio) at the SmaI site to obtain pHSG-PIns. The PIns gene region was amplified by PCR using the above pHSG-PIns as the template and the DNAs shown in SEQ ID NOS: 9 and 10 as the primers to obtain a PIns gene fragment of about 0.3 kbp.

The nucleotide sequence of the gene coding for CspB, which is a cell surface layer protein of *C. glutamicum*, has also already been determined (Non-patent document 8; Mol. Microbiol., 9, 97-109 (1993)). By referring to this sequence, the promoter region and the region coding for the signal peptide of CspB derived from the *C. glutamicum* ATCC 13869 strain were amplified by PCR using pPKPTG1 described in WO01/23591 as the template and the primers shown in SEQ ID NOS: 12 and SEQ ID NO: 13 to obtain a DNA fragment of about 0.7 kbp. The pPKPTG1 is a vector for secretory expression of pro-transglutaminase (transglutaminase having a pro-structure moiety), and contains the promoter of the cspB gene derived from the *C. glutamicum* ATCC 13869 strain, a DNA coding for the signal peptide 30 amino acid residues derived from the *C. glutamicum* ATCC 13869 strain and expressibly ligated downstream from the promoter, and a pro-transglutaminase gene derived from actinomycetes, *Streptoverticillium mobaraense*, ligated downstream from the DNA coding for the signal peptide so that the pro-transglutaminase is expressed as a fusion protein with the signal peptide.

Furthermore, by PCR using both the amplified DNA fragments (i.e. the PIns gene fragment and the fragment of the promoter region and the region coding for the signal peptide) as the template and the DNAs shown in SEQ ID NOS: 12 and 10 as the primers, a DNA fragment of about 0.9 kbp consisting of both the DNA fragments fused together was obtained. In the primers of SEQ ID NOS: 12 and 10, the recognition sequence for the restriction enzyme KpnI was designed. For PCR, Pyrobest DNA Polymerase (Takara Bio) was used, and the reaction conditions were according to the protocol recommended by the manufacturer. This DNA fragment was treated with the restriction enzyme KpnI, and then inserted into pPK4 described in Japanese Patent Laid-open (Kokai) No. 9-322774 at the KpnI site to obtain pPKPIns. By nucleotide sequencing of the insertion fragment, construction of the expected fusion gene was confirmed. The nucleotide sequencing was performed by using BigDye (registered trademark) Terminator v3.1 Cycle Sequencing Kit (Applied Biosystems) and 3130 Genetic Analyzer (Applied Biosystems).

(2) Construction of plasmids for secretory expression of proinsulin fused with 1, 2, 3, 4, 5, 6, 7, 8, 9, 10, 11, 12, 13, 14, 15, 17, 20, 50, 100, 150, 200, 250, 300, 350, 400, or 440 amino acid residues of N-terminus of mature cell surface layer protein CspB of *Corynebacterium glutamicum* ATCC 13869

As described above, the nucleotide sequence of the gene coding for CspB, which is a cell surface layer protein of *C. glutamicum*, has already been determined (Mol. Microbiol., 9, 97-109 (1993)). In *C. glutamicum*, CspB localizes in the cell surface layer and forms a layer called S-layer, and it is known that a region of highly hydrophobic amino acid residues locating on the C-terminal side participates in the localization (Mol. Microbiol., 9, 97-109 (1993)). By referring to this sequence, the primers shown in SEQ ID NO: 12 and 14 were synthesized, and by PCR using the chromosomal DNA of *C. glutamicum* ATCC 13869 prepared in a conventional manner (method of Saito and Miura [Biochem. Biophys. Act., 72, 619 (1963)]) as the template, a 5'-upstream region including the promoter of the gene coding for CspB (henceforth also referred to as CspB promoter region), and a region coding for the signal peptide 30 amino acid residues of the N-terminus of CspB and the N-terminal 440 amino acid residues of the CspB mature protein were amplified. The N-terminal 440 amino acid residues of the CspB mature protein refer to the part of the 469 amino acid residues of the full length CspB mature protein of *C. glutamicum* ATCC 13869 (SEQ ID NO: 96) other than the C-terminal 29 amino acid residues constituting the hydrophobic region. For PCR, Pyrobest DNA Polymerase (Takara Bio) was used, and the reaction conditions were according to the protocol recommended by the manufacturer.

Then, in order to construct plasmids for secretory expression of proinsulin fused with 1, 2, 3, 4, 5, 6, 7, 8, 9, 10, 11, 12, 13, 14, 15, 17, 20, 50, 100, 150, 200, 250, 300, 350, 400, or 440 amino acid residues of the N-terminus of the mature cell surface layer protein CspB of *C. glutamicum*, PCR was performed by using the PCR product amplified above as the template, and synthetic DNA pairs of SEQ ID NOS: 12 and 15, SEQ ID NOS: 12 and 16, SEQ ID NOS: 12 and 17, SEQ ID NOS: 12 and 18, SEQ ID NOS: 12 and 19, SEQ ID NOS: 12 and 20, SEQ ID NOS: 12 and 21, SEQ ID NOS: 12 and 22, SEQ ID NOS: 12 and 23, SEQ ID NOS: 12 and 24, SEQ ID NOS: 12 and 25, SEQ ID NOS: 12 and 26, SEQ ID NOS: 12 and 27, SEQ ID NOS: 12 and 28, SEQ ID NOS: 12 and 29, SEQ ID NOS: 12 and 20, SEQ ID NOS: 12 and 31, SEQ ID NOS: 12 and 32, SEQ ID NOS: 12 and 33, SEQ ID NOS: 12 and 34, SEQ ID NOS: 12 and 35, SEQ ID NOS: 12 and 36, SEQ ID NOS: 12 and 37, SEQ ID NOS: 12 and 38, SEQ ID NOS: 12 and 39, or SEQ ID NOS: 12 and 40 as the primers to amplify the CspB promoter region, and the region coding for the signal peptide 30 amino acid residues of the N-terminus of CspB, and 1, 2, 3, 4, 5, 6, 7, 8, 9, 10, 11, 12, 13, 14, 15, 17, 20, 50, 100, 150, 200, 250, 300, 350, 400, or 440 amino acid residues of the N-terminus of the CspB mature protein, respectively. Further, by PCR using the plasmid pPKPIns constructed in Example 1(1) as the template and the synthetic DNA shown in SEQ ID NOS: 9 and 41 as the primers, the PIns gene region was amplified to obtain a Pins gene fragment.

Further, by PCR using both the amplified DNA fragments (i.e. the fragment of the CspB promoter region and the region coding for the CspB signal peptide and 1, 2, 3, 4, 5, 6, 7, 8, 9, 10, 11, 12, 13, 14, 15, 17, 20, 50, 100, 150, 200, 250, 300, 350, 400, or 440 amino acid residues of the N-terminus of the mature CspB, and the PIns gene fragment) as the template and the DNAs shown in SEQ ID NOS: 12 and 41 as the primers, DNA fragments each consisting of both the DNA fragments fused together were obtained. In the primers of SEQ ID NOS: 12 and 41, the recognition sequence for the restriction enzyme KpnI was designed. The primers of SEQ ID NOS: 15 to 40 comprise a sequence coding for an amino acid sequence on the N-terminal side of PIns for constructing a fusion gene of a region coding for the N-terminus of the CspB mature protein and the Pins gene. For PCR, Pyrobest DNA Polymerase (Takara Bio) was used, and the reaction conditions were according to the protocol recommended by the manufacturer. These DNA fragments were treated with the restriction enzyme KpnI, and then inserted into pPK4 described in Japanese Patent Laid-open (Kokai) No. 9-322774 at the KpnI site to obtain pPKK1PIns, pPKK2PIns, pPKK3 Pins, pPKK4PIns, pPKK5PIns, pPKK6PIns, pPKK7PIns, pPKK8PIns, pPKK9PIns, pPKK10PIns, pPKK11PIns, pPKK12PIns, pPKK13PIns, pPKK14PIns, pPKK15PIns, pPKK17PIns, pPKK20PIns, pPKK50PIns, pPKK100PIns, pPKK150PIns, pPKK200PIns, pPKK250PIns, pPKK300PIns, pPKK350PIns, pPKK400PIns, and pPKK440PIns, respectively. By nucleotide sequencing of the insertion fragments, constructions of the expected fusion genes were confirmed. The nucleotide sequencing was performed by using BigDye (registered trademark) Terminator v3.1 Cycle Sequencing Kit (Applied Biosystems) and 3130 Genetic Analyzer (Applied Biosystems).

(3) Secretory expression of proinsulin fused with 1, 2, 3, 4, 5, 6, 7, 8, 9, 10, 11, 12, 13, 14, 15, 17, 20, 50, 100, 150, 200, 250, 300, 350, 400, or 440 amino acid residues of N-terminus of mature cell surface layer protein CspB of *Corynebacterium glutamicum* ATCC 13869 in *Corynebacterium glutamicum* YDK010 strain The *C. glutamicum* YDK010 strain described in WO2004/029254 was transformed with pPKPIns constructed in Example 1(1), which is a plasmid for secretory expression of proinsulin not fused with the N-terminal amino acid residue of the mature CspB, as well as pPKK1Pins, pPKK2Pins, pPKK3PIns, pPKK4PIns, pPKK5PIns, pPKK6PIns, pPKK7PIns, pPKK8PIns, pPKK9PIns, pPKK10PIns, pPKK11PIns, pPKK12PIns, pPKK13PIns, pPKK14PIns, pPKK15PIns, pPKK17PIns, pPKK20PIns, pPKK50PIns, pPKK100PIns, pPKK150PIns, pPKK200PIns, pPKK250PIns, pPKK300PIns, pPKK350PIns, pPKK400PIns, and pPKK440PIns constructed in Example 1(2), which are plasmids for secretory expression of proinsulin fused with 1, 2, 3, 4, 5, 6, 7, 8, 9, 10, 11, 12, 13, 14, 15, 17, 20, 50, 100, 150, 200, 250, 300, 350, 400, or 440 amino acid residues of the N-terminus of the mature protein cell surface layer protein CspB of *C. glutamicum* ATCC 13869. The *C. glutamicum* YDK010 strain is a cell surface layer protein PS2 (CspB) deficient strain of *C. glutamicum* AJ12036 (FERM BP-734) (WO2004/029254). Each of the obtained transformants was cultured in the MM liquid medium (120 g of glucose, 3 g of magnesium sulfate heptahydrate, 30 g of ammonium sulfate, 1.5 g of potassium dihydrogenphosphate, 0.03 g of iron sulfate heptahydrate, 0.03 g of manganese sulfate tetrahydrate, 0.45 mg of thiamine hydrochloride, 0.45 mg of biotin, 0.15 g of DL-methionine, and 50 g of calcium carbonate made into a volume of 1 L with water, and adjusted to pH 7.0) containing 25 mg/l of kanamycin at 30° C. for 72 hours. After completion of the culture, 10 μL of the culture supernatant obtained by centrifuging each culture broth was subjected to reduced SDS-PAGE, and then staining was performed with CBB R-250 (Bio-Rad). As a result, a band indicating a protein having the intended molecular weight was only very weakly confirmed with the naked eye for the strain introduced with the plasmid pPKPIns that expresses PIns not fused with the N-terminal amino acids of the mature protein of CspB. In contrast, for the strain introduced with each of the plasmids that express Pins fused with the N-terminal amino acids of the mature protein of CspB, a band indicating a protein having the intended molecular weight was intensely detected, and thus it was confirmed that the secretion amount was significantly increased by the fusion with the N-terminal amino acids of the mature protein of CspB. This secretion amount-improving effect was especially remarkable with fusion of 3 to 8, 17, and 50 amino acid residues of the N-terminus of CspB (FIG. 1). Furthermore, the secretion amounts were quantified by using a densitometer for the objective protein bands detected in SDS-PAGE. As a result, the secretion amount increased 1.5 times or more for almost all the strains introduced with the plasmids that express PIns fused with the N-terminal amino acids of the mature protein of CspB, compared with the strain introduced with the plasmid pPKPIns that expresses PIns not fused with the N-terminal amino acids of the mature protein of CspB. In particular, for the strains introduced with pPKK4 Pins, pPKK6PIns, pPKK17PIns, and pPKK50 Pins for fusion of 4, 6, 17, and 50 amino acid residues of the N-terminus of the mature CspB, the secretion amount increased 10 times or more ("Secretion amount (%)" in Table 1). Further, with the fusion of 3 to 8 amino acid residues of the N-terminus of the mature CspB, the secretion amount of PIns increased 5 times or more ("Secretion amount (%)" in Table 1. Furthermore, relative values of the numbers of secreted molecules were calculated on the basis of the molecular weights of the objective fusion proteins. As a result, it was reconfirmed that the secretion amount of PIns remarkably increased especially with fusion of 3 to 8, 17 or 50 amino acid residues of the N-terminus of the mature CspB ("Relative amount (%)" in Table 1). Meanwhile, when it was attempted to determine the N-terminal amino acid sequences of the fusion proteins for which improvement of the secretion amount was confirmed by using a protein sequencer PPSQ-21A (Shimadzu), the N-terminal amino acid residues of these fusion proteins could not be determined, and therefore it was confirmed that the N-terminal amino acid residues of these fusion proteins were converted into pyroglutamic acid residues in consideration of the results described later.

TABLE 1

| Strains | Secretion amount (%) | Molecular weight | Relative amount (%)* |
|---|---|---|---|
| YDK010/pPKPIns | 100.0 | 9394.5 | 100.0 |
| YDK010/pPKK1PIns | 0.0 | 9522.7 | 0.0 |
| YDK010/pPKK2PIns | 134.2 | 9651.8 | 130.6 |
| YDK010/pPKK3PIns | 585.6 | 9752.9 | 564.1 |
| YDK010/pPKK4PIns | 1459.3 | 9867.0 | 1389.5 |
| YDK010/pPKK5PIns | 767.9 | 9964.1 | 724.0 |
| YDK010/pPKK6PIns | 1188.3 | 10065.2 | 1109.1 |
| YDK010/pPKK7PIns | 576.6 | 10212.4 | 530.4 |
| YDK010/pPKK8PIns | 568.7 | 10326.5 | 517.3 |
| YDK010/pPKK9PIns | 288.2 | 10439.6 | 259.3 |
| YDK010/pPKK10PIns | 213.6 | 10553.7 | 190.2 |
| YDK010/pPKK11PIns | 186.6 | 10667.8 | 164.4 |
| YDK010/pPKK12PIns | 424.4 | 10724.9 | 371.6 |
| YDK010/pPKK13PIns | 109.1 | 10872.0 | 94.2 |
| YDK010/pPKK14PIns | 81.9 | 10986.1 | 70.0 |
| YDK010/pPKK15PIns | 316.3 | 11101.2 | 267.7 |
| YDK010/pPKK17PIns | 1456.5 | 11287.4 | 1212.2 |
| YDK010/pPKK20PIns | 316.4 | 11532.6 | 257.7 |
| YDK010/pPKK50PIns | 1705.1 | 15010.3 | 1067.2 |
| YDK010/pPKK100PIns | 228.9 | 20296.9 | 106.0 |
| YDK010/pPKK150PIns | 101.9 | 25739.9 | 37.2 |
| YDK010/pPKK250PIns | 626.6 | 36749.1 | 160.2 |

*Relative amount (%) = Secretion amount (%) × 9394.5/Molecular weight

Example 2

Secretory Expression of Proinsulin Fused with N-Terminal 6 Amino Acid Residues of Each CspB Mature Proteins Derived from *Corynebacterium* Bacteria Having Cell Surface Layer Protein CspB Homologue (1) Construction of Plasmids for Secretory Expression of Proinsulin Fused with N-Terminal 6 Amino Acid Residues of Each CspB Mature Proteins Derived from *Corynebacterium* Bacteria Having Cell Surface Layer Protein CspB Homologue There are *Corynebacterium* bacterium strains having a homologue of the cell surface layer protein CspB, and those not having such a homologue, and amino acid sequences of CspB homologues have been already reported for 28 strains of *C. glutamicum* (J. Biotechnol., 112, 177-193 (2004)). In comparison of the N-terminal amino acid sequences of the CspB homologues derived from these 28 strains, it was found that the signal sequence 30 amino acid residues and the N-terminal 3 amino acid residues (Gln-Glu-Thr) of the mature protein were completely conserved. Further, in comparison of the N-termini of the mature proteins of the CspB homologues up to 6 amino acid residues, it was found that the amino acid sequences were classified into 5 patterns, i.e., Gln-Glu-Thr-Asn-Pro-Thr (henceforth also represented as QETNPT (SEQ ID NO: 97)), Gln-Glu-Thr-Gly-Thr-Tyr (henceforth also represented as QETGTY (SEQ ID NO: 98)), Gln-Glu-Thr-Thr-Val-Thr (henceforth also represented as QETTVT (SEQ ID NO: 99)), Gln-Glu-Thr-Pro-Val-Thr (henceforth also represented as QETPVT (SEQ ID NO: 100)), and Gln-Glu-Thr-Ala-Val-Thr (henceforth also represented as QETAVT (SEQ ID NO: 101)). The N-terminal sequence of the mature CspB of *C. glutamicum* ATCC 13869 used in Example 1 is the QETNPT type. Therefore, in order to construct expression plasmids for proinsulin fused with amino acids of the other four patterns (QETGTY type, QETTVT type, QETPVT type, QETAVT type), PCR was performed by using pPKK6PIns constructed in Example 1(2) as the template, and synthetic DNAs shown in SEQ ID NOS: 12 and 42, SEQ ID NOS: 12 and 43, SEQ ID NOS: 12 and 44, or SEQ ID NOS: 12 and 45 as the primers to amplify fragments each consisting of the CspB promoter region and the region coding for the CspB signal peptide 30 amino acid residues further fused with the region coding for the N-terminal 6 amino acid residues of the mature CspB (QETGTY, QETTVT, QETPVT, or QETAVT), respectively. Further, the PIns gene region was amplified by PCR using the plasmid pPKPIns constructed in Example 1(1) as the template and the synthetic DNAs shown in SEQ ID NOS: 9 and 41 as the primers to obtain a Pins gene fragment.

Furthermore, by PCR using both the amplified DNA fragments (i.e. the fragment of the CspB promoter region and the region coding for the CspB signal peptide and the N-terminal 6 amino acid residues of the mature CspB (QETGTY, QETTVT, QETPVT, or QETAVT), and the PIns gene fragment) as the template and DNAs shown in SEQ ID NOS: 12 and 41 as the primers, DNA fragments each consisting of both the DNA fragments fused together was obtained. In the primers of SEQ ID NOS: 12 and 41, the recognition sequence for the restriction enzyme KpnI was designed. The primers of SEQ ID NOS: 42 to 45 include a sequence coding for an amino acid sequence on the N-terminal side of Pins for constructing a fusion gene of a region coding for the N-terminus of the CspB mature protein and the Pins gene. For PCR, Pyrobest DNA Polymerase (Takara Bio) was used, and the reaction conditions were according to the protocol recommended by the manufacturer. These DNA fragments were treated with the restriction enzyme KpnI, and then inserted into pPK4 described in Japanese Patent Laid-open (Kokai) No. 9-322774 at the KpnI site to obtain pPK-QETGTY-PIn, pPK-QETTVT-PIns, pPK-QETPVT-PIns, and pPK-QETAVT-PIns, respectively. By nucleotide sequencing of the insertion fragments, constructions of the expected fusion genes were confirmed. The nucleotide sequencing was performed by using BigDye (registered trademark) Terminator v3.1 Cycle Sequencing Kit (Applied Biosystems) and 3130 Genetic Analyzer (Applied Biosystems).

(2) Secretory Expression of Proinsulin Fused with N-Terminal 6 Amino Acid Residues of Each CspB Mature Protein Derived from *Corynebacterium* Bacteria Having Cell Surface Layer Protein CspB Homologue in *Corynebacterium glutamicum* YDK010 Strain The *C. glutamicum* YDK010 strain described in WO2004/029254 was transformed with pPKPIns constructed in Example 1(1), which is a plasmid for secretory expression of proinsulin not fused with the N-terminal amino acid residues of the mature CspB, and pPKK6PIns constructed in Example 1(2), which is a plasmid for secretory expression of proinsulin fused with the N-terminal 6 amino acid residues (QETNPT) of the mature cell surface layer protein CspB of *C. glutamicum* ATCC 13869, as well as pPK-QETGTY-PIns, pPK-QETTVT-PIns, pPK-QETPVT-PIns, and pPK-QETAVT-PIns constructed in Example 2(1), which are plasmids for secretory expression of proinsulin fused with the N-terminal 6 amino acid residues (QETGTY, QETTVT, QETPVT, or QETAVT) of the mature protein of each of cell surface layer protein CspB homologues derived from *Corynebacterium* bacteria. Each of the obtained transformants was cultured in the MM liquid medium (120 g of glucose, 3 g of magnesium sulfate heptahydrate, 30 g of ammonium sulfate, 1.5 g of potassium dihydrogenphosphate, 0.03 g of iron sulfate heptahydrate, 0.03 g of manganese sulfate tetrahydrate, 0.45 mg of thiamine hydrochloride, 0.45 mg of biotin, 0.15 g of DL-methionine, and 50 g of calcium carbonate made into a volume of 1 L with water, and adjusted to pH 7.0) containing 25 mg/l of kanamycin at 30° C. for 72 hours. After completion of the culture, the culture supernatant obtained by centrifuging each culture broth was subjected to reduced SDS-PAGE, and then staining was performed with CBB R-250 (Bio-Rad). As a result, like the strain introduced with pPKK6PIns, a band of a fusion protein having the intended molecular weight was definitely detected for all the strains introduced with the plasmids pPK-QETGTY-PIns, pPK-QETTVT-PIns, pPK-QETPVT-PIns, and pPK-QETAVT-Pins, and thus it was confirmed that the secretion amount significantly increased in these strains compared with the pPKPIns-introduced strain that expresses PIns not fused with the N-terminal amino acids of the mature CspB. Furthermore, the secretion amounts were quantified by using a densitometer for the objective protein bands detected in SDS-PAGE. As a result, the secretion amount of PIns increased 5 times for all the strains introduced with the plasmids that express Pins fused with the N-terminal amino acids of the mature protein of CspB compared with the strain introduced with the plasmid pPKPIns that expresses Pins not fused with the N-terminal amino acids of the mature protein of CspB (Table 2). Meanwhile, when it was attempted to determine the N-terminal amino acid sequences of the fusion proteins for which improvement of the secretion amount was confirmed by using the protein sequencer PPSQ-21A (Shimadzu), the N-terminal amino acid residues of these fusion proteins could not be determined, and therefore it was confirmed that the N-terminal amino acid residues of these fusion proteins were converted into pyroglutamic acid residues in consideration of the results described later.

TABLE 2

| Strains | Secretion amount (%) |
|---|---|
| YDK010/pPKPIns | 100.0 |
| YDK010/pPKK6PIns | 811.0 |
| YDK010/pPK-QETGTY-PIns | 548.0 |
| YDK010/pPK-QETTVT-PIns | 809.6 |
| YDK010/pPK-QETPVT-PIns | 904.4 |
| YDK010/pPK-QETAVT-PIns | 586.4 |

Example 3

Secretory Expression of Fusion Proinsulin Having Protease Recognition Sequence Inserted Between N-Terminal Amino Acid Sequence of CspB Mature Protein and Proinsulin Sequence (1) Construction of Plasmids for Secretory Expression of Fusion Proinsulin Having Recognition Sequence of Factor Xa Protease or ProTEV Protease Inserted Between N-Terminal Amino Acid Sequence of CspB Mature Protein and Proinsulin Sequence For expression of a certain objective protein as a fusion protein with an amino acid sequence other than the objective protein, there is widely known a convenient method for obtaining the objective protein by providing a recognition sequence of a specific protease showing high substrate specificity between the amino acid sequence of the objective protein and the fused amino acid sequence, and cleaving the expressed fusion protein with the specific protease. As a protease showing high substrate specificity, there are known, for example, factor Xa protease and ProTEV protease, and they recognize the sequences of Ile-Glu-Gly-Arg (=IEGR, SEQ ID NO: 105) and Glu-Asn-Leu-Tyr-Phe-Gln (=ENLYFQ, SEQ ID NO: 106) in proteins, respectively, and specifically digest the protein at the C-terminal side of each recognition sequence. Therefore, for example, in the case of CspB-fused Pins, by constructing a fusion PIns gene including a nucleotide sequence coding for the recognition sequence (IEGR) for the factor Xa protease or the recognition sequence (ENLYFQ) for the ProTEV protease inserted between the nucleotide sequence coding for the N-terminal amino acid residues of the CspB mature protein and the nucleotide sequence coding for proinsulin, and allowing secretory expression of the fusion Pins, PIns can be easily obtained from the fusion PIns by using either one of the proteases.

By PCR using pPKK6PIns constructed in Example 1(2) as the template, and the synthetic DNAs shown in SEQ ID NOS: 12 and 46 or SEQ ID NOS: 12 and 47 as the primers, fragments each consisting of the CspB promoter region and the region coding for the signal peptide 30 amino acid residues of the N-terminus of CspB and the N-terminal 6 amino acid residues (QETNPT) of the CspB mature protein further fused with a region coding for IEGR, which is recognized by the factor Xa protease, or ENLYFQ, which is recognized by the ProTEV protease, were amplified, respectively. Further, the PIns gene region was amplified by PCR using the plasmid pPKPIns constructed in Example 1(1) as the template, and the synthetic DNAs shown in SEQ ID NOS: 48 and 41 or SEQ ID NOS: 49 and 41 to obtain a PIns gene fragment. Furthermore, by PCR using both the amplified DNA fragments (i.e. the fragment of the CspB promoter region, and the region coding for the signal peptide of CspB, the N-terminal 6 amino acid residues (QETNPT) of the CspB mature protein, and IEGR or ENLYFQ, and the PIns gene fragment) as the template and DNAs shown in SEQ ID NOS: 12 and 41 as the primers, DNA fragments each consisting of both the DNA fragments fused together were obtained. In the primers of SEQ ID NOS: 12 and 41, the recognition sequence for the restriction enzyme KpnI was designed. In the primer of SEQ ID NO: 46, a sequence coding for the amino acid sequence of the N-terminal side of PIns for constructing a fusion gene of the nucleotide sequence coding for IEGR and the PIns gene was designed. In the primer of SEQ ID NO: 47, a sequence coding for the amino acid sequence of the N-terminal side of PIns for constructing a fusion gene of the nucleotide sequence coding for ENLYFQ and the PIns gene was designed. For PCR, Pyrobest DNA Polymerase (Takara Bio) was used, and the reaction conditions were according to the protocol recommended by the manufacturer. These DNA fragments were treated with the restriction enzyme KpnI, and then inserted into pPK4 described in Japanese Patent Laid-open (Kokai) No. 9-322774 at the KpnI site to obtain pPKK6Xa-PIns and pPKK6TEV-PIns, respectively.

Similarly, by PCR using pPKK17PIns or pPKK50PIns constructed in Example 1(2) as the template, and the synthetic DNAs shown in SEQ ID NOS: 12 and 50 or SEQ ID NOS: 12 and 51 as the primers, fragments each consisting of the CspB promoter region and the region coding for the signal peptide 30 amino acid residues of the N-terminus of CspB and the N-terminal 17 or 50 amino acid residues of the CspB mature protein further fused with the region coding for IEGR, which is recognized by the factor Xa protease, were amplified, respectively. Further, the PIns gene region was amplified by PCR using the plasmid pPKPIns constructed in Example 1(1) as the template, and the synthetic DNAs shown in SEQ ID NOS: 48 and 41 or SEQ ID NOS: 49 and 41 as the primers to obtain a PIns gene fragment. Furthermore, by PCR using both the amplified DNA fragments (i.e. the fragment of the CspB promoter region, and the region coding for the signal peptide of CspB, the N-terminal 17 or 50 amino acid residues of the CspB mature protein, and IEGR, and the PIns gene fragment) as the template and DNAs shown in SEQ ID NOS: 12 and 41 as the primers, DNA fragments each consisting of both the DNA fragments fused together were obtained. In the primers of SEQ ID NOS: 12 and 41, the recognition sequence for the restriction enzyme KpnI was designed. In the primers of SEQ ID NOS: 50 and 51, a sequence coding for the amino acid sequence of the N-terminal side of PIns for constructing a fusion gene of the nucleotide sequence coding for IEGR and the PIns gene was designed. For PCR, Pyrobest DNA Polymerase (Takara Bio) was used, and the reaction conditions were according to the protocol recommended by the manufacturer. These DNA fragments were treated with the restriction enzyme KpnI, and then inserted into pPK4 described in Japanese Patent Laid-open (Kokai) No. 9-322774 at the KpnI site to obtain pPKK17Xa-PIns and pPKK50Xa-PIns, respectively. By nucleotide sequencing of the insertion fragments, constructions of the expected fusion genes were confirmed. The nucleotide sequencing was performed by using BigDye (registered trademark) Terminator v3.1 Cycle Sequencing Kit (Applied Biosystems) and 3130 Genetic Analyzer (Applied Biosystems).

(2) Secretory Expression of Fusion Proinsulin Having Recognition Sequence of Factor Xa Protease or proTEV Protease Inserted Between N-Terminal Amino Acid Residues of CspB Mature Protein and Proinsulin Sequence in *Corynebacterium glutamicum* YDK010 Strain The *C. glutamicum* YDK010 strain described in WO2004/029254 was transformed with pPKPIns constructed in Example 1(1), which is a plasmid for secretory expression of proinsulin not fused with the N-terminal amino acid residues of the mature CspB, as well as pPKK6Xa-PIns, pPKK17Xa-PIns, and pPKK50Xa-PIns constructed in Example 3(1), which are plasmids for secretory expression of fusion proinsulin having the recognition sequence of the factor Xa protease inserted between the N-terminal amino acid residues (6, 17 or 50 residues) of the CspB mature protein and the proinsulin sequence, and pPKK6TEV-PIns also constructed in Example 3(1), which is a plasmid for secretory expression of fusion proinsulin having the recognition sequence of the proTEV protease inserted between the N-terminal amino acid residues (6 residues) of the CspB mature protein and the proinsulin sequence. Each of the obtained transformants was cultured in the MM liquid medium (120 g of glucose, 3 g of magnesium sulfate heptahydrate, 30 g of ammonium sulfate, 1.5 g of potassium dihydrogenphosphate, 0.03 g of iron sulfate heptahydrate, 0.03 g of manganese sulfate tetrahydrate, 0.45 mg of thiamine hydrochloride, 0.45 mg of biotin, 0.15 g of DL-methionine, and 50 g of calcium carbonate made into a volume of 1 L with water, and adjusted to pH 7.0) containing 25 mg/l of kanamycin at 30° C. for 72 hours. After completion of the culture, the culture supernatant obtained by centrifuging each culture broth was subjected to reduced SDS-PAGE, and then staining was performed with CBB R-250 (Bio-Rad). As a result, for all the strains introduced with the plasmids pPKK6Xa-PIns, pPKK17Xa-PIns, pPKK50Xa-PIns, and pPKK6TEV-PIns, a band of a fusion protein having the intended molecular weight was detected, and thus it was confirmed that the secretion amount significantly increased in these strains compared with the pPKPIns-introduced strain that expresses PIns not fused with the N-terminal amino acids of the mature CspB. Furthermore, the secretion amounts were quantified by using a densitometer. As a result, it was confirmed that the secretion amount of PIns increased with all the strains introduced with the plasmids that expresses PIns fused with the N-terminal amino acids of the mature protein of CspB and the protease recognition sequence, compared with the strain introduced with the pPKPIns that expresses PIns not fused with the N-terminal amino acids of the mature protein of CspB, and thus it was revealed that the secretion amount of the objective protein is improved, even if the protease recognition sequence is fused immediately after the N-terminal amino acid residues of the CspB mature protein (Table 3). Meanwhile, when it was attempted to determine the N-terminal amino acid sequences of the fusion proteins for which improvement of the secretion amount was confirmed by using the protein sequencer PPSQ-21A (Shimadzu), the N-terminal amino acid residues of these fusion proteins could not be determined. Furthermore, among these fusion proteins, the fusion protein produced through secretory production by the YDK010/pPKK6Xa-PIns strain was separated and purified by reverse phase HPLC, and then the molecular weight thereof was determined by using a mass spectrometer micrOTOF (Bruker Daltonics). As a result, the measured value was 10497 against the theoretical molecular weight of 10514.69, and thus it was revealed that the molecular weight decreased by the mass corresponding to a water molecule (about 18). Further, the molecular weight of the fusion protein produced through secretory production by the YDK010/pPKK6TEV-PIns strain was similarly determined by using the mass spectrometer AXIMA-TOF2 (Shimadzu). As a result, the measured value was 10836.89 against the theoretical molecular weight of 10854.02, and thus the molecular weight decreased by the mass corresponding to a water molecule (about 18) again. On the basis of these results and the results mentioned later, it was confirmed that the N-terminal amino acid residues of these fusion proteins were converted into pyroglutamic acid residues.

TABLE 3

| Strains | Secretion amount (%) | Molecular weight | Relative amount (%)* |
|---|---|---|---|
| YDK010/pPKPIns | 100.0 | 9394.5 | 100.0 |
| YDK010/pPKK6Xa-PIns | 2271.5 | 10538.7 | 2024.8 |
| YDK010/pPKK17Xa-PIns | 782.4 | 11760.9 | 625.0 |
| YDK010/pPKK50Xa-PIns | 545.5 | 15483.8 | 330.9 |
| YDK010/pPKK6TEV-PIns | 335.3 | 10878.0 | 289.5 |

*Relative amount (%) = Secretion amount (%) × 9394.5/Molecular weight (3) Digestion of CspB-Fused Proinsulin Having Recognition Sequence of Factor Xa Protease or proTEV Protease Inserted Between N-Terminal Amino Acid Sequence of CspB Mature Protein and Proinsulin Sequence with Each Protease By using the culture supernatants obtained by centrifuging the culture broths of YDK010/pPKK6Xa-PIns, YDK010/pPKK17Xa-PIns, and YDK010/pPKK50Xa-PIns obtained in Example 3(2) as the substrate, and the factor Xa protease (Novagen), the digestion reaction of the proteins was performed according to the protocol recommended by the manufacturer. The solutions after the reaction were subjected to reduced SDS-PAGE, and then staining was performed with CBB R-250 (Bio-Rad). As a result, for all the strains, a band of a protein having the same molecular weight as that of the objective PIns was detected. When the N-terminal amino acid sequences of these protein bands were determined by using the protein sequencer PPSQ-21A (Shimadzu), the N-terminal sequence of PIns could be confirmed for all the proteins. Therefore, it was confirmed that the fused peptides were digested by the factor Xa protease to generate the objective PIns.

Further, by using the culture supernatant obtained by centrifuging the culture broth of YDK010/pPKK6TEV-PIns also obtained in Example 3(2) as the substrate, and the ProTEV protease (Promega), the digestion reaction of the protein was performed according to the protocol recommended by the manufacturer. The solution after the reaction was subjected to reduced SDS-PAGE, and then staining was performed with CBB R-250 (Bio-Rad). As a result, a band of a protein having the same molecular weight as that of the objective PIns was detected. When the N-terminal amino acid sequence of this protein band was determined by using the protein sequencer PPSQ-21A (Shimadzu), the N-terminal sequence of PIns could be confirmed. Therefore, it was confirmed that the fused peptide was digested by the ProTEV protease to generate the objective PIns.

Example 4

Secretory Expression of Human Growth Hormone (hGH) Fused with N-Terminal Amino Acid Residues of Mature Cell Surface Layer Protein CspB of *Corynebacterium glutamicum* ATCC 13869

(1) Total Synthesis of Human Growth Hormone (hGH) Gene and Construction of Plasmids for Secretory Expression of Human Growth Hormone (hGH) in *Corynebacterium glutamicum*

The amino acid sequence of the human growth hormone (hGH) has already been determined (Genbank Accession No. CAA23779.1). In consideration of the amino acid sequence of the mature human growth hormone corresponding to the part of the aforementioned sequence other than the N-terminal signal sequence 26 amino acid residues and the codon frequencies in *C. glutamicum*, DNAs shown in SEQ ID NOS: 52 to 65 were synthesized. The hGH gene was amplified by PCR using these DNAs as the template and separately synthesized DNAs shown in SEQ ID NOS: 66 and 67 as the primers to obtain a DNA fragment of about 0.6 kbp shown in SEQ ID NO: 68. This DNA fragment was inserted into a cloning vector pHSG398 (Takara Bio) at the SmaI site to obtain pHSG-hGH. The hGH gene region was amplified by PCR using the above pHSG-hGH as the template and DNAs shown in SEQ ID NOS: 66 and 67 as the primer to obtain a hGH gene fragment of about 0.6 kbp. Then, the promoter region for CspB derived from *C. glutamicum* ATCC 13869 and the region coding for the signal peptide of CspA derived from the *C. ammoniagenes* (*C. stationis*) ATCC 6872 strain or CspB derived from the *C. glutamicum* ATCC 13869 strain were amplified by PCR using pPKSPTG1 described in WO01/23591 or pPKPTG1 described in WO01/23591 as the template, and the primers shown in SEQ ID NOS: 12 and 69 or SEQ ID NOS: 12 and 70 to obtain DNA fragments of about 0.7 kbp each. The pPKSPTG1 is a vector for secretory expression of pro-transglutaminase (transglutaminase having a pro-structure moiety), and comprises the promoter of the cspB gene derived from the *C. glutamicum* ATCC 13869 strain, a DNA coding for the signal peptide 25 amino acid residues of CspA (SlpA) derived from the *C. ammoniagenes* (*C. stationis*) ATCC 6872 strain <Genbank Accession No. BAB62413.1> and expressibly ligated downstream from the promoter, and a protransglutaminase gene derived from *S. mobaraense*, ligated downstream from the DNA coding for the signal peptide so that the pro-transglutaminase is expressed as a fusion protein with the signal peptide. The pPKPTG1 contains the promoter region and a DNA coding for the signal peptide of CspB derived from the *C. glutamicum* ATCC 13869 strain. Furthermore, by PCR using both the amplified DNA fragments (i.e. the hHG gene fragment and the fragment of the CspB promoter region and the region coding for each signal peptide) as the template and the DNAs shown in SEQ ID NOS: 12 and 67 as the primers, DNA fragments of about 1.2 kbp each consisting of both the DNA fragments fused together were obtained. In the primers of SEQ ID NOS: 12 and 67, the recognition sequence for the restriction enzyme KpnI was designed. In the primers of SEQ ID NOS: 69 and 70, a sequence coding for the N-terminal amino acid residues of hGH for constructing a fusion gene of the region coding for each signal peptide and the hGH gene was designed. For PCR, Pyrobest DNA Polymerase (Takara Bio) was used, and the reaction conditions were according to the protocol recommended by the manufacturer. These DNA fragments were treated with the restriction enzyme KpnI, and then inserted into pPK4 described in Japanese Patent Laid-open (Kokai) No. 9-322774 at the KpnI site to obtain pPS-hGH and pPK-hGH, respectively. By nucleotide sequencing of the insertion fragments, constructions of the expected fusion genes were confirmed. The nucleotide sequencing was always performed by using BigDye (registered trademark) Terminator v3.1 Cycle Sequencing Kit (Applied Biosystems) and 3130 Genetic Analyzer (Applied Biosystems).

(2) Construction of Plasmids for Secretory Expression of Human Growth Hormone (hGH) Fused with Signal Peptide and Mature Protein N-Terminal Amino Acid Residues of Cell Surface Layer Protein CspB of *Corynebacterium glutamicum* ATCC 13869 and Factor Xa Protease Recognition Sequence By PCR using pPKK6Xa-PIns, pPKK17Xa-PIns, or pPKK50Xa-PIns constructed in Example 3(1) as the template and the synthetic DNAs shown in SEQ ID NOS: 12 and 71, SEQ ID NOS: 12 and 72, or SEQ ID NOS: 12 and 73 as the primers, the CspB promoter region, and a region coding for the signal peptide 30 amino acid residues of the N-terminus of CspB, the N-terminal amino acid residues (6, 17, or 50 residues) of the CspB mature protein, and the factor Xa protease recognition sequence (IEGR) were amplified. Further, the hGH gene region was amplified by PCR using the plasmid pPS-hGH constructed in Example 4(1) as the template and the synthetic DNAs shown in SEQ ID NOS: 66 and 67 as the primers. Further, by PCR using both the amplified DNA fragments (i.e. the fragment of the CspB promoter region, and the region coding for the signal peptide of CspB, the N-terminal amino acid residues of the CspB mature protein, and IEGR, and the hGH gene fragment) as the template and DNAs shown in SEQ ID NOS: 12 and 67 as the primers, DNA fragments each consisting of both the DNA fragments fused together were obtained. In the primers of SEQ ID NOS: 12 and 67, the recognition sequence for the restriction enzyme KpnI was designed. In the primers of SEQ ID NOS: 71, 72, and 73, a sequence coding for the N-terminal amino acid residues of hGH for constructing a fusion gene of the region coding for the factor Xa protease recognition sequence (IEGR) and the hGH gene was designed. For PCR, Pyrobest DNA Polymerase (Takara Bio) was used, and the reaction conditions were according to the protocol recommended by the manufacturer. These DNA fragments were treated with the restriction enzyme KpnI, and then inserted into pPK4 described in Japanese Patent Laid-open (Kokai) No. 9-322774 at the KpnI site to obtain pPKK6Xa-hGH, pPKK17Xa-hGH, and pPKK50Xa-hGH, respectively.

(3) Construction of Plasmids for Secretory Expression of Human Growth Hormone (hGH) Fused with Signal Peptide of Cell Surface Layer Protein CspA of *Corynebacterium Ammoniagenes* (*C. Stationis*) ATCC 6872, N-Terminal Amino Acid Residues of Mature Cell Surface Layer Protein CspB of *Corynebacterium glutamicum* ATCC 13869, and Recognition Sequence of Factor Xa Protease By PCR using pPKSPTG1 described in WO01/23591 as the template and the synthetic DNAs shown in SEQ ID NO: 12 and 74 as the primers, the CspB promoter region and a region coding for the signal peptide 25 amino acid residues of the N-terminus of CspA derived from the *C. ammoniagenes* (*C. stationis*) ATCC 6872 were amplified. Further, by PCR using the plasmid pPKK6Xa-hGH constructed in Example 4(2) as the template and the synthetic DNAs shown in SEQ ID NO: 75 and 67 as the primers, a region coding for the N-terminal 6 amino acid residues (QETNPT) of the CspB mature protein and the recognition sequence (IEGR) for the factor Xa protease and the hGH gene region were amplified. Furthermore, by PCR using both the amplified DNA fragments (i.e. the fragment of the CspB promoter region and the region coding for the CspA signal peptide, and the fragment of the region coding for the N-terminal amino acid residues of CspB and IEGR and the hGH gene) as the template and the DNAs shown in SEQ ID NOS: 12 and 67 as the primers, a DNA fragment consisting of both the DNA fragments fused together was obtained. In the primers of SEQ ID NOS: 12 and 67, the recognition sequence for the restriction enzyme KpnI was designed. In the primer of SEQ ID NO: 74, a sequence coding for the N-terminal amino acid residues of the CspB mature protein for constructing a fusion gene of the region coding for the CspA signal peptide and the sequence coding for the N-terminal amino acid residues of the CspB protein was designed. For PCR, Pyrobest DNA Polymerase (Takara Bio) was used, and the reaction conditions were according to the protocol recommended by the manufacturer. This DNA fragment was treated with the restriction enzyme KpnI, and then inserted into pPK4 described in Japanese Patent Laid-open (Kokai) No. 9-322774 at the KpnI site to obtain pPSK6Xa-hGH.

Further, by PCR using pPKSPTG1 described in WO01/23591 as the template and the synthetic DNAs shown in SEQ ID NO: 12 and 76 as the primers, the CspB promoter region and the region coding for the signal peptide 25 amino acid residues of the N-terminus of CspA derived from *C. ammoniagenes* (*C. stationis*) ATCC 6872 were amplified. Further, by PCR using each of the plasmids pPKK17Xa-hGH and pPKK50Xa-hGH constructed in Example 4(2) as the template, and the synthetic DNAs shown in SEQ ID NO: 75 and 67 as the primers, a region coding for the N-terminal 17 or 50 amino acid residues of the CspB mature protein and the recognition sequence (IEGR) for the factor Xa protease and the hGH gene region were amplified. Furthermore, by PCR using both the amplified DNA fragments (i.e. the fragment of the CspB promoter region and the region coding for the CspA signal peptide, and the fragment of the region coding for the N-terminal amino acid residues of CspB and IEGR and the hGH gene) as the template and the DNAs shown in SEQ ID NOS: 12 and 67 as the primers, DNA fragments each consisting of both the DNA fragments fused together were obtained. In the primers of SEQ ID NOS: 12 and 67, the recognition sequence for the restriction enzyme KpnI was designed. In the primer of SEQ ID NO: 76, a sequence coding for the N-terminal amino acid residues of the CspB mature protein for constructing a fusion gene of the region coding for the CspA signal peptide and the sequence coding for the N-terminal amino acid residues of the CspB mature protein was designed. For PCR, Pyrobest DNA Polymerase (Takara Bio) was used, and the reaction conditions were according to the protocol recommended by the manufacturer. These DNA fragments were treated with the restriction enzyme KpnI, and then inserted into pPK4 described in Japanese Patent Laid-open (Kokai) No. 9-322774 at the KpnI site to obtain pPSK17Xa-hGH and pPSK50Xa-hGH, respectively.

Figure 2:
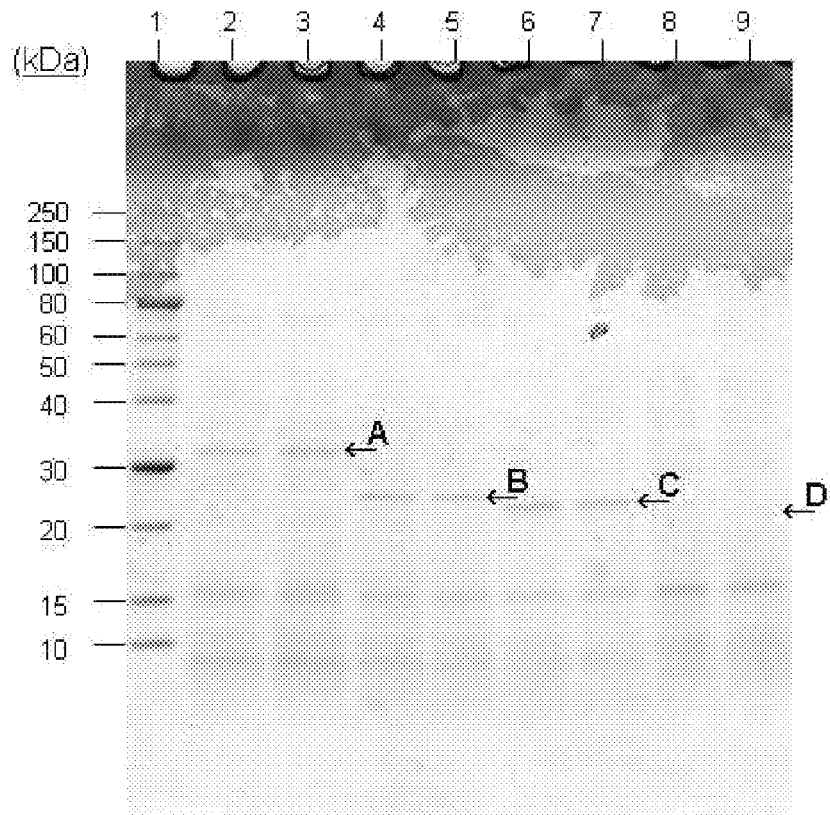
FIG. 2 is a photograph showing the results of SDS-PAGE of human growth hormone (hGH) fused with the signal sequence of CspB of *C. glutamicum* ATCC 13869, an N-terminal sequence of the mature CspB of *C. glutamicum* ATCC 13869, and a protease recognition sequence, which was expressed in the *C. glutamicum* YDK010 strain.
Figure 3:
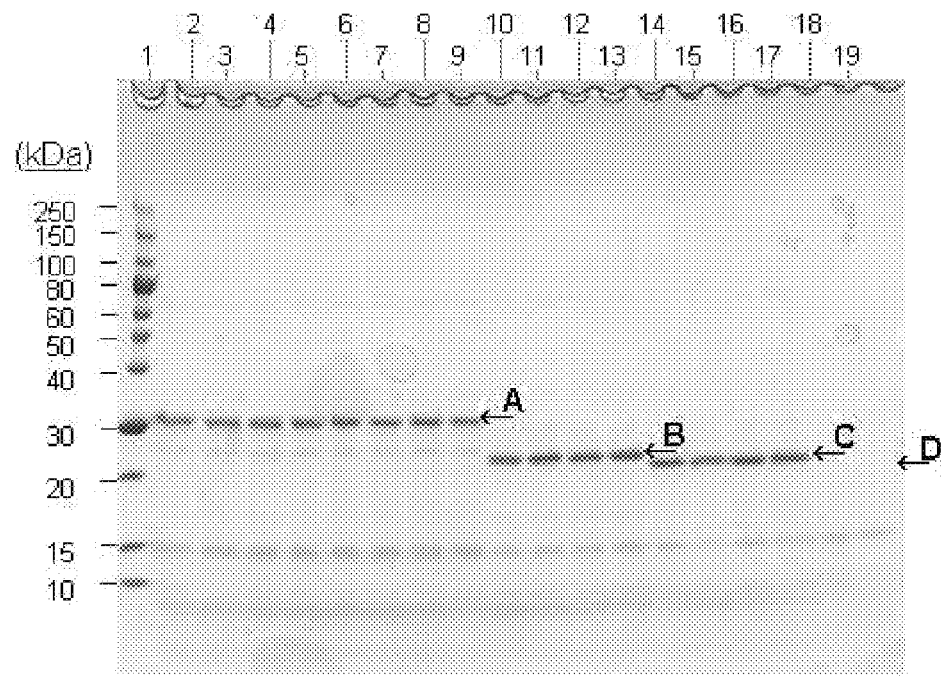
FIG. 3 is a photograph showing the results of SDS-PAGE of human growth hormone (hGH) fused with the signal sequence of CspA of *C. ammoniagenes* (*C. stationis*) ATCC 6872, an N-terminal sequence of the mature CspB of *C. glutamicum* ATCC 13869, and a protease recognition sequence, which was expressed in the *C. glutamicum* YDK010 strain.

(4) Secretory Expression of Human Growth Hormone (hGH) Fused with N-Terminal Amino Acid Residues of Mature Cell Surface Layer Protein CspB of *Corynebacterium glutamicum* ATCC 13869 in *Corynebacterium glutamicum* YDK010 Strain The *C. glutamicum* YDK010 strain described in WO2004/029254 was transformed with pPS-hGH and pPK-hGH constructed in Example 4(1), which are plasmids for secretory expression of the human growth hormone hGH using the signal sequence of CspA of *C. ammoniagenes* (*C. stationis*) ATCC 6872 and the signal sequence of CspB of *C. glutamicum* ATCC 13869, respectively, pPKK6Xa-hGH, pPKK17Xa-hGH, and pPKK50Xa-hGH constructed in Example 4(2), which are plasmids for secretory expression of hGH fused with the N-terminal amino acid residues of the CspB mature protein linked to the signal sequence of CspB of *C. glutamicum* ATCC 13869, and pPSK6Xa-hGH, pPSK17Xa-hGH, and pPSK50Xa-hGH constructed in Example 4(3), which are plasmids for secretory expression of hGH fused with the N-terminal amino acid residues of the CspB mature protein linked to the signal sequence of CspA of *C. ammoniagenes* (*C. stationis*) ATCC 6872. Each of the obtained transformants was cultured in the MM liquid medium (120 g of glucose, 3 g of magnesium sulfate heptahydrate, 30 g of ammonium sulfate, 1.5 g of potassium dihydrogenphosphate, 0.03 g of iron sulfate heptahydrate, 0.03 g of manganese sulfate tetrahydrate, 0.45 mg of thiamine hydrochloride, 0.45 mg of biotin, 0.15 g of DL-methionine, and 50 g of calcium carbonate made into a volume of 1 L with water, and adjusted to pH 7.0) containing 25 mg/l of kanamycin at 30° C. for 72 hours. After completion of the culture, the culture supernatant obtained by centrifuging each culture broth was subjected to reduced SDS-PAGE, and then staining was performed with CBB R-250 (Bio-Rad). As a result, any band of the objective protein was not detected for the strains harboring pPS-hGH and pPK-hGH, while a band of the objective fusion protein was detected for all the YDK010 strains harboring pPKK6Xa-hGH, pPKK17Xa-hGH, pPKK50Xa-hGH, pPSK6Xa-hGH, pPSK17Xa-hGH, and pPSK50Xa-hGH, which are plasmids for expression of fusion hGH with the N-terminal amino acid residues of the mature CspB, regardless of the difference of the signal sequence (FIGS. 2 and 3). Further, when it was attempted to determine the N-terminal amino acid sequences of the fusion proteins for which improvement of the secretion amount was confirmed by using the protein sequencer PPSQ-21A (Shimadzu), the N-terminal amino acid residues of these fusion proteins could not be determined. Therefore, in consideration of the results mentioned later, it was confirmed that the N-terminal amino acid residues of these fusion proteins were converted into pyroglutamic acid residues.

(5) Secretory Expression of Human Growth Hormone (hGH) Fused with N-Terminal Amino Acid Residues of Mature Cell Surface Layer Protein CspB of *Corynebacterium glutamicum* ATCC 13869 in *Corynebacterium glutamicum* ATCC 13032 and *Corynebacterium ammoniagenes* (*C. stationis*) ATCC 6872

Figure 4:
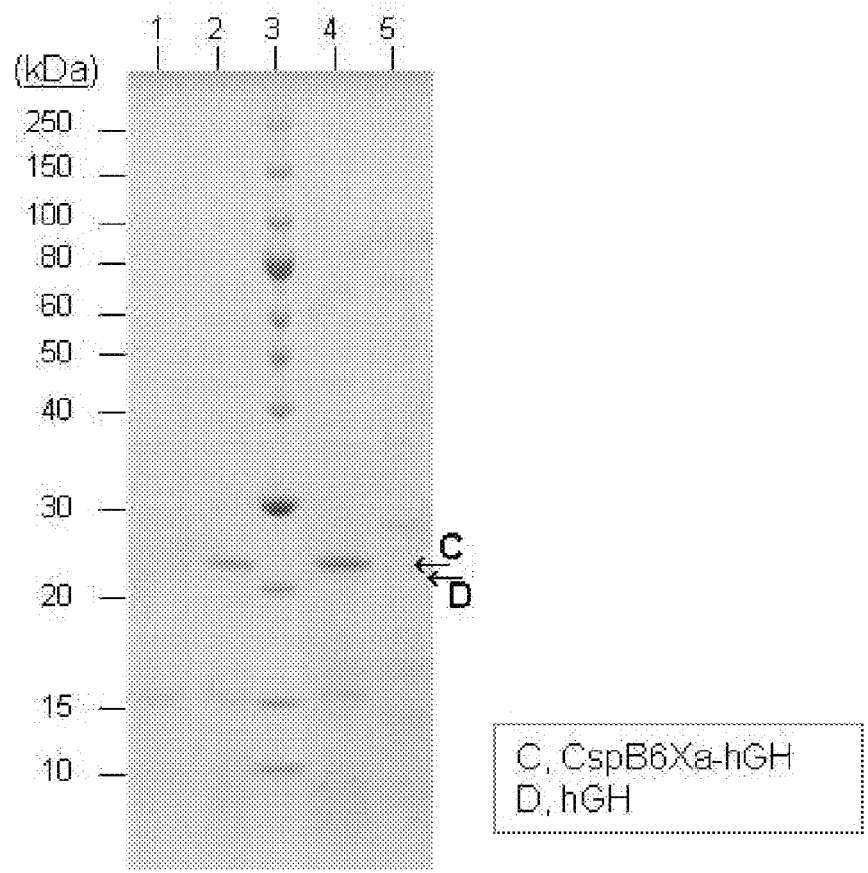
FIG. 4 is a photograph showing the results of SDS-PAGE of human growth hormone (hGH) fused with the signal sequence of CspB of *C. glutamicum* ATCC 13869, an N-terminal sequence of the mature CspB of *C. glutamicum* ATCC 13869, and a protease recognition sequence, which was expressed in *C. glutamicum* ATCC 13032 or *C. glutamicum* ATCC 6872.

The *C. glutamicum* ATCC 13869 and *C. ammoniagenes* (*C. stationis*) ATCC 6872 strains were transformed with pPK-hGH constructed in Example 4(1), which is a plasmid for secretory expression of the human growth hormone (hGH) using the signal sequence of CspB of *C. glutamicum* ATCC 13869, and pPKK6Xa-hGH constructed in Example 4(2), which is a plasmid for secretory expression of hGH fused with the N-terminal amino acid residues of the CspB mature protein linked to the signal sequence of CspB of *C. glutamicum* ATCC 13869. Each of the obtained transformants was cultured in the MM liquid medium (120 g of glucose, 3 g of magnesium sulfate heptahydrate, 30 g of ammonium sulfate, 1.5 g of potassium dihydrogenphosphate, 0.03 g of iron sulfate heptahydrate, 0.03 g of manganese sulfate tetrahydrate, 0.45 mg of thiamine hydrochloride, 0.45 mg of biotin, 0.15 g of DL-methionine, and 50 g of calcium carbonate made into a volume of 1 L with water, and adjusted to pH 7.0) containing 25 mg/l of kanamycin at 30° C. for 72 hours. After completion of the culture, the culture supernatant obtained by centrifuging each culture broth was subjected to reduced SDS-PAGE, and then staining was performed with CBB R-250 (Bio-Rad). As a result, any band of the objective protein was not detected for the strains harboring pPK-hGH, while a band of the objective protein was detected for both the strains harboring pPKK6Xa-hGH, which is a plasmid for expression of fusion hGH with the N-terminal 6 amino acid residues of the mature CspB (FIG. 4). Further, when it was attempted to determine the N-terminal amino acid sequences of the fusion proteins for which improvement of the secretion amount was confirmed by using the protein sequencer PPSQ-21A (Shimadzu), the N-terminal amino acid residues of these fusion proteins could not be determined. Therefore, in consideration of the results mentioned later, it was confirmed that the N-terminal amino acid residues of these fusion proteins were converted into pyroglutamic acid residues.

(6) Construction of Plasmid for Secretory Expression of Human Growth Hormone (hGH) Fused with N-Terminal Amino Acid Residues of Mature Cell Surface Layer Protein CspA of *Corynebacterium ammoniagenes* (*C. stationis*) ATCC 6872 and Secretory Expression Thereof in *Corynebacterium glutamicum* YDK010 Strain The amino acid sequence of CspA, which is a major cell surface layer protein of *C. ammoniagenes* (*C. stationis*) ATCC 6872, has already been determined (Genbank Accession No. BAB62413.1). By PCR using pPSK6Xa-hGH constructed in Example 4(3) as the template and the synthetic DNAs shown in SEQ ID NOS: 12 and 77 as the primers, the CspB promoter region and the region coding for the signal peptide 25 amino acid residues of the N-terminus of CspA derived from *C. ammoniagenes* (*C. stationis*) ATCC 6872 were amplified. Further, by PCR using the plasmid pPS-hGH constructed in Example 4(1) as the template and the synthetic DNAs shown in SEQ ID NOS: 78 and 67 as the primers, the hGH gene region was amplified. Furthermore, by PCR using both the amplified DNA fragments (i.e. the fragment of the CspB promoter region and the region coding for the CspA signal peptide and the hGH gene fragment) as the template and the DNAs shown in SEQ ID NOS: 12 and 67 as the primers, a DNA fragment consisting of both the DNA fragments fused together was obtained. In the primers of SEQ ID NOS: 12 and 67, the recognition sequence for the restriction enzyme KpnI was designed. In the primers of SEQ ID NOS: 77 and 78, a sequence coding for the N-terminal sequence 6 amino acid residues of the mature CspA protein of *C. ammoniagenes* (*C. stationis*) ATCC 6872 as the sequence for constructing a fusion gene was designed. Thus, in the obtained fusion DNA fragment, a sequence coding for the N-terminal sequence 6 amino acid residues of the CspA mature protein was inserted between the region coding for the CspA signal peptide and the hGH gene. The amino acid sequence of the N-terminal 6 amino acid residues of the CspA mature protein is Ala-Glu-Lys-Thr-Pro-Ala (AEKTPA, SEQ ID NO: 107), and does not comprise Gln-Glu-Thr (QET). For PCR, Pyrobest DNA Polymerase (Takara Bio) was used, and the reaction conditions were according to the protocol recommended by the manufacturer. This DNA fragment was treated with the restriction enzyme KpnI, and then inserted into pPK4 described in Japanese Patent Laid-open (Kokai) No. 9-322774 at the KpnI site to obtain pPSS6-hGH.

Then, the *C. glutamicum* YDK010 strain described in WO2004/029254 was transformed with the constructed pPSS6-hGH, which is a plasmid for secretory expression of human growth hormone (hGH) fused with the N-terminal 6 amino acid residues of the CspA mature protein of *C. ammoniagenes* (*C. stationis*) ATCC 6872. The obtained transformant was cultured in the MM liquid medium (120 g of glucose, 3 g of magnesium sulfate heptahydrate, 30 g of ammonium sulfate, 1.5 g of potassium dihydrogenphosphate, 0.03 g of iron sulfate heptahydrate, 0.03 g of manganese sulfate tetrahydrate, 0.45 mg of thiamine hydrochloride, 0.45 mg of biotin, 0.15 g of DL-methionine, and 50 g of calcium carbonate made into a volume of 1 L with water, and adjusted to pH 7.0) containing 25 mg/l of kanamycin at 30° C. for 72 hours. After completion of the culture, the culture supernatant obtained by centrifuging the culture broth was subjected to reduced SDS-PAGE, and then staining was performed with CBB R-250 (Bio-Rad). As a result, any band of the objective protein was not detected for the strain harboring pPSS6-hGH.

Example 5

Secretory Expression of Insulin-Like Growth Factor hIGF-1 Fused with N-Terminal Amino Acid Residues of Mature Cell Surface Layer Protein CspB of *Corynebacterium glutamicum* ATCC 13869

Construction of Plasmids for Secretory Expression of Insulin-Like Growth Factor hIGF-1 Fused with N-Terminal Amino Acid Residues of Mature Cell Surface Layer Protein CspB of *Corynebacterium glutamicum* ATCC 13869

The amino acid sequence of the human insulin-like growth factor-1 (hIGF-1) has already been determined (J. Biol. Chem., 253(8), pp. 2769-76 (1978)). By PCR using the plasmid pPSIGFm described in Japanese Patent Laid-open (Kokai) No. 2008-271973, which carries the hIGF-1 gene constructed in consideration of the amino acid sequence of hIGF-1 and the codon frequencies in *C. glutamicum*, as the template and the synthetic DNAs shown in SEQ ID NOS: 79 and 80 as the primers, the hIGF-1 gene region was amplified. Then, by PCR using pPKK6PIns constructed in Example 1(2) as the template and the synthetic DNAs shown in SEQ ID NOS: 12 and 81 as the primers, the CspB promoter region and the region coding for the signal peptide 30 amino acid residues of the N-terminus of CspB and the N-terminal 6 amino acid residues of the CspB mature protein were amplified. Furthermore, by PCR using both the amplified DNA fragments (i.e. the hIGF-1 gene fragment and the fragment of the CspB promoter region and the region coding for the CspB signal peptide and the N-terminal amino acid sequence 6 residues of CspB) as the template and DNAs shown in SEQ ID NOS: 12 and 80 as the primers, a DNA fragment consisting of both the DNA fragments fused together was obtained. In the primers of SEQ ID NOS: 12 and 80, the recognition sequence for the restriction enzyme KpnI was designed. In the primers of SEQ ID NOS: 79 and 81, a sequence coding for the N-terminal amino acid residues of the CspB mature protein and a sequence coding for the N-terminal amino acid residues of hIGF-1 for constructing a fusion gene of the sequence coding for the N-terminal amino acid 6 residues of the CspB mature protein and the hIGF-1 gene were designed, respectively. For PCR, Pyrobest DNA Polymerase (Takara Bio) was used, and the reaction conditions were according to the protocol recommended by the manufacturer. This DNA fragment was treated with the restriction enzyme KpnI, and then inserted into pPK4 described in Japanese Patent Laid-open (Kokai) No. 9-322774 at the KpnI site to obtain pPKK61GFm.

Similarly, by PCR using pPSK6Xa-hGH constructed in Example 4(3) as the template and the synthetic DNAs shown in SEQ ID NOS: 12 and 81 as the primers, the CspB promoter region of *C. glutamicum* ATCC 13869, and the region coding for the signal peptide 25 amino acid residues of the N-terminus of CspA of *C. ammoniagenes* (*C. stationis*) ATCC 6872 and the N-terminal side 6 amino acid residues of the CspB mature protein of *C. glutamicum* ATCC 13869 were amplified. Further, by PCR using the plasmid pPSIGFm described in Japanese Patent Laid-open (Kokai) No. 2008 271973 as the template and the synthetic DNAs shown in SEQ ID NOS: 79 and 80 as primers, the hIGF-1 gene region was amplified. Furthermore, by PCR using both the amplified DNA fragments (i.e. the fragment of the CspB promoter region and the region coding for CspB signal peptide and the N-terminal 6 amino acid residues of the mature CspB and the hIGF-1 gene fragment) as the template and DNAs shown in SEQ ID NOS: 12 and 80 as the primers, a DNA fragment consisting of both the DNA fragments fused together was obtained. In the primers of SEQ ID NOS: 12 and 80, the recognition sequence for the restriction enzyme KpnI was designed. In the primers of SEQ ID NOS: 79 and 81, a sequence coding for the N-terminal amino acid residues of the CspB mature protein and a sequence coding for the N-terminal amino acid residues of hIGF-1 for constructing a fusion gene of the sequence coding for the N-terminal 6 amino acid residues of the CspB mature protein and the hIGF-1 gene were designed, respectively. For PCR, Pyrobest DNA Polymerase (Takara Bio) was used, and the reaction conditions were according to the protocol recommended by the manufacturer. This DNA fragment was treated with the restriction enzyme KpnI, and then inserted into pPK4 described in Japanese Patent Laid-open (Kokai) No. 9-322774 at the KpnI site to obtain pPSK61GFm. By nucleotide sequencing of the insertion fragment, construction of the expected fusion gene was confirmed. The nucleotide sequencing was performed by using BigDye (registered trademark) Terminator v3.1 Cycle Sequencing Kit (Applied Biosystems) and 3130 Genetic Analyzer (Applied Biosystems).

(2) Secretory Expression of Insulin-Like Growth Factor hIGF-1 Fused with N-Terminal Amino Acid Residues of Mature Cell Surface Layer Protein CspB of *Corynebacterium glutamicum* ATCC 13869 in *Corynebacterium glutamicum* YDK010 Strain The *C. glutamicum* YDK010 strain described in WO2004/029254 was transformed with pPSIGFm, which is a plasmid for secretory expression of insulin-like growth factor hIGF-1 described in Japanese Patent Laid-open (Kokai) No. 2008-271973, as well as pPKK61GFm and pPSK61GFm constructed in Example 5(1), which are plasmids for secretory expression of hIGF-1 fused with the N-terminal amino acid residues of the CspB mature protein. Each of the obtained transformants was cultured in the MM liquid medium (120 g of glucose, 3 g of magnesium sulfate heptahydrate, 30 g of ammonium sulfate, 1.5 g of potassium dihydrogenphosphate, 0.03 g of iron sulfate heptahydrate, 0.03 g of manganese sulfate tetrahydrate, 0.45 mg of thiamine hydrochloride, 0.45 mg of biotin, 0.15 g of DL-methionine, and 50 g of calcium carbonate made into a volume of 1 L with water, and adjusted to pH 7.0) containing 25 mg/l of kanamycin at 30° C. for 72 hours. After completion of the culture, the culture supernatant obtained by centrifuging each culture broth was subjected to reduced SDS-PAGE, and then staining was performed with CBB R-250 (Bio-Rad). As a result, a band of a fusion protein having the intended molecular weight was definitely detected for both the strains introduced with the plasmids pPKK61GFm and pPSK61GFm, and thus it was confirmed that the secretion amount significantly increased compared with that observed with the pPSIGFm-introduced strain that expresses hIGF-1 not fused with the N-terminal amino acid residues of the mature CspB. Furthermore, the secretion amounts were quantified by using a densitometer. As a result, it was confirmed that the secretion amount of hIGF-1 increased for both the strains introduced with the plasmids of pPKK61GFm and pPSK61GFm that express hIGF-1 fused with the N-terminal amino acid residues of the mature CspB compared with the pPSIGFm-introduced strain (Table 4). Further, when it was attempted to determine the N-terminal amino acid sequences of these fusion proteins for which improvement of the secretion amount was confirmed by using the protein sequencer PPSQ-21A (Shimadzu), the N-terminal amino acid residues of these fusion proteins could not be determined. Therefore, in consideration of the results mentioned later, it was confirmed that the N-terminal amino acid residues of these fusion proteins were converted into pyroglutamic acid residues.

TABLE 4

| Strains | Secretion amount (%) |
|---|---|
| YDK010/pPSIGFm | 100.0 |
| YDK010/pPKK6IGFm | 431.5 |
| YDK010/pPSK6IGFm | 284.6 |

Example 6

Secretory Expression of Physiologically Active Peptide, Teriparatide, Fused with N-Terminal Amino Acid Residues of Mature Cell Surface Layer Protein CspB of *Corynebacterium glutamicum* ATCC 13869

Total Synthesis of Physiologically Active Peptide, Teriparatide, and Construction of Plasmid for Secretory Expression of Physiologically Active Peptide, Teriparatide, in *Corynebacterium glutamicum*

The amino acid sequence of the mature human parathyroid hormone PTH has already been determined (Genbank Accession No. AAA60215.1). The peptide consisting of the N-terminal $1^{st}$ to $34^{th}$ residues of this human parathyroid hormone PTH is known as a physiologically active peptide, Teriparatide, having a physiological activity useful as a therapeutic agent for osteoporosis. In consideration of the amino acid sequence of this Teriparatide and the codon frequencies in *C. glutamicum*, the DNAs shown in SEQ ID NOS: 82 and 83 were synthesized. By PCR using these DNAs as the template and separately synthesized DNAs shown in SEQ ID NOS: 84 and 85 as the primers, the Teriparatide gene shown in SEQ ID NO: 86 was amplified. This DNA fragment was inserted into the cloning vector pHSG398 (Takara Bio) at the SmaI site to obtain pHSG-Teri. By PCR using this pHSG-Teri as the template and the DNAs shown in SEQ ID NOS: 84 and 85 as the primers, the Teriparatide gene region was amplified. Then, by PCR using pPKSPTG1 described in WO01/23591 (including the promoter region for CspB derived from the *C. glutamicum* ATCC 13869 strain, and a DNA coding for the signal peptide of CspA (SlpA) derived from the *C. ammoniagenes* (*C. stationis*) ATCC 6872 strain) and pPKPTG1 described in WO01/23591 (including the promoter region for CspB and a DNA coding for the signal peptide of CspB, both derived from the *C. glutamicum* ATCC 13869 strain) as the template and the primers shown in SEQ ID NOS: 12 and 87 or SEQ ID NOS: 12 and 88, the promoter region for CspB derived from the *C. glutamicum* ATCC 13869 strain and the region coding for the signal peptide of CspA derived from the *C. ammoniagenes* (*C. stationis*) ATCC 6872 strain or CspB derived from the *C. glutamicum* ATCC 13869 strain were amplified. Furthermore, by using both the amplified DNA fragments (i.e. the Teriparatide gene fragment and the fragment of the CspB promoter region and the region coding for each signal peptide) as the template and the DNAs shown in SEQ ID NOS: 12 and 85 as the primers, DNA fragments of about 0.8 kbp each consisting of both the DNA fragments fused together were obtained. In the primers of SEQ ID NOS: 12 and 85, the recognition sequence for the restriction enzyme KpnI was designed. In the primers of SEQ ID NOS: 87 and 88, a sequence coding for the N-terminal amino acid residues of Teriparatide for constructing a fusion gene of the region coding for each signal peptide and the Teriparatide gene was designed. For PCR, Pyrobest DNA Polymerase (Takara Bio) was used, and the reaction conditions were according to the protocol recommended by the manufacturer. These DNA fragments were treated with the restriction enzyme KpnI, and then inserted into pPK4 described in Japanese Patent Laid-open (Kokai) No. 9-322774 at the KpnI site to obtain pPS-Teri and pPK-Teri, respectively.

Then, the Teriparatide gene region was amplified by PCR using pHSG-Teri mentioned above as the template and DNAs shown in SEQ ID NOS: 89 and 85 as the primers. Further, by PCR using pPKK6Xa-hGH constructed in Example 4(2) as the template and the primers shown in SEQ ID NOS: 12 and 90, the CspB promoter region and the region coding for the signal peptide 30 amino acid residues of the N-terminus of CspB, the N-terminal 6 amino acid residues of the CspB mature protein, and the recognition sequence of the factor Xa protease (IEGR) were amplified. Furthermore, by PCR using both the amplified DNA fragments (i.e. the Teriparatide gene fragment and the fragment of the CspB promoter region, and the region coding for the signal peptide of CspB, the N-terminal 6 amino acid residues of the CspB mature protein, and IEGR) as the template and DNAs shown in SEQ ID NOS: 12 and 85 as the primers, a DNA fragment of about 0.8 kbp consisting of both the DNA fragments fused together was obtained. In the primers of SEQ ID NOS: 12 and 85, the recognition sequence for the restriction enzyme KpnI was designed. In the primer of SEQ ID NO: 89, a sequence coding for the recognition sequence of the factor Xa protease (IEGR) for constructing a fusion gene of the region coding for the recognition sequence of the factor Xa protease (IEGR) and the Teriparatide gene was designed. For PCR, Pyrobest DNA Polymerase (Takara Bio) was used, and the reaction conditions were according to the protocol recommended by the manufacturer. This DNA fragment was treated with the restriction enzyme KpnI, and then inserted into pPK4 described in Japanese Patent Laid-open (Kokai) No. 9-322774 at the KpnI site to obtain pPKK6Xa-Teri. By nucleotide sequencing of the insertion fragment, construction of the expected fusion gene was confirmed. The nucleotide sequencing was performed by using BigDye (registered trademark) Terminator v3.1 Cycle Sequencing Kit (Applied Biosystems) and 3130 Genetic Analyzer (Applied Biosystems).

Figure 5:
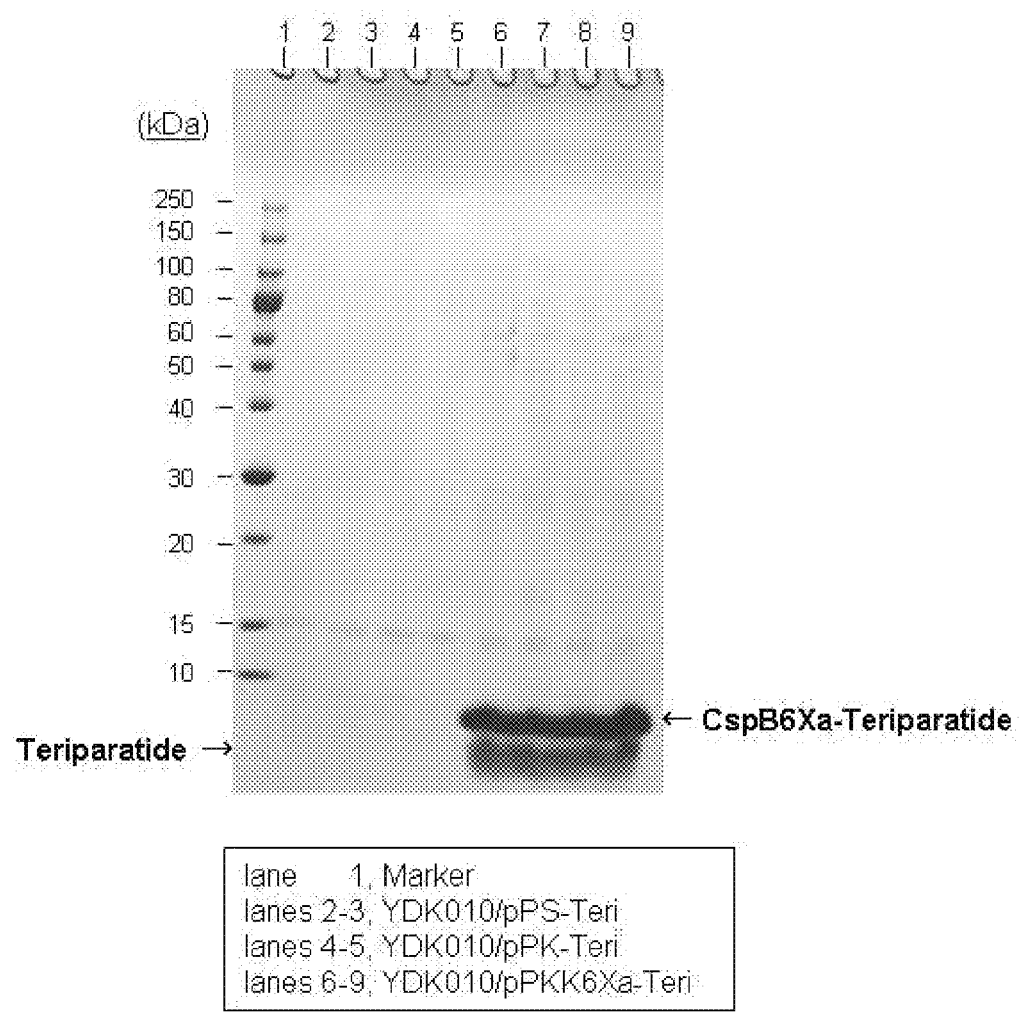
FIG. 5 is a photograph showing the results of SDS-PAGE of a physiologically active peptide, Teriparatide, fused with the signal sequence of CspB of *C. glutamicum* ATCC 13869, an N-terminal sequence of the mature CspB of *C. glutamicum* ATCC 13869, and a protease recognition sequence, which was expressed in the *C. glutamicum* YDK010 strain.

(2) Secretory Expression of Physiologically Active Peptide, Teriparatide, Fused with N-Terminal Amino Acid Residues of Mature Cell Surface Layer Protein CspB of *Corynebacterium glutamicum* ATCC 13869 in *Corynebacterium glutamicum* YDK010 Strain The *C. glutamicum* YDK010 strain described in WO2004/029254 was transformed with pPS-Teri and pPK-Teri constructed in Example 6(1), which are plasmids for secretory expression of the physiologically active peptide, Teriparatide, using the signal sequence of CspA of *C. ammoniagenes* (*C. stationis*) ATCC 6872 and the signal sequence of CspB of *C. glutamicum* ATCC 13032, respectively, as well as pPKK6Xa-Teri constructed in Example 6(1), which is a plasmid for secretory expression of Teriparatide fused with the N-terminal 6 amino acid residues of the mature protein of CspB linked to the signal sequence of CspB of *C. glutamicum* ATCC 13032. Each of the obtained transformants was cultured in the MM liquid medium (120 g of glucose, 3 g of magnesium sulfate heptahydrate, 30 g of ammonium sulfate, 1.5 g of potassium dihydrogenphosphate, 0.03 g of iron sulfate heptahydrate, 0.03 g of manganese sulfate tetrahydrate, 0.45 mg of thiamine hydrochloride, 0.45 mg of biotin, 0.15 g of DL-methionine, and 50 g of calcium carbonate made into a volume of 1 L with water, and adjusted to pH 7.0) containing 25 mg/l of kanamycin at 30° C. for 72 hours. After completion of the culture, the culture supernatant obtained by centrifuging each culture broth was subjected to reduced SDS-PAGE, and then staining was performed with CBB R-250 (Bio-Rad). As a result, any band of the objective protein was not detected for the strains harboring pPS-Teri and pPK-Teri, while a band of the objective protein was detected for the YDK010 strain harboring pPKK6Xa-Teri, which is a plasmid for expression of fusion Teriparatide with the N-terminal amino acid residues of CspB (FIG. 5). Further, when it was attempted to determine the N-terminal amino acid sequence of the fusion protein for which improvement of the secretion amount was confirmed by using the protein sequencer PPSQ-21A (Shimadzu), the N-terminal amino acid residues of the fusion protein could not be determined. However, when the fusion protein was treated with pyroglutamate aminopeptidase, and then the N-terminal amino acid sequence thereof was determined by using the protein sequencer PPSQ-21A (Shimadzu), the N-terminal amino acid sequence of the second and subsequent amino acid residues of the objective fusion protein could be read. Therefore, it could be confirmed that the objective fusion Teriparatide of which N-terminal amino acid residue was pyroglutamated was produced in the culture supernatant through secretory expression.

INDUSTRIAL APPlICABILITY

According to the present invention, heterologous proteins such as industrially useful proteins can be efficiently produced by secretory production.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

EXPLANATION OF SEQUENCE LISTING

SEQ ID NOS: 1 to 8: Nucleotide sequences of DNAs for total synthesis of proinsulin
SEQ ID NOS: 9 and 10: Primers
SEQ ID NO: 11: Nucleotide sequence of proinsulin gene
SEQ ID NOS: 12 to 51: Primers
SEQ ID NOS: 52 to 65: Nucleotide sequences of DNAs for total synthesis of human growth hormone (hGH) SEQ ID NOS: 66 and 67: Primers
SEQ ID NO: 68: Nucleotide sequence of hGH gene
SEQ ID NOS: 69 to 85: Primers
SEQ ID NO: 86: Nucleotide sequence of Teriparatide gene
SEQ ID NOS: 87 to 90: Primers
SEQ ID NO: 91: Amino acid sequence of signal peptide of PS1 derived from *C. glutamicum*
SEQ ID NO: 92: Amino acid sequence of signal peptide of PS2 (CspB) derived from *C. glutamicum*
SEQ ID NO: 93: Amino acid sequence of signal peptide of SlpA (CspA) of *C. ammoniagenes* (*C. stationis*)
SEQ ID NO: 94: Nucleotide sequence of cspB gene of *C. glutamicum* ATCC 13869
SEQ ID NO: 95: Amino acid sequence of CspB protein of *C. glutamicum* ATCC 13869
SEQ ID NO: 96: Amino acid sequence of CspB mature protein of *C. glutamicum* ATCC 13869
SEQ ID NOS: 97 to 101: Amino acid sequences of N-terminal 6 amino acid residues of mature proteins of CspB homologues derived from *C. glutamicum*
SEQ ID NOS: 102 to 104: Amino acid sequences of insertion sequence used in the present invention in one embodiment
SEQ ID NO: 105: Recognition sequence of factor Xa protease
SEQ ID NO: 106: Recognition sequence of ProTEV protease
SEQ ID NO: 107: Amino acid sequence of N-terminal 6 amino acid residues of CspA mature protein of *C. ammoniagenes* (*C. stationis*) ATCC 6872

The invention claimed is:

1. A method for producing a heterologous protein comprising:
   A) culturing a coryneform bacterium having a genetic construct for secretory expression of a heterologous protein;
   B) allowing the bacterium to produce and secrete the heterologous protein, and
   C) collecting the heterologous protein,
   wherein the genetic construct comprises:
   i) a promoter sequence that functions in the coryneform bacterium,
   ii) a first nucleic acid sequence coding for a signal peptide that functions in the coryneform bacterium, wherein said first nucleic acid sequence is ligated downstream from the promoter sequence, and
   iii) a second nucleic acid sequence coding for a fusion protein having:
      a) an amino acid sequence comprising Gln-Glu-Thr, and
      b) the heterologous protein,
   wherein said second nucleic acid sequence is ligated downstream from the first nucleic acid sequence coding for the signal peptide, and
   wherein the amino acid sequence comprising Gln-Glu-Thr does not consist of an amino acid sequence consisting of the amino acid residues at positions 1 to 14 or positions 1 to 38 of SEQ ID NO: 96.

2. The method according to claim 1, wherein the amino acid sequence comprising Gln-Glu-Thr is selected from the group consisting of:
   (A) Gln-Glu-Thr
   (B) Gln-Glu-Thr-Xaa1 (SEQ ID NO: 102)
   (C) Gln-Glu-Thr-Xaa1-Xaa2 (SEQ ID NO: 103)
   (D) Gln-Glu-Thr-Xaa1-Xaa2-Xaa3 (SEQ ID NO: 104)
   (E) an amino acid sequence consisting of Gln-Glu-Thr fused with the amino acid residues at positions 4 to 7 of a mature CspB protein,
   (F) an amino acid sequence consisting of Gln-Glu-Thr fused with the amino acid residues at positions 4 to 8 of a mature CspB protein,
   (G) an amino acid sequence consisting of Gln-Glu-Thr fused with the amino acid residues at positions 4 to 17 of a mature CspB protein,
   (H) an amino acid sequence consisting of Gln-Glu-Thr fused with the amino acid residues at positions 4 to 50 of a mature CspB protein,
   wherein Xaa1 is Asn, Gly, Thr, Pro, or Ala; Xaa2 is Pro, Thr, or Val; and Xaa3 is Thr or Tyr.

3. The method according to claim 2, wherein the amino acid sequence comprising Gln-Glu-Thr is selected from the group consisting of Gln-Glu-Thr-Asn-Pro-Thr (SEQ ID NO: 97), Gln-Glu-Thr-Gly-Thr-Tyr (SEQ ID NO: 98), Gln-Glu-Thr-Thr-Val-Thr (SEQ ID NO: 99), Gln-Glu-Thr-Pro-Val-Thr (SEQ ID NO: 100), and Gln-Glu-Thr-Ala-Val-Thr (SEQ ID NO: 101).

4. The method according to claim 1, wherein the genetic construct further comprises a third nucleic acid sequence coding for an amino acid sequence capable of enzymatic digestion between the amino acid sequence comprising Gln-Glu-Thr and the heterologous protein.

5. The method according to claim 4, wherein the amino acid sequence capable of enzymatic digestion is a recognition sequence of factor Xa protease, or a recognition sequence of ProTEV protease.

6. The method according to claim 5, wherein the recognition sequence is the amino acid sequence shown in SEQ ID NO: 105 or 106.

7. The method according to claim 1, wherein the signal peptide that functions in the coryneform bacterium is the signal peptide of CspB derived from a coryneform bacterium.

8. The method according to claim 7, wherein the signal peptide of CspB has the amino acid sequence shown in SEQ ID NO: 92.

9. The method according to claim 1, wherein the coryneform bacterium belongs to the genus *Corynebacterium* or *Brevibacterium*.

10. The method according to claim 1, wherein the coryneform bacterium is *Corynebacterium glutamicum* or *Corynebacterium stationis*.

* * * * *

SEQUENCE LISTING

```
<160> NUMBER OF SEQ ID NOS: 107

<210> SEQ ID NO 1
<211> LENGTH: 60
<212> TYPE: DNA
<213> ORGANISM: Artificial Sequence
<220> FEATURE:
<223> OTHER INFORMATION: PIns

<400> SEQUENCE: 1
atggcgctct ggatgcgcct gctgccactc ctggcgctcc tggcactgtg gggaccagat    60

<210> SEQ ID NO 2
<211> LENGTH: 60
<212> TYPE: DNA
<213> ORGANISM: Artificial Sequence
<220> FEATURE:
<223> OTHER INFORMATION: PIns

<400> SEQUENCE: 2
gggagccgca aagatgttgg ttcacgaagg cggcagcagg atctggtccc cacagtgcca    60

<210> SEQ ID NO 3
<211> LENGTH: 60
<212> TYPE: DNA
<213> ORGANISM: Artificial Sequence
```

```
<220> FEATURE:
<223> OTHER INFORMATION: PIns

<400> SEQUENCE: 3
ccaacatctt tgcggctccc acttggtgga ggcgctgtac cttgtctgcg gagagcgcgg      60

<210> SEQ ID NO 4
<211> LENGTH: 60
<212> TYPE: DNA
<213> ORGANISM: Artificial Sequence
<220> FEATURE:
<223> OTHER INFORMATION: PIns

<400> SEQUENCE: 4
atcttcggct tcgcgacgag tcttaggggt atagaagaat ccgcgctctc cgcagacaag      60

<210> SEQ ID NO 5
<211> LENGTH: 60
<212> TYPE: DNA
<213> ORGANISM: Artificial Sequence
<220> FEATURE:
<223> OTHER INFORMATION: PIns

<400> SEQUENCE: 5
ctcgtcgcga agccgaagat ctgcaggttg gtcaggtcga actgggcggc ggccctggtg      60

<210> SEQ ID NO 6
<211> LENGTH: 60
<212> TYPE: DNA
<213> ORGANISM: Artificial Sequence
<220> FEATURE:
<223> OTHER INFORMATION: PIns

<400> SEQUENCE: 6
tgcaaggagc cttccagggc gagtggctgg agggagccgg caccagggcc gccgcccagt      60

<210> SEQ ID NO 7
<211> LENGTH: 60
<212> TYPE: DNA
<213> ORGANISM: Artificial Sequence
<220> FEATURE:
<223> OTHER INFORMATION: PIns

<400> SEQUENCE: 7
gccctggaag gctccttgca aaaacgcgga atcgtggagc agtgctgtac cagcatctgc      60

<210> SEQ ID NO 8
<211> LENGTH: 53
<212> TYPE: DNA
<213> ORGANISM: Artificial Sequence
<220> FEATURE:
<223> OTHER INFORMATION: PIns

<400> SEQUENCE: 8
tcagttgcag tagttctcaa gttggtagag ggagcagatg ctggtacagc act             53

<210> SEQ ID NO 9
<211> LENGTH: 25
<212> TYPE: DNA
<213> ORGANISM: Artificial Sequence
<220> FEATURE:
<223> OTHER INFORMATION: primer

<400> SEQUENCE: 9
ttcgtgaacc aacatctttg cggct                                            25
```

<210> SEQ ID NO 10
<211> LENGTH: 34
<212> TYPE: DNA
<213> ORGANISM: Artificial Sequence
<220> FEATURE:
<223> OTHER INFORMATION: primer

<400> SEQUENCE: 10
gcctctagat cagttgcagt agttctcaag ttgg       34

<210> SEQ ID NO 11
<211> LENGTH: 261
<212> TYPE: DNA
<213> ORGANISM: Artificial Sequence
<220> FEATURE:
<223> OTHER INFORMATION: PIns

<400> SEQUENCE: 11
ttcgtgaacc aacatctttg cggctcccac ttggtggagg cgctgtacct tgtctgcgga        60
gagcgcggat tcttctatac ccctaagact cgtcgcgaag ccgaagatct gcaggttggt       120
caggtcgaac tgggcggcgg ccctggtgcc ggctccctcc agccactcgc cctggaaggc       180
tccttgcaaa aacgcggaat cgtggagcag tgctgtacca gcatctgctc cctctaccaa       240
cttgagaact actgcaactg a                                                 261

<210> SEQ ID NO 12
<211> LENGTH: 28
<212> TYPE: DNA
<213> ORGANISM: Artificial Sequence
<220> FEATURE:
<223> OTHER INFORMATION: primer

<400> SEQUENCE: 12
ggcggtaccc aaattcctgt gaagtagc       28

<210> SEQ ID NO 13
<211> LENGTH: 46
<212> TYPE: DNA
<213> ORGANISM: Artificial Sequence
<220> FEATURE:
<223> OTHER INFORMATION: primer

<400> SEQUENCE: 13
ccgcaaagat gttggttcac gaaagcgaat gctgggatag ctacgc       46

<210> SEQ ID NO 14
<211> LENGTH: 25
<212> TYPE: DNA
<213> ORGANISM: Artificial Sequence
<220> FEATURE:
<223> OTHER INFORMATION: primer

<400> SEQUENCE: 14
gatgtcggaa gaaccggttc ccttg       25

<210> SEQ ID NO 15
<211> LENGTH: 46
<212> TYPE: DNA
<213> ORGANISM: Artificial Sequence
<220> FEATURE:
<223> OTHER INFORMATION: primer

<400> SEQUENCE: 15
ccgcaaagat gttggttcac gaactgagcg aatgctggga tagcta       46

<210> SEQ ID NO 16
<211> LENGTH: 46
<212> TYPE: DNA
<213> ORGANISM: Artificial Sequence
<220> FEATURE:
<223> OTHER INFORMATION: primer

<400> SEQUENCE: 16
ccgcaaagat gttggttcac gaactcctga gcgaatgctg ggatag      46

<210> SEQ ID NO 17
<211> LENGTH: 46
<212> TYPE: DNA
<213> ORGANISM: Artificial Sequence
<220> FEATURE:
<223> OTHER INFORMATION: primer

<400> SEQUENCE: 17
ccgcaaagat gttggttcac gaaggtctcc tgagcgaatg ctggga      46

<210> SEQ ID NO 18
<211> LENGTH: 46
<212> TYPE: DNA
<213> ORGANISM: Artificial Sequence
<220> FEATURE:
<223> OTHER INFORMATION: primer

<400> SEQUENCE: 18
ccgcaaagat gttggttcac gaagttggtc tcctgagcga atgctg      46

<210> SEQ ID NO 19
<211> LENGTH: 46
<212> TYPE: DNA
<213> ORGANISM: Artificial Sequence
<220> FEATURE:
<223> OTHER INFORMATION: primer

<400> SEQUENCE: 19
ccgcaaagat gttggttcac gaatgggttg gtctcctgag cgaatg      46

<210> SEQ ID NO 20
<211> LENGTH: 46
<212> TYPE: DNA
<213> ORGANISM: Artificial Sequence
<220> FEATURE:
<223> OTHER INFORMATION: primer

<400> SEQUENCE: 20
ccgcaaagat gttggttcac gaaggttggg ttggtctcct gagcga      46

<210> SEQ ID NO 21
<211> LENGTH: 46
<212> TYPE: DNA
<213> ORGANISM: Artificial Sequence
<220> FEATURE:
<223> OTHER INFORMATION: primer

<400> SEQUENCE: 21
ccgcaaagat gttggttcac gaagaaggtt gggttggtct cctgag      46

<210> SEQ ID NO 22
<211> LENGTH: 46
<212> TYPE: DNA
<213> ORGANISM: Artificial Sequence
<220> FEATURE:

<223> OTHER INFORMATION: primer

<400> SEQUENCE: 22
ccgcaaagat gttggttcac gaagttgaag gttgggttgg tctcct    46

<210> SEQ ID NO 23
<211> LENGTH: 46
<212> TYPE: DNA
<213> ORGANISM: Artificial Sequence
<220> FEATURE:
<223> OTHER INFORMATION: primer

<400> SEQUENCE: 23
ccgcaaagat gttggttcac gaagatgttg aaggttgggt tggtct    46

<210> SEQ ID NO 24
<211> LENGTH: 46
<212> TYPE: DNA
<213> ORGANISM: Artificial Sequence
<220> FEATURE:
<223> OTHER INFORMATION: primer

<400> SEQUENCE: 24
ccgcaaagat gttggttcac gaagttgatg ttgaaggttg ggttgg    46

<210> SEQ ID NO 25
<211> LENGTH: 46
<212> TYPE: DNA
<213> ORGANISM: Artificial Sequence
<220> FEATURE:
<223> OTHER INFORMATION: primer

<400> SEQUENCE: 25
ccgcaaagat gttggttcac gaagttgttg atgttgaagg ttgggt    46

<210> SEQ ID NO 26
<211> LENGTH: 46
<212> TYPE: DNA
<213> ORGANISM: Artificial Sequence
<220> FEATURE:
<223> OTHER INFORMATION: primer

<400> SEQUENCE: 26
ccgcaaagat gttggttcac gaagccgttg ttgatgttga aggttg    46

<210> SEQ ID NO 27
<211> LENGTH: 46
<212> TYPE: DNA
<213> ORGANISM: Artificial Sequence
<220> FEATURE:
<223> OTHER INFORMATION: primer

<400> SEQUENCE: 27
ccgcaaagat gttggttcac gaagaagccg ttgttgatgt tgaagg    46

<210> SEQ ID NO 28
<211> LENGTH: 46
<212> TYPE: DNA
<213> ORGANISM: Artificial Sequence
<220> FEATURE:
<223> OTHER INFORMATION: primer

<400> SEQUENCE: 28
ccgcaaagat gttggttcac gaagttgaag ccgttgttga tgttga    46

```
<210> SEQ ID NO 29
<211> LENGTH: 46
<212> TYPE: DNA
<213> ORGANISM: Artificial Sequence
<220> FEATURE:
<223> OTHER INFORMATION: primer

<400> SEQUENCE: 29
ccgcaaagat gttggttcac gaaatcgttg aagccgttgt tgatgt        46

<210> SEQ ID NO 30
<211> LENGTH: 46
<212> TYPE: DNA
<213> ORGANISM: Artificial Sequence
<220> FEATURE:
<223> OTHER INFORMATION: primer

<400> SEQUENCE: 30
ccgcaaagat gttggttcac gaaatcagca tcgttgaagc cgttgt        46

<210> SEQ ID NO 31
<211> LENGTH: 46
<212> TYPE: DNA
<213> ORGANISM: Artificial Sequence
<220> FEATURE:
<223> OTHER INFORMATION: primer

<400> SEQUENCE: 31
ccgcaaagat gttggttcac gaaggtggat ccatcagcat cgttga        46

<210> SEQ ID NO 32
<211> LENGTH: 46
<212> TYPE: DNA
<213> ORGANISM: Artificial Sequence
<220> FEATURE:
<223> OTHER INFORMATION: primer

<400> SEQUENCE: 32
ccgcaaagat gttggttcac gaagtactgg aactcttcca ggtaag        46

<210> SEQ ID NO 33
<211> LENGTH: 46
<212> TYPE: DNA
<213> ORGANISM: Artificial Sequence
<220> FEATURE:
<223> OTHER INFORMATION: primer

<400> SEQUENCE: 33
ccgcaaagat gttggttcac gaaagtgatg gtctcagcgg aagccg        46

<210> SEQ ID NO 34
<211> LENGTH: 46
<212> TYPE: DNA
<213> ORGANISM: Artificial Sequence
<220> FEATURE:
<223> OTHER INFORMATION: primer

<400> SEQUENCE: 34
ccgcaaagat gttggttcac gaactctgca aagtcagtct tgttct        46

<210> SEQ ID NO 35
<211> LENGTH: 46
<212> TYPE: DNA
<213> ORGANISM: Artificial Sequence
<220> FEATURE:
<223> OTHER INFORMATION: primer
```

```
<400> SEQUENCE: 35
ccgcaaagat gttggttcac gaattcattg ttatcaattg cgaact            46

<210> SEQ ID NO 36
<211> LENGTH: 46
<212> TYPE: DNA
<213> ORGANISM: Artificial Sequence
<220> FEATURE:
<223> OTHER INFORMATION: primer

<400> SEQUENCE: 36
ccgcaaagat gttggttcac gaagagctgg ggaaccagaa cgtcag            46

<210> SEQ ID NO 37
<211> LENGTH: 46
<212> TYPE: DNA
<213> ORGANISM: Artificial Sequence
<220> FEATURE:
<223> OTHER INFORMATION: primer

<400> SEQUENCE: 37
ccgcaaagat gttggttcac gaagatcagg gaagagtagt gctggc            46

<210> SEQ ID NO 38
<211> LENGTH: 46
<212> TYPE: DNA
<213> ORGANISM: Artificial Sequence
<220> FEATURE:
<223> OTHER INFORMATION: primer

<400> SEQUENCE: 38
ccgcaaagat gttggttcac gaagatagcg aagtcgagct tagcct            46

<210> SEQ ID NO 39
<211> LENGTH: 46
<212> TYPE: DNA
<213> ORGANISM: Artificial Sequence
<220> FEATURE:
<223> OTHER INFORMATION: primer

<400> SEQUENCE: 39
ccgcaaagat gttggttcac gaagcggagc tgctcagcgc ggtatg            46

<210> SEQ ID NO 40
<211> LENGTH: 46
<212> TYPE: DNA
<213> ORGANISM: Artificial Sequence
<220> FEATURE:
<223> OTHER INFORMATION: primer

<400> SEQUENCE: 40
ccgcaaagat gttggttcac gaagatgtcg gaagaaccgg ttccct            46

<210> SEQ ID NO 41
<211> LENGTH: 34
<212> TYPE: DNA
<213> ORGANISM: Artificial Sequence
<220> FEATURE:
<223> OTHER INFORMATION: primer

<400> SEQUENCE: 41
gccggtacct cagttgcagt agttctcaag ttgg                         34

<210> SEQ ID NO 42
<211> LENGTH: 46
```

```
<212> TYPE: DNA
<213> ORGANISM: Artificial Sequence
<220> FEATURE:
<223> OTHER INFORMATION: primer

<400> SEQUENCE: 42
ccgcaaagat gttggttcac gaagtaagtt ccggtctcct gagcga         46

<210> SEQ ID NO 43
<211> LENGTH: 46
<212> TYPE: DNA
<213> ORGANISM: Artificial Sequence
<220> FEATURE:
<223> OTHER INFORMATION: primer

<400> SEQUENCE: 43
ccgcaaagat gttggttcac gaaggttaca gtggtttcct gagcga         46

<210> SEQ ID NO 44
<211> LENGTH: 46
<212> TYPE: DNA
<213> ORGANISM: Artificial Sequence
<220> FEATURE:
<223> OTHER INFORMATION: primer

<400> SEQUENCE: 44
ccgcaaagat gttggttcac gaaggttaca ggggtctcct gagcga         46

<210> SEQ ID NO 45
<211> LENGTH: 46
<212> TYPE: DNA
<213> ORGANISM: Artificial Sequence
<220> FEATURE:
<223> OTHER INFORMATION: primer

<400> SEQUENCE: 45
ccgcaaagat gttggttcac gaaggttaca gcggtctcct gagcga         46

<210> SEQ ID NO 46
<211> LENGTH: 46
<212> TYPE: DNA
<213> ORGANISM: Artificial Sequence
<220> FEATURE:
<223> OTHER INFORMATION: primer

<400> SEQUENCE: 46
tggttcacga agcggccctc gatggttggg ttggtctcct gagcga         46

<210> SEQ ID NO 47
<211> LENGTH: 46
<212> TYPE: DNA
<213> ORGANISM: Artificial Sequence
<220> FEATURE:
<223> OTHER INFORMATION: primer

<400> SEQUENCE: 47
acgaactgga agtacaggtt ttcggttggg ttggtctcct gagcga         46

<210> SEQ ID NO 48
<211> LENGTH: 35
<212> TYPE: DNA
<213> ORGANISM: Artificial Sequence
<220> FEATURE:
<223> OTHER INFORMATION: primer

<400> SEQUENCE: 48
```
atcgagggcc gcttcgtgaa ccaacatctt tgcgg                                   35

<210> SEQ ID NO 49
<211> LENGTH: 41
<212> TYPE: DNA
<213> ORGANISM: Artificial Sequence
<220> FEATURE:
<223> OTHER INFORMATION: primer

<400> SEQUENCE: 49
gaaaacctgt acttccagtt cgtgaaccaa catctttgcg g                            41

<210> SEQ ID NO 50
<211> LENGTH: 46
<212> TYPE: DNA
<213> ORGANISM: Artificial Sequence
<220> FEATURE:
<223> OTHER INFORMATION: primer

<400> SEQUENCE: 50
tggttcacga agcggccctc gatatcagca tcgttgaagc cgttgt                       46

<210> SEQ ID NO 51
<211> LENGTH: 46
<212> TYPE: DNA
<213> ORGANISM: Artificial Sequence
<220> FEATURE:
<223> OTHER INFORMATION: primer

<400> SEQUENCE: 51
tggttcacga agcggccctc gatgtactgg aactcttcca ggtaag                       46

<210> SEQ ID NO 52
<211> LENGTH: 60
<212> TYPE: DNA
<213> ORGANISM: Artificial Sequence
<220> FEATURE:
<223> OTHER INFORMATION: hGH

<400> SEQUENCE: 52
tttccaacaa tcccgctgag ccgcctcttc gataacgctt cgctccgcgc tcaccgcctg        60

<210> SEQ ID NO 53
<211> LENGTH: 60
<212> TYPE: DNA
<213> ORGANISM: Artificial Sequence
<220> FEATURE:
<223> OTHER INFORMATION: hGH

<400> SEQUENCE: 53
gtaccaggaa ttcgaggaag cgtatattcc caaggaacag aaatactcgt ttctccaaaa        60

<210> SEQ ID NO 54
<211> LENGTH: 60
<212> TYPE: DNA
<213> ORGANISM: Artificial Sequence
<220> FEATURE:
<223> OTHER INFORMATION: hGH

<400> SEQUENCE: 54
tttccgagtc gattcctacc ccctccaatc gtgaggaaac ccagcaaaaa agcaacctcg        60

<210> SEQ ID NO 55
<211> LENGTH: 60
<212> TYPE: DNA
<213> ORGANISM: Artificial Sequence

```
<220> FEATURE:
<223> OTHER INFORMATION: hGH

<400> SEQUENCE: 55
cttcttatcc agtcctggct ggagcccgtg cagttttttgc gcagcgtctt tgctaactct    60

<210> SEQ ID NO 56
<211> LENGTH: 60
<212> TYPE: DNA
<213> ORGANISM: Artificial Sequence
<220> FEATURE:
<223> OTHER INFORMATION: hGH

<400> SEQUENCE: 56
ttccaacgtg tacgatcttt tgaaggatct cgaagagggt attcagactc tgatgggccg    60

<210> SEQ ID NO 57
<211> LENGTH: 60
<212> TYPE: DNA
<213> ORGANISM: Artificial Sequence
<220> FEATURE:
<223> OTHER INFORMATION: hGH

<400> SEQUENCE: 57
gcacgggcca aattttcaag caaacctaca gcaaatttga tactaactcc cacaatgacg    60

<210> SEQ ID NO 58
<211> LENGTH: 60
<212> TYPE: DNA
<213> ORGANISM: Artificial Sequence
<220> FEATURE:
<223> OTHER INFORMATION: hGH

<400> SEQUENCE: 58
ggtctgctct actgcttctt caaggatatg gataaggtcg aaaccttcct ccgtatcgtg    60

<210> SEQ ID NO 59
<211> LENGTH: 60
<212> TYPE: DNA
<213> ORGANISM: Artificial Sequence
<220> FEATURE:
<223> OTHER INFORMATION: hGH

<400> SEQUENCE: 59
cttcctcgaa ttcctggtac gtgtcgaacg cgagttggtg caggcggtga gcgcggagcg    60

<210> SEQ ID NO 60
<211> LENGTH: 60
<212> TYPE: DNA
<213> ORGANISM: Artificial Sequence
<220> FEATURE:
<223> OTHER INFORMATION: hGH

<400> SEQUENCE: 60
ggtaggaatc gactcggaaa agcagaggct ggtttggggg ttttggagaa acgagtattt    60

<210> SEQ ID NO 61
<211> LENGTH: 60
<212> TYPE: DNA
<213> ORGANISM: Artificial Sequence
<220> FEATURE:
<223> OTHER INFORMATION: hGH

<400> SEQUENCE: 61
agccaggact ggataagaag cagtgagata cgcagcaact cgaggttgct tttttgctgg    60
```

-continued

<210> SEQ ID NO 62
<211> LENGTH: 60
<212> TYPE: DNA
<213> ORGANISM: Artificial Sequence
<220> FEATURE:
<223> OTHER INFORMATION: hGH

<400> SEQUENCE: 62
aaagatcgta cacgttggaa tccgacgctc catacacaag agagttagca aagacgctgc    60

<210> SEQ ID NO 63
<211> LENGTH: 60
<212> TYPE: DNA
<213> ORGANISM: Artificial Sequence
<220> FEATURE:
<223> OTHER INFORMATION: hGH

<400> SEQUENCE: 63
cttgaaaatt tggcccgtgc gaggcgatcc gtcttcgagg cggcccatca gagtctgaat    60

<210> SEQ ID NO 64
<211> LENGTH: 60
<212> TYPE: DNA
<213> ORGANISM: Artificial Sequence
<220> FEATURE:
<223> OTHER INFORMATION: hGH

<400> SEQUENCE: 64
aagaagcagt agagcagacc gtaattttc aacaaagcat cgtcattgtg ggagttagta    60

<210> SEQ ID NO 65
<211> LENGTH: 56
<212> TYPE: DNA
<213> ORGANISM: Artificial Sequence
<220> FEATURE:
<223> OTHER INFORMATION: hGH

<400> SEQUENCE: 65
tcagaaaccg cacgagccct ccactgagcg gcactgcacg atacggagga aggttt    56

<210> SEQ ID NO 66
<211> LENGTH: 23
<212> TYPE: DNA
<213> ORGANISM: Artificial Sequence
<220> FEATURE:
<223> OTHER INFORMATION: primer

<400> SEQUENCE: 66
tttccaacaa tcccgctgag ccg    23

<210> SEQ ID NO 67
<211> LENGTH: 31
<212> TYPE: DNA
<213> ORGANISM: Artificial Sequence
<220> FEATURE:
<223> OTHER INFORMATION: primer

<400> SEQUENCE: 67
gccggtacct cagaaaccgc acgagccctc c    31

<210> SEQ ID NO 68
<211> LENGTH: 585
<212> TYPE: DNA
<213> ORGANISM: Artificial Sequence
<220> FEATURE:
<223> OTHER INFORMATION: hGH

<400> SEQUENCE: 68

```
tttccaacaa tcccgctgag ccgcctcttc gataacgctt cgctccgcgc tcaccgcctg      60
caccaactcg cgttcgacac gtaccaggaa ttcgaggaag cgtatattcc caaggaacag     120
aaatactcgt ttctccaaaa cccccaaacc agcctctgct tttccgagtc gattcctacc     180
ccctccaatc gtgaggaaac ccagcaaaaa agcaacctcg agttgctgcg tatctcactg     240
cttcttatcc agtcctggct ggagcccgtg cagttttgc gcagcgtctt tgctaactct      300
cttgtgtatg gagcgtcgga ttccaacgtg tacgatcttt tgaaggatct cgaagagggt     360
attcagactc tgatgggccg cctcgaagac ggatcgcctc gcacgggcca aattttcaag     420
caaacctaca gcaaatttga tactaactcc cacaatgacg atgctttgtt gaaaaattac     480
ggtctgctct actgcttctt caaggatatg gataaggtcg aaaccttcct ccgtatcgtg     540
cagtgccgct cagtggaggg ctcgtgcggt ttctgaggta ccggc                     585
```

<210> SEQ ID NO 69
<211> LENGTH: 46
<212> TYPE: DNA
<213> ORGANISM: Artificial Sequence
<220> FEATURE:
<223> OTHER INFORMATION: primer

<400> SEQUENCE: 69

```
cggctcagcg ggattgttgg aaatgccgtt gccacaggtg cggcca                    46
```

<210> SEQ ID NO 70
<211> LENGTH: 46
<212> TYPE: DNA
<213> ORGANISM: Artificial Sequence
<220> FEATURE:
<223> OTHER INFORMATION: primer

<400> SEQUENCE: 70

```
cggctcagcg ggattgttgg aaagcgaatg ctgggatagc aacgcc                    46
```

<210> SEQ ID NO 71
<211> LENGTH: 46
<212> TYPE: DNA
<213> ORGANISM: Artificial Sequence
<220> FEATURE:
<223> OTHER INFORMATION: primer

<400> SEQUENCE: 71

```
cggctcagcg ggattgttgg aaagcggccc tcgatggttg ggttgg                    46
```

<210> SEQ ID NO 72
<211> LENGTH: 46
<212> TYPE: DNA
<213> ORGANISM: Artificial Sequence
<220> FEATURE:
<223> OTHER INFORMATION: primer

<400> SEQUENCE: 72

```
cggctcagcg ggattgttgg aaagcggccc tcgatatcag catcgt                    46
```

<210> SEQ ID NO 73
<211> LENGTH: 46
<212> TYPE: DNA
<213> ORGANISM: Artificial Sequence
<220> FEATURE:
<223> OTHER INFORMATION: primer

```
<400> SEQUENCE: 73
cggctcagcg ggattgttgg aaagcggccc tcgatgtact ggaact        46

<210> SEQ ID NO 74
<211> LENGTH: 46
<212> TYPE: DNA
<213> ORGANISM: Artificial Sequence
<220> FEATURE:
<223> OTHER INFORMATION: primer

<400> SEQUENCE: 74
tcgatggttg ggttggtctc ctgtgccgtt gccacaggtg cggcca        46

<210> SEQ ID NO 75
<211> LENGTH: 18
<212> TYPE: DNA
<213> ORGANISM: Artificial Sequence
<220> FEATURE:
<223> OTHER INFORMATION: primer

<400> SEQUENCE: 75
caggagacca acccaacc                                       18

<210> SEQ ID NO 76
<211> LENGTH: 46
<212> TYPE: DNA
<213> ORGANISM: Artificial Sequence
<220> FEATURE:
<223> OTHER INFORMATION: primer

<400> SEQUENCE: 76
ttgaaggttg ggttggtctc ctgtgccgtt gccacaggtg cggcca        46

<210> SEQ ID NO 77
<211> LENGTH: 46
<212> TYPE: DNA
<213> ORGANISM: Artificial Sequence
<220> FEATURE:
<223> OTHER INFORMATION: primer

<400> SEQUENCE: 77
ggaaatgctg gggtcttttc tgctgccgtt gccacaggtg cggcca        46

<210> SEQ ID NO 78
<211> LENGTH: 39
<212> TYPE: DNA
<213> ORGANISM: Artificial Sequence
<220> FEATURE:
<223> OTHER INFORMATION: primer

<400> SEQUENCE: 78
gcagaaaaga ccccagcatt tccaacaatc ccgctgagc               39

<210> SEQ ID NO 79
<211> LENGTH: 41
<212> TYPE: DNA
<213> ORGANISM: Artificial Sequence
<220> FEATURE:
<223> OTHER INFORMATION: primer

<400> SEQUENCE: 79
caggagacca acccaaccgg ccctgaaact ctgtgtggtg c            41

<210> SEQ ID NO 80
<211> LENGTH: 34
```

```
<212> TYPE: DNA
<213> ORGANISM: Artificial Sequence
<220> FEATURE:
<223> OTHER INFORMATION: primer

<400> SEQUENCE: 80
gccggtacct catgcggatt ttgcgggctt cagg                               34

<210> SEQ ID NO 81
<211> LENGTH: 41
<212> TYPE: DNA
<213> ORGANISM: Artificial Sequence
<220> FEATURE:
<223> OTHER INFORMATION: primer

<400> SEQUENCE: 81
gcaccacaca gagtttcagg gccggttggg ttggtctcct g                       41

<210> SEQ ID NO 82
<211> LENGTH: 60
<212> TYPE: DNA
<213> ORGANISM: Artificial Sequence
<220> FEATURE:
<223> OTHER INFORMATION: Teriparatide

<400> SEQUENCE: 82
agcgtctccg agattcagct tatgcacaac ctgggcaagc acttgaactc catggagcga   60

<210> SEQ ID NO 83
<211> LENGTH: 62
<212> TYPE: DNA
<213> ORGANISM: Artificial Sequence
<220> FEATURE:
<223> OTHER INFORMATION: Teriparatide

<400> SEQUENCE: 83
gaagttgtgg acatcttgca gtttctttcg cagccattcg actcgctcca tggagttcaa   60
gt                                                                  62

<210> SEQ ID NO 84
<211> LENGTH: 25
<212> TYPE: DNA
<213> ORGANISM: Artificial Sequence
<220> FEATURE:
<223> OTHER INFORMATION: primer

<400> SEQUENCE: 84
agcgtctccg agattcagct tatgc                                         25

<210> SEQ ID NO 85
<211> LENGTH: 33
<212> TYPE: DNA
<213> ORGANISM: Artificial Sequence
<220> FEATURE:
<223> OTHER INFORMATION: primer

<400> SEQUENCE: 85
gccggtacct cagaagttgt ggacatcttg cag                                33

<210> SEQ ID NO 86
<211> LENGTH: 114
<212> TYPE: DNA
<213> ORGANISM: Artificial Sequence
<220> FEATURE:
<223> OTHER INFORMATION: Teriparatide
```

<400> SEQUENCE: 86
agcgtctccg agattcagct tatgcacaac ctgggcaagc acttgaactc catggagcga    60
gtcgaatggc tgcgaaagaa actgcaagat gtccacaact tctgaggtac cggc         114

<210> SEQ ID NO 87
<211> LENGTH: 48
<212> TYPE: DNA
<213> ORGANISM: Artificial Sequence
<220> FEATURE:
<223> OTHER INFORMATION: primer

<400> SEQUENCE: 87
gcataagctg aatctcggag acgcttgccg ttgccacagg tgcggcca                 48

<210> SEQ ID NO 88
<211> LENGTH: 48
<212> TYPE: DNA
<213> ORGANISM: Artificial Sequence
<220> FEATURE:
<223> OTHER INFORMATION: primer

<400> SEQUENCE: 88
gcataagctg aatctcggag acgctagcga atgctgggat agctacgc                 48

<210> SEQ ID NO 89
<211> LENGTH: 46
<212> TYPE: DNA
<213> ORGANISM: Artificial Sequence
<220> FEATURE:
<223> OTHER INFORMATION: primer

<400> SEQUENCE: 89
ccaacccaac catcgagggc cgcagcgtct ccgagattca gcttat                   46

<210> SEQ ID NO 90
<211> LENGTH: 25
<212> TYPE: DNA
<213> ORGANISM: Artificial Sequence
<220> FEATURE:
<223> OTHER INFORMATION: primer

<400> SEQUENCE: 90
gcggccctcg atggttgggt tggtc                                          25

<210> SEQ ID NO 91
<211> LENGTH: 43
<212> TYPE: PRT
<213> ORGANISM: Corynebacterium glutamicum

<400> SEQUENCE: 91

Met Arg Asp Thr Ala Phe Arg Ser Ile Lys Ala Lys Ala Gln Ala Lys
1               5                   10                  15

Arg Arg Ser Leu Trp Ile Ala Ala Gly Ala Val Pro Thr Ala Ile Ala
            20                  25                  30

Leu Thr Met Ser Leu Ala Pro Met Ala Ser Ala
        35                  40

<210> SEQ ID NO 92
<211> LENGTH: 30
<212> TYPE: PRT
<213> ORGANISM: Corynebacterium glutamicum

<400> SEQUENCE: 92

```
Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala
            20                  25                  30

<210> SEQ ID NO 93
<211> LENGTH: 25
<212> TYPE: PRT
<213> ORGANISM: Corynebacterium stationis

<400> SEQUENCE: 93

Met Lys Arg Met Lys Ser Leu Ala Ala Ala Leu Thr Val Ala Gly Ala
1               5                   10                  15

Met Leu Ala Ala Pro Val Ala Thr Ala
            20                  25

<210> SEQ ID NO 94
<211> LENGTH: 1500
<212> TYPE: DNA
<213> ORGANISM: Corynebacterium glutamicum ATCC13869
<220> FEATURE:
<221> NAME/KEY: CDS
<222> LOCATION: (1)..(1500)

<400> SEQUENCE: 94
```

| | | | | | | | | | | | | | | | | |
|---|---|---|---|---|---|---|---|---|---|---|---|---|---|---|---|---|
| atg | ttt | aac | aac | cgt | atc | cgc | act | gca | gct | ctc | gct | ggt | gca | atc | gca | 48 |
| Met | Phe | Asn | Asn | Arg | Ile | Arg | Thr | Ala | Ala | Leu | Ala | Gly | Ala | Ile | Ala | |
| 1 | | | | 5 | | | | | 10 | | | | | 15 | | |
| atc | tcc | acc | gca | gct | tcc | ggc | gta | gct | atc | cca | gca | ttc | gct | cag | gag | 96 |
| Ile | Ser | Thr | Ala | Ala | Ser | Gly | Val | Ala | Ile | Pro | Ala | Phe | Ala | Gln | Glu | |
| | | | 20 | | | | | 25 | | | | | 30 | | | |
| acc | aac | cca | acc | ttc | aac | atc | aac | aac | ggc | ttc | aac | gat | gct | gat | gga | 144 |
| Thr | Asn | Pro | Thr | Phe | Asn | Ile | Asn | Asn | Gly | Phe | Asn | Asp | Ala | Asp | Gly | |
| | | | 35 | | | | | 40 | | | | | 45 | | | |
| tcc | acc | atc | cag | cca | gtt | gag | cca | gtt | aac | cac | acc | gag | gaa | acc | ctc | 192 |
| Ser | Thr | Ile | Gln | Pro | Val | Glu | Pro | Val | Asn | His | Thr | Glu | Glu | Thr | Leu | |
| | 50 | | | | | 55 | | | | | 60 | | | | | |
| cgc | gac | ctg | act | gac | tcc | acc | ggc | gct | tac | ctg | gaa | gag | ttc | cag | tac | 240 |
| Arg | Asp | Leu | Thr | Asp | Ser | Thr | Gly | Ala | Tyr | Leu | Glu | Glu | Phe | Gln | Tyr | |
| 65 | | | | | 70 | | | | | 75 | | | | | 80 | |
| ggc | aac | gtt | gag | gaa | atc | gtt | gaa | gca | tac | ctg | cag | gtt | cag | gct | tcc | 288 |
| Gly | Asn | Val | Glu | Glu | Ile | Val | Glu | Ala | Tyr | Leu | Gln | Val | Gln | Ala | Ser | |
| | | | | 85 | | | | | 90 | | | | | 95 | | |
| gca | gac | gga | ttc | gat | cct | tct | gag | cag | gct | gct | tac | gag | gct | ttc | gag | 336 |
| Ala | Asp | Gly | Phe | Asp | Pro | Ser | Glu | Gln | Ala | Ala | Tyr | Glu | Ala | Phe | Glu | |
| | | | 100 | | | | | 105 | | | | | 110 | | | |
| gct | gct | cgc | gtt | cgt | gca | tcc | cag | gag | ctc | gcg | gct | tcc | gct | gag | acc | 384 |
| Ala | Ala | Arg | Val | Arg | Ala | Ser | Gln | Glu | Leu | Ala | Ala | Ser | Ala | Glu | Thr | |
| | | | 115 | | | | | 120 | | | | | 125 | | | |
| atc | act | aag | acc | cgc | gag | tcc | gtt | gct | tac | gca | ctc | aag | gct | gac | cgc | 432 |
| Ile | Thr | Lys | Thr | Arg | Glu | Ser | Val | Ala | Tyr | Ala | Leu | Lys | Ala | Asp | Arg | |
| | 130 | | | | | 135 | | | | | 140 | | | | | |
| gaa | gct | acc | gca | gct | ttc | gag | gct | tac | ctc | agc | gct | ctt | cgt | cag | gtt | 480 |
| Glu | Ala | Thr | Ala | Ala | Phe | Glu | Ala | Tyr | Leu | Ser | Ala | Leu | Arg | Gln | Val | |
| 145 | | | | | 150 | | | | | 155 | | | | | 160 | |
| tca | gtc | atc | aac | gat | ctg | atc | gct | gat | gct | aac | gcc | aag | aac | aag | act | 528 |
| Ser | Val | Ile | Asn | Asp | Leu | Ile | Ala | Asp | Ala | Asn | Ala | Lys | Asn | Lys | Thr | |
| | | | | 165 | | | | | 170 | | | | | 175 | | |
| gac | ttt | gca | gag | atc | gag | ctc | tac | gat | gtt | ctt | tac | acc | gac | gcc | gac | 576 |
| Asp | Phe | Ala | Glu | Ile | Glu | Leu | Tyr | Asp | Val | Leu | Tyr | Thr | Asp | Ala | Asp | |
| | | | 180 | | | | | 185 | | | | | 190 | | | |

```
atc tct ggc gat gct cca ctt ctt gct cct gca tac aag gag ctg aag      624
Ile Ser Gly Asp Ala Pro Leu Leu Ala Pro Ala Tyr Lys Glu Leu Lys
        195                 200                 205 gac ctt cag gct gag gtt gac gca gac ttc gag tgg ttg ggc gag ttc      672
Asp Leu Gln Ala Glu Val Asp Ala Asp Phe Glu Trp Leu Gly Glu Phe
210                 215                 220 gca att gat aac aat gaa gac aac tac gtc att cgt act cac atc cct      720
Ala Ile Asp Asn Asn Glu Asp Asn Tyr Val Ile Arg Thr His Ile Pro
225                 230                 235                 240 gct gta gag gca ctc aag gca gcg atc gat tca ctg gtc gac acc gtt      768
Ala Val Glu Ala Leu Lys Ala Ala Ile Asp Ser Leu Val Asp Thr Val
        245                 250                 255 gag cca ctt cgt gca gac gct atc gct aag aac atc gag gct cag aag      816
Glu Pro Leu Arg Ala Asp Ala Ile Ala Lys Asn Ile Glu Ala Gln Lys
        260                 265                 270 tct gac gtt ctg gtt ccc cag ctc ttc ctc gag cgt gca act gca cag      864
Ser Asp Val Leu Val Pro Gln Leu Phe Leu Glu Arg Ala Thr Ala Gln
                275                 280                 285 cgc gac acc ctg cgt gtt gta gag gca atc ttc tct acc tct gct cgt      912
Arg Asp Thr Leu Arg Val Val Glu Ala Ile Phe Ser Thr Ser Ala Arg
        290                 295                 300 tac gtt gaa ctc tac gag aac gtc gag aac gtt aac gtt gag aac aag      960
Tyr Val Glu Leu Tyr Glu Asn Val Glu Asn Val Asn Val Glu Asn Lys
305                 310                 315                 320 acc ctt cgc cag cac tac tct tcc ctg atc cct aac ctc ttc atc gca     1008
Thr Leu Arg Gln His Tyr Ser Ser Leu Ile Pro Asn Leu Phe Ile Ala
                325                 330                 335 gcg gtt ggc aac atc aac gag ctc aac aat gca gat cag gct gca cgt     1056
Ala Val Gly Asn Ile Asn Glu Leu Asn Asn Ala Asp Gln Ala Ala Arg
                340                 345                 350 gag ctc ttc ctc gat tgg gac acc gac ctc acc acc aac gat gag gac     1104
Glu Leu Phe Leu Asp Trp Asp Thr Asp Leu Thr Thr Asn Asp Glu Asp
        355                 360                 365 gaa gct tac tac cag gct aag ctc gac ttc gct atc gag acc tac gca     1152
Glu Ala Tyr Tyr Gln Ala Lys Leu Asp Phe Ala Ile Glu Thr Tyr Ala
370                 375                 380 aag atc ctg atc aac ggt gaa gtt tgg cag gag cca ctc gct tac gtc     1200
Lys Ile Leu Ile Asn Gly Glu Val Trp Gln Glu Pro Leu Ala Tyr Val
385                 390                 395                 400 cag aac ctg gat gca ggc gca cgt cag gaa gca gct gac cgc gaa gca     1248
Gln Asn Leu Asp Ala Gly Ala Arg Gln Glu Ala Ala Asp Arg Glu Ala
                405                 410                 415 gag cgc gca gct gac gca gca tac cgc gct gag cag ctc cgc atc gct     1296
Glu Arg Ala Ala Asp Ala Ala Tyr Arg Ala Glu Gln Leu Arg Ile Ala
        420                 425                 430 cag gaa gca gct gac gct cag aag gct ctc gct gag gct ctt gct aat     1344
Gln Glu Ala Ala Asp Ala Gln Lys Ala Leu Ala Glu Ala Leu Ala Asn
        435                 440                 445 gca ggc aac aac gac aac ggt ggc gac aac tcc tcc gac gac aag gga     1392
Ala Gly Asn Asn Asp Asn Gly Gly Asp Asn Ser Ser Asp Asp Lys Gly
450                 455                 460 acc ggt tct tcc gac atc gga acc tgg gga cct ttc gca gca att gca     1440
Thr Gly Ser Ser Asp Ile Gly Thr Trp Gly Pro Phe Ala Ala Ile Ala
465                 470                 475                 480 gct atc atc gca gca atc gca gct atc ttc cca ttc ctc tcc ggt atc     1488
Ala Ile Ile Ala Ala Ile Ala Ala Ile Phe Pro Phe Leu Ser Gly Ile
                485                 490                 495 gtt aag ttc taa                                                     1500
Val Lys Phe
```

<210> SEQ ID NO 95
<211> LENGTH: 499
<212> TYPE: PRT
<213> ORGANISM: Corynebacterium glutamicum ATCC13869

<400> SEQUENCE: 95

```
Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala Gln Glu
            20                  25                  30

Thr Asn Pro Thr Phe Asn Ile Asn Asn Gly Phe Asn Asp Ala Asp Gly
        35                  40                  45

Ser Thr Ile Gln Pro Val Glu Pro Val Asn His Thr Glu Glu Thr Leu
    50                  55                  60

Arg Asp Leu Thr Asp Ser Thr Gly Ala Tyr Leu Glu Glu Phe Gln Tyr
65                  70                  75                  80

Gly Asn Val Glu Glu Ile Val Glu Ala Tyr Leu Gln Val Gln Ala Ser
                85                  90                  95

Ala Asp Gly Phe Asp Pro Ser Glu Gln Ala Ala Tyr Glu Ala Phe Glu
            100                 105                 110

Ala Ala Arg Val Arg Ala Ser Gln Glu Leu Ala Ala Ser Ala Glu Thr
        115                 120                 125

Ile Thr Lys Thr Arg Glu Ser Val Ala Tyr Ala Leu Lys Ala Asp Arg
    130                 135                 140

Glu Ala Thr Ala Ala Phe Glu Ala Tyr Leu Ser Ala Leu Arg Gln Val
145                 150                 155                 160

Ser Val Ile Asn Asp Leu Ile Ala Asp Ala Asn Ala Lys Asn Lys Thr
                165                 170                 175

Asp Phe Ala Glu Ile Glu Leu Tyr Asp Val Leu Tyr Thr Asp Ala Asp
            180                 185                 190

Ile Ser Gly Asp Ala Pro Leu Leu Ala Pro Ala Tyr Lys Glu Leu Lys
        195                 200                 205

Asp Leu Gln Ala Glu Val Asp Ala Asp Phe Glu Trp Leu Gly Glu Phe
    210                 215                 220

Ala Ile Asp Asn Asn Glu Asp Asn Tyr Val Ile Arg Thr His Ile Pro
225                 230                 235                 240

Ala Val Glu Ala Leu Lys Ala Ala Ile Asp Ser Leu Val Asp Thr Val
                245                 250                 255

Glu Pro Leu Arg Ala Asp Ala Ile Ala Lys Asn Ile Glu Ala Gln Lys
            260                 265                 270

Ser Asp Val Leu Val Pro Gln Leu Phe Leu Glu Arg Ala Thr Ala Gln
        275                 280                 285

Arg Asp Thr Leu Arg Val Val Glu Ala Ile Phe Ser Thr Ser Ala Arg
    290                 295                 300

Tyr Val Glu Leu Tyr Glu Asn Val Glu Asn Val Asn Val Glu Asn Lys
305                 310                 315                 320

Thr Leu Arg Gln His Tyr Ser Ser Leu Ile Pro Asn Leu Phe Ile Ala
                325                 330                 335

Ala Val Gly Asn Ile Asn Glu Leu Asn Asn Ala Asp Gln Ala Ala Arg
            340                 345                 350

Glu Leu Phe Leu Asp Trp Asp Thr Asp Leu Thr Thr Asn Asp Glu Asp
        355                 360                 365

Glu Ala Tyr Tyr Gln Ala Lys Leu Asp Phe Ala Ile Glu Thr Tyr Ala
    370                 375                 380
```

```
Lys Ile Leu Ile Asn Gly Glu Val Trp Gln Glu Pro Leu Ala Tyr Val
385                 390                 395                 400

Gln Asn Leu Asp Ala Gly Ala Arg Gln Glu Ala Ala Asp Arg Glu Ala
            405                 410                 415

Glu Arg Ala Ala Asp Ala Ala Tyr Arg Ala Glu Gln Leu Arg Ile Ala
        420                 425                 430

Gln Glu Ala Ala Asp Ala Gln Lys Ala Leu Ala Glu Ala Leu Ala Asn
    435                 440                 445

Ala Gly Asn Asn Asp Asn Gly Gly Asp Asn Ser Ser Asp Asp Lys Gly
450                 455                 460

Thr Gly Ser Ser Asp Ile Gly Thr Trp Gly Pro Phe Ala Ala Ile Ala
465                 470                 475                 480

Ala Ile Ile Ala Ala Ile Ala Ala Ile Phe Pro Phe Leu Ser Gly Ile
                485                 490                 495

Val Lys Phe

<210> SEQ ID NO 96
<211> LENGTH: 469
<212> TYPE: PRT
<213> ORGANISM: Corynebacterium glutamicum ATCC13869

<400> SEQUENCE: 96

Gln Glu Thr Asn Pro Thr Phe Asn Ile Asn Asn Gly Phe Asn Asp Ala
1               5                   10                  15

Asp Gly Ser Thr Ile Gln Pro Val Glu Pro Val Asn His Thr Glu Glu
            20                  25                  30

Thr Leu Arg Asp Leu Thr Asp Ser Thr Gly Ala Tyr Leu Glu Glu Phe
        35                  40                  45

Gln Tyr Gly Asn Val Glu Glu Ile Val Glu Ala Tyr Leu Gln Val Gln
    50                  55                  60

Ala Ser Ala Asp Gly Phe Asp Pro Ser Glu Gln Ala Ala Tyr Glu Ala
65                  70                  75                  80

Phe Glu Ala Ala Arg Val Arg Ala Ser Gln Glu Leu Ala Ala Ser Ala
                85                  90                  95

Glu Thr Ile Thr Lys Thr Arg Glu Ser Val Ala Tyr Ala Leu Lys Ala
            100                 105                 110

Asp Arg Glu Ala Thr Ala Ala Phe Glu Ala Tyr Leu Ser Ala Leu Arg
        115                 120                 125

Gln Val Ser Val Ile Asn Asp Leu Ile Ala Asp Ala Asn Ala Lys Asn
    130                 135                 140

Lys Thr Asp Phe Ala Glu Ile Glu Leu Tyr Asp Val Leu Tyr Thr Asp
145                 150                 155                 160

Ala Asp Ile Ser Gly Asp Ala Pro Leu Leu Ala Pro Ala Tyr Lys Glu
                165                 170                 175

Leu Lys Asp Leu Gln Ala Glu Val Asp Ala Asp Phe Glu Trp Leu Gly
            180                 185                 190

Glu Phe Ala Ile Asp Asn Asn Glu Asp Asn Tyr Val Ile Arg Thr His
        195                 200                 205

Ile Pro Ala Val Glu Ala Leu Lys Ala Ala Ile Asp Ser Leu Val Asp
    210                 215                 220

Thr Val Glu Pro Leu Arg Ala Asp Ala Ile Ala Lys Asn Ile Glu Ala
225                 230                 235                 240

Gln Lys Ser Asp Val Leu Val Pro Gln Leu Phe Leu Glu Arg Ala Thr
                245                 250                 255
```

-continued

```
Ala Gln Arg Asp Thr Leu Arg Val Val Glu Ala Ile Phe Ser Thr Ser
            260                 265                 270

Ala Arg Tyr Val Glu Leu Tyr Glu Asn Val Glu Asn Val Asn Val Glu
        275                 280                 285

Asn Lys Thr Leu Arg Gln His Tyr Ser Ser Leu Ile Pro Asn Leu Phe
    290                 295                 300

Ile Ala Ala Val Gly Asn Ile Asn Glu Leu Asn Asn Ala Asp Gln Ala
305                 310                 315                 320

Ala Arg Glu Leu Phe Leu Asp Trp Asp Thr Asp Leu Thr Asn Asp
                325                 330                 335

Glu Asp Glu Ala Tyr Tyr Gln Ala Lys Leu Asp Phe Ala Ile Glu Thr
                340                 345                 350

Tyr Ala Lys Ile Leu Ile Asn Gly Glu Val Trp Gln Glu Pro Leu Ala
            355                 360                 365

Tyr Val Gln Asn Leu Asp Ala Gly Ala Arg Gln Glu Ala Ala Asp Arg
        370                 375                 380

Glu Ala Glu Arg Ala Ala Asp Ala Ala Tyr Arg Ala Glu Gln Leu Arg
385                 390                 395                 400

Ile Ala Gln Glu Ala Ala Asp Ala Gln Lys Ala Leu Ala Glu Ala Leu
                405                 410                 415

Ala Asn Ala Gly Asn Asn Asp Asn Gly Gly Asp Asn Ser Ser Asp Asp
            420                 425                 430

Lys Gly Thr Gly Ser Ser Asp Ile Gly Thr Trp Gly Pro Phe Ala Ala
            435                 440                 445

Ile Ala Ala Ile Ile Ala Ala Ile Ala Ala Ile Phe Pro Phe Leu Ser
    450                 455                 460

Gly Ile Val Lys Phe
465

<210> SEQ ID NO 97
<211> LENGTH: 6
<212> TYPE: PRT
<213> ORGANISM: Corynebacterium glutamicum

<400> SEQUENCE: 97

Gln Glu Thr Asn Pro Thr
1               5

<210> SEQ ID NO 98
<211> LENGTH: 6
<212> TYPE: PRT
<213> ORGANISM: Corynebacterium glutamicum

<400> SEQUENCE: 98

Gln Glu Thr Gly Thr Tyr
1               5

<210> SEQ ID NO 99
<211> LENGTH: 6
<212> TYPE: PRT
<213> ORGANISM: Corynebacterium glutamicum

<400> SEQUENCE: 99

Gln Glu Thr Thr Val Thr
1               5

<210> SEQ ID NO 100
<211> LENGTH: 6
```

```
<212> TYPE: PRT
<213> ORGANISM: Corynebacterium glutamicum

<400> SEQUENCE: 100

Gln Glu Thr Pro Val Thr
1               5

<210> SEQ ID NO 101
<211> LENGTH: 6
<212> TYPE: PRT
<213> ORGANISM: Corynebacterium glutamicum

<400> SEQUENCE: 101

Gln Glu Thr Ala Val Thr
1               5

<210> SEQ ID NO 102
<211> LENGTH: 4
<212> TYPE: PRT
<213> ORGANISM: Corynebacterium glutamicum
<220> FEATURE:
<221> NAME/KEY: MISC_FEATURE
<222> LOCATION: (4)..(4)
<223> OTHER INFORMATION: Xaa is Asn, Gly, Thr, Pro, or Ala

<400> SEQUENCE: 102

Gln Glu Thr Xaa
1

<210> SEQ ID NO 103
<211> LENGTH: 5
<212> TYPE: PRT
<213> ORGANISM: Corynebacterium glutamicum
<220> FEATURE:
<221> NAME/KEY: MISC_FEATURE
<222> LOCATION: (4)..(4)
<223> OTHER INFORMATION: Xaa is Asn, Gly, Thr, Pro, or Ala
<220> FEATURE:
<221> NAME/KEY: MISC_FEATURE
<222> LOCATION: (5)..(5)
<223> OTHER INFORMATION: Xaa is Pro, Thr, or Val

<400> SEQUENCE: 103

Gln Glu Thr Xaa Xaa
1               5

<210> SEQ ID NO 104
<211> LENGTH: 6
<212> TYPE: PRT
<213> ORGANISM: Corynebacterium glutamicum
<220> FEATURE:
<221> NAME/KEY: MISC_FEATURE
<222> LOCATION: (4)..(4)
<223> OTHER INFORMATION: Xaa is Asn, Gly, Thr, Pro, or Ala
<220> FEATURE:
<221> NAME/KEY: MISC_FEATURE
<222> LOCATION: (5)..(5)
<223> OTHER INFORMATION: Xaa is Pro, Thr, or Val
<220> FEATURE:
<221> NAME/KEY: MISC_FEATURE
<222> LOCATION: (6)..(6)
<223> OTHER INFORMATION: Xaa is Thr or Tyr

<400> SEQUENCE: 104

Gln Glu Thr Xaa Xaa Xaa
1               5

<210> SEQ ID NO 105
<211> LENGTH: 4
```

```
<212> TYPE: PRT
<213> ORGANISM: Artificial Sequence
<220> FEATURE:
<223> OTHER INFORMATION: Factor Xa

<400> SEQUENCE: 105

Ile Glu Gly Arg
1

<210> SEQ ID NO 106
<211> LENGTH: 6
<212> TYPE: PRT
<213> ORGANISM: Artificial Sequence
<220> FEATURE:
<223> OTHER INFORMATION: ProTEV

<400> SEQUENCE: 106

Glu Asn Leu Tyr Phe Gln
1               5

<210> SEQ ID NO 107
<211> LENGTH: 6
<212> TYPE: PRT
<213> ORGANISM: Corynebacterium stationis

<400> SEQUENCE: 107

Ala Glu Lys Thr Pro Ala
1               5
```